United States Patent [19] [11] 4,057,414
Fischer, deceased [45] Nov. 8, 1977

[54] HERBICIDAL COMPOSITIONS

[75] Inventor: Adolf Fischer, deceased, late of Mutterstadt, Germany, by Caecilia Emma Fischer, heiress-at-law

[73] Assignee: BASF Aktiengesellschaft, Ludwigshafen (Rhine), Germany

[21] Appl. No.: 627,965

[22] Filed: Nov. 3, 1975

[30] Foreign Application Priority Data

Nov. 18, 1974 Germany .............................. 2454576

[51] Int. Cl.[2] .............................................. A01N 9/00

[52] U.S. Cl. ........................................... 71/88; 71/92; 71/93; 71/94; 71/95; 71/100; 71/101; 71/103; 71/105; 71/106; 71/107; 71/108; 71/109; 71/111; 71/113; 71/115; 71/121; 71/118

[58] Field of Search ..................................... 71/118, 88

[56] References Cited

U.S. PATENT DOCUMENTS

| | | | |
|---|---|---|---|
| 3,134,666 | 5/1964 | McRae | 71/118 |
| 3,154,398 | 10/1964 | McRae | 71/118 |
| 3,333,948 | 8/1967 | Takematsu et al. | 71/118 |
| 3,443,927 | 5/1969 | Unger | 71/118 |
| 3,852,058 | 12/1974 | Huffman | 71/118 |
| 3,883,509 | 5/1975 | Fischer et al. | 71/94 |

*Primary Examiner*—Glennon H. Hollrah
*Attorney, Agent, or Firm*—Keil, Thompson & Shurtleff

[57] ABSTRACT

Herbicides containing compositions of glycolic acid amides and other active ingredients.

1 Claim, No Drawings

HERBICIDAL COMPOSITIONS

The present invention application relates to herbicides containing compositions of sulfonylglycolic acid amides or sulfonylglycolic acid imides.

It is known that pyridazones (German 1,105,232), benzofuranyl sulfonates (German Laid-Open Application DOS 1,926,139), benzofuranylalkylamino sulfonates (German Laid-Open Application DOS 2,324,592), azetidine carbothiolates (German Laid-Open Application DOS 2,312,045), fatty acids (German 959,066), thiol carbamates (U.S. 3,185,720; U.S. 3,330,821), carbamates (German Laid-Open Application DOS 1,567,151; German Printed Application DAS 1,137,255), pyrazolium compounds (German Laid-Open Application DOS 2,260,485), α-cyanoacrylates (German Laid-Open Application DOS 1,642,231), anilides (British 903,766) and 1,2,4-triazinones (German Laid-Open Application DOS 2,138,031) have a herbicidal action. However, this action is not always satisfactory.

We have now found that compositions of one or more of these active ingredients and sulfonylglycolic acid amides (German Laid-Open Applications DOS 2,201,432 and 2,334,715) or sulfonylglycolic acid imides (German Laid-Open Application DOS 2,219,923), which are known as individual herbicidal active ingredients, have an unforeseeably superior herbicidal action over their individual components.

These compositions consist of a) a glycolic acid amide of the formula

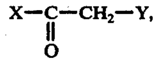

where X denotes

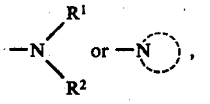

$R^1$ denoting alkyl, alkenyl, alkynyl, haloalkyl, haloalkenyl or haloalkynyl of a maximum of 6 carbon atoms, alkoxyalkyl, haloalkoxyalkyl, alkenoxyalkyl, alkynoxyalkyl or cycloalkyl, and $R^2$ denoting phenyl which may bear one or more identical or different substituents, the number of substituents, which may be halogen, lower alkyl of a maximum of 4 carbon atoms, haloalkyl, alkoxy, alkylsulfonyl, alkylaminosulfonyl, cyano, hydroxy, nitro or amino, being from 0 to 3, and the carbonamide nitrogen being a ring member of an optionally bicycic cycloalkylimine which may be substituted by halogen or lower alkyl; which may contain further hetero atoms in the ring; and which has a maximum of 9 carbon atoms, and Y denotes

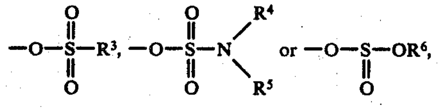

$R^3$, $R^4$, $R^5$ and $R^6$ denoting alkyl, alkenyl, alkynyl, haloalkyl, haloalkenyl or haloalkynyl of a maximum of 8 carbon atoms, unsubstituted or substituted phenyl or cycloalkyl of a maximum of 8 carbon atoms, and $R^4$ and $R^5$ additionally denoting hydrogen, and b. a pyridazone derivative of the formula

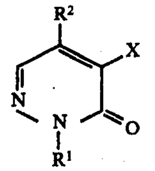

where X denotes chloro, bromo, iodo or methoxy, $R^1$ denotes phenyl which may be substituted by methyl, trifluoromethyl or halogen and $R^2$ denotes amino, α-hydroxy-β,β,β-trichloroethylamino, acetylamino, haloacetylamino, methoxy,

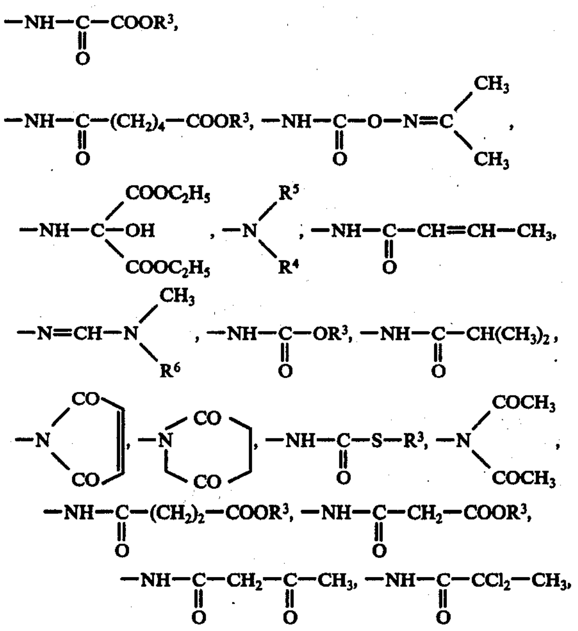

$R^3$ denoting hydrogen, a cation, a substituted aliphatic amine, unsubstituted or halogen-substituted alkyl or alkenyl, unsubstituted or substituted phenyl or hydroxyethyl, $R^4$ denoting hydrogen, methyl, methoxy or ethyl, $R^5$ denoting methyl, ethyl or methoxy, and $R^6$ denoting hydrogen or methyl, or c. benzofuranyl sulfonate of the formula

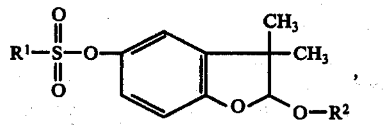

where $R^1$ denotes lower alkyl or the group

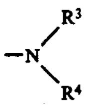

and $R^2$ denotes lower alkyl or has the same meanings as $R^3$ and $R^4$ when $R^1$ is

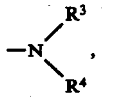

$R^3$ and $R^4$ denoting hydrogen or an unsubstituted or halogen- or alkoxy-substituted aliphatic radical of a maximum of 4 carbon atoms, or d. a benzofuranylalkylamino sulfonate of the formula

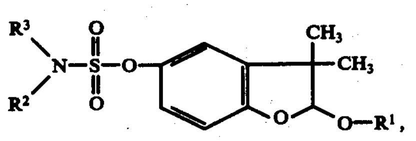

where $R^1$ denotes hydrogen, lower alkyl, alkenyl, alkynyl, haloalkyl, haloalkenyl, haloalkynyl, alkoxy, or radicals such as

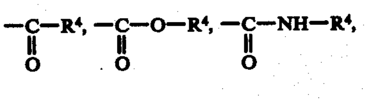

$R^4$ denoting unsubstituted or halogen-substituted lower alkyl, $R^2$ is different from $R^1$ and denotes hydrogen, a cation, lower alkyl, alkenyl, alkynyl or the groups

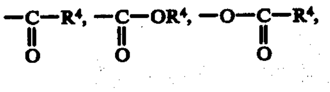

$R^4$ have the above meanings, and $R^3$ denotes hydrogen or unsubstituted or halogen-substituted lower alkyl, or e. an azetidine carbothiolate of the formula

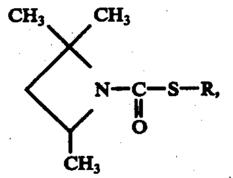

where R denotes alkyl, alkenyl or benzyl which may be substituted by halogen, cyano, alkoxy or methyl, and/or f. a carboxylic acid derivative of the formula

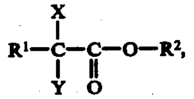

which may be in the form of the free acid or salts thereof and in which $R^2$ denotes unsubstituted or halogen-substituted alkyl or benzyl, X and Y denote hydrogen or halogen, and $R^1$ denotes halogen, lower alkyl, haloalkyl, unsubstituted or substituted benzyl, or benzamidooxy, or g. a thiol carbamate of the formula

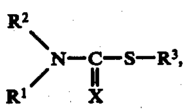

where $R^1$ denotes lower alkyl or an unsubstituted or methyl-substituted cycloaliphatic, bicycloaliphatic or tricycloaliphatic radical, $R^2$ denotes lower alkyl, alkenyl or alkynyl, $R^3$ denotes unsubstituted or halogen-substituted alkyl, alkenyl or benzyl, and X denotes oxygen or sulfur, or h. a carbamate of the formula

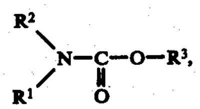

where $R^1$ denotes hydrogen or methyl, $R^2$ denotes hydrogen, phenyl or phenylsulfonyl which may be substituted by halogen, methyl, amino or nitro, and $R^3$ denotes unsubstituted or halogen-substituted alkyl, alkenyl, alkynyl or benzyl,

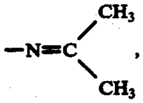 , 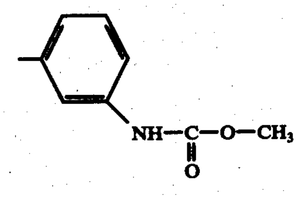 or

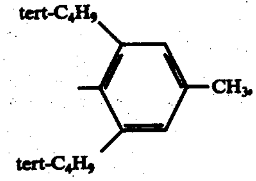 or i. a phenyl carbamate of the formula

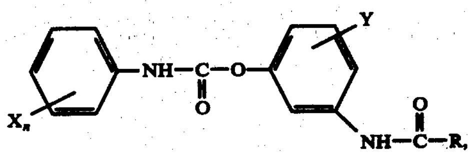

where Y denotes hydrogen or methyl, R denotes methoxy, ethoxy,

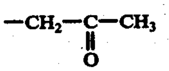 or 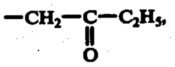

X denotes identical or different substituents such as halogen, haloalkyl, lower alkyl or methoxy, and $n$ denotes one of the integers 0, 1, 2 and 3, or j. a pyrazolium derivative of the formula

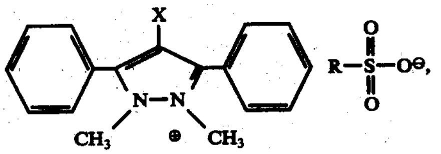

where R denotes methyl, methoxy or p-methylphenyl and X denotes bromo, hydrogen, methoxy or methyl, or k. the $\alpha$-cyanoacrylate of the formula

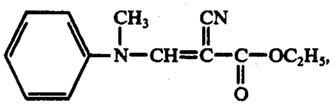

1. an anilide of the formula

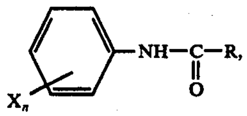

where X denotes hydrogen, halogen, or methyl, *n* denotes one of the integers 0, 1 and 2, and R denotes alkyl or alkenyl, or m. a 1,2,4-triazinone of the formula

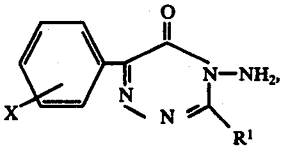

where X denotes hydrogen, methyl or trifluoromethyl and $R^1$ denotes methyl.

The compositions may contain one or more compounds of the formula a and/or compounds of the formulae *b* to *m*.

Examples of suitable components according to the invention are the active ingredients listed below:

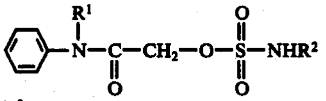

| $R^1$ | $R^2$ |
|---|---|
| $CH_3$ | H |
| $CH_3$ | $CH_3$ |
| $CH_3$ | $C_2H_5$ |
| $CH_3$ | $CH_2CH_2Cl$ |
| $CH_3$ | n-$C_3H_7$ |
| $CH_3$ | i-$C_3H_7$ |
| $CH_3$ | n-$C_4H_9$ |
| $CH_3$ | sec-$C_4H_9$ |
| $CH_3$ | i-$C_4H_9$ |
| $CH_3$ | 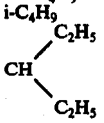 |
| $CH_3$ | 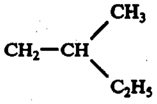 |
| $CH_3$ | 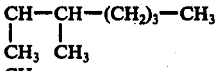 |
| $C_2H_5$ | $CH_3$ |
| $C_2H_5$ | $C_2H_5$ |
| $C_2H_5$ | $CH_2CH_2Cl$ |
| $C_2H_5$ | n-$C_3H_7$ |
| $C_2H_5$ | i-$C_3H_7$ |
| n-$C_3H_7$ | $CH_3$ |
| n-$C_3H_7$ | i-$C_3H_7$ |
| $C_2H_5$ | H |
| i-$C_3H_7$ | H |
| i-$C_3H_7$ | $CH_3$ |
| i-$C_3H_7$ | $C_2H_5$ |
| i-$C_3H_7$ | $CH_2CH_2Cl$ |
| i-$C_3H_7$ | n-$C_3H_7$ |
| i-$C_3H_7$ | i-$C_3H_7$ |
| i-$C_3H_7$ | n-$C_4H_9$ |
| i-$C_3H_7$ | sec-$C_4H_9$ |

-continued

| | |
|---|---|
| i-$C_3H_7$ | 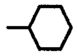 |
| $CH_2-CH=CH_2$ | $CH_3$ |
| $CH_2-C\equiv CH$ | $CH_3$ |
| $CH_2-C\equiv CH$ | i-$C_3H_7$ |
| n-$C_4H_9$ | $CH_3$ |
| n-$C_4H_9$ | $C_2H_5$ |
| n-$C_4H_9$ | n-$C_3H_7$ |
| n-$C_4H_9$ | i-$C_3H_7$ |
| sec-$C_4H_9$ | H |
| sec-$C_4H_9$ | $CH_3$ |
| sec-$C_4H_9$ | $C_2H_5$ |
| sec-$C_4H_9$ | $CH_2CH_2Cl$ |
| sec-$C_4H_9$ | n-$C_3H_7$ |
| sec-$C_4H_9$ | i-$C_3H_7$ |
| i-$C_4H_9$ | i-$C_3H_7$ |
| tert.-$C_4H_9$ | $CH_3$ |
| tert-$C_4H_9$ | $C_2H_5$ |
| tert-$C_4H_9$ | $CH_2CH_2Cl$ |
| tert-$C_4H_9$ | i-$C_3H_7$ |
| 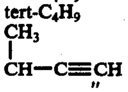 | H |
| " | $CH_3$ |
| " | $C_2H_5$ |
| " | $CH_2CH_2Cl$ |
| " | n-$C_3H_7$ |
| " | i-$C_3H_7$ |
| " | n-$C_4H_9$ |
| " | i-$C_3H_7$ |
| 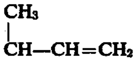 | |

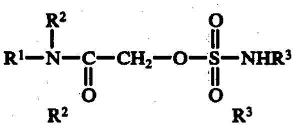

| $R^1$ | $R^2$ | $R^3$ |
|---|---|---|
| 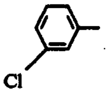 | $CH_3$ | $CH_3$ |
| 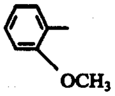 | $CH_3$ | $CH_3$ |
| 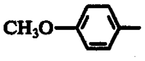 | $CH_3$ | $CH_3$ |
| 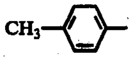 | $CH_3$ | $CH_3$ |
| 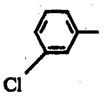 | $CH_3$ | $C_2H_5$ |
| 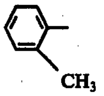 | $CH_3$ | $C_2H_5$ |
| 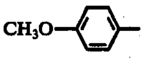 | $CH_3$ | $C_2H_5$ |
| 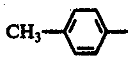 | $CH_3$ | $C_2H_5$ |
| 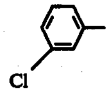 | $CH_3$ | i-$C_3H_7$ |
| 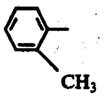 | $CH_3$ | i-$C_3H_7$ |
| 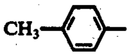 | $CH_3$ | i-$C_3H_7$ |
| 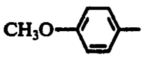 | $CH_3$ | i-$C_3H_7$ |

-continued

| | | |
|---|---|---|
| 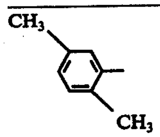 | $CH_3$ | i-$C_3H_7$ |
| 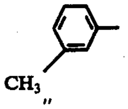 | $C_2H_5$ | $CH_3$ |
| " | $C_2H_5$ | $C_2H_5$ |
| " | $C_2H_5$ | n-$C_3H_7$ |
| " | $C_2H_5$ | i-$C_3H_7$ |
| 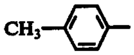 | $C_2H_5$ | i-$C_3H_7$ |
| 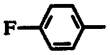 | i-$C_3H_7$ | $CH_3$ |
| 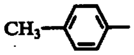 | i-$C_3H_7$ | $CH_3$ |
| 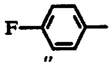 | i-$C_3H_7$ | $C_2H_5$ |
| " | i-$C_3H_7$ | n-$C_3H_7$ |
| " | i-$C_3H_7$ | i-$C_3H_7$ |
| 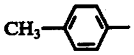 | i-$C_3H_7$ | i-$C_3H_7$ |
| 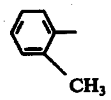 | 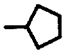 | i-$C_3H_7$ |

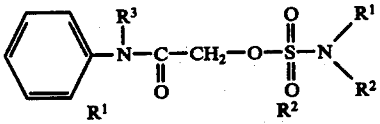

| $R^3$ | $R^1$ | $R^2$ |
|---|---|---|
| $CH_3$ | $CH_3$ | $CH_3$ |
| $CH_3$ | $CH_3$ | $C_2H_5$ |
| $C_2H_5$ | $CH_3$ | $CH_3$ |
| $C_2H_5$ | $CH_3$ | $C_2H_5$ |
| i-$C_3H_7$ | $CH_3$ | $CH_3$ |
| i-$C_3H_7$ | $CH_3$ | $C_2H_5$ |
| i-$C_3H_7$ | $CH_3$ | $C_2H_5$ |
| i-$C_3H_7$ | $C_2H_5$ | $C_2H_5$ |
| i-$C_3H_7$ | $CH_3$ | $CH_2CH_2Cl$ |
| sec-$C_4H_9$ | $CH_3$ | $CH_3$ |

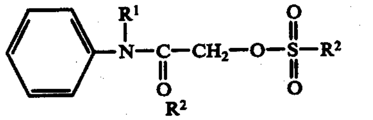

| $R^1$ | $R^2$ |
|---|---|
| $CH_2-C\equiv CH$ | $CH_3$ |
| i-$C_3H_7$ | $C_2H_5$ |
| i-$C_3H_7$ | n-$C_3H_7$ |
| i-$C_3H_7$ | i-$C_3H_7$ |
| i-$C_3H_7$ | n-$C_4H_9$ |
| tert-$C_4H_9$ | $CH_3$ |
| sec-$C_4H_9$ | $CH_3$ |
| i-$C_4H_9$ | $CH_3$ |
| $CH(CH_3)-CH=CH_2$ | $CH_3$ |
| $CH(CH_3)-C\equiv CH$ | $CH_3$ |
| " | $C_2H_5$ |
| " | n-$C_3H_7$ |
| " | i-$C_3H_7$ |
| " | n-$C_4H_9$ |
| " | 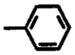 |
| " | 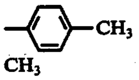 |
| i-$C_3H_7$ | $CH_3$ |

-continued

| | |
|---|---|
| $C(CH_3)_2-C\equiv CH$ | $CH_3$ |

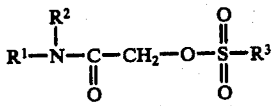

| $R^1$ | $R^2$ | $R^3$ |
|---|---|---|
| 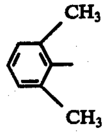 | $-CH_2-OCH_3$ | $CH_3$ |
| 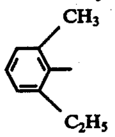 | $-CH_2-OCH_3$ | $CH_3$ |
| 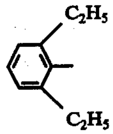 | $CH_2-OCH_3$ | $CH_3$ |
| " | $CH_2-OCH_3$ | $CH_2Cl$ |
| " | $CH_2-OCH_3$ | $C_2H_5$ |
| " | $CH_2-OCH_3$ | i-$C_3H_7$ |
| 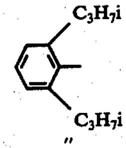 | $CH_2-OCH_3$ | $CH_3$ |
| " | $CH_2-OCH_3$ | $C_2H_5$ |
| 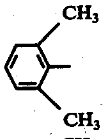 | $CH_2-OC_2H_5$ | $CH_3$ |
| 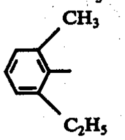 | $CH_2-OC_2H_5$ | $CH_3$ |
| " | $CH_2-OC_2H_5$ | $C_2H_5$ |
| " | $-CH_2-OC_2H_5$ | i-$C_3H_7$ |
| 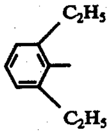 | $CH_2-OC_2H_5$ | $CH_3$ |
| 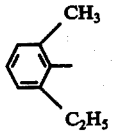 | $-CH_2OC_2H_5$ | $CH_2-CH(CH_3)_2$ |
| 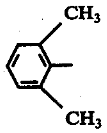 | $CH_2-OC_3H_7n$ | $CH_3$ |
| " | $CH_2-OC_3H_7n$ | $C_2H_5$ |
| " | $CH_2-O-CH(CH_3)_2$ | $C_2H_5$ |
| " | $CH_2-O-CH(CH_3)-C_2H_5$ | $C_2H_5$ |
| " | $CH_2-O-CH(CH_3)_2$ | $CH_3$ |
| " | $CH_2-O-CH(CH_3)-C_2H_5$ | $CH_3$ |

-continued

| | | |
|---|---|---|
| 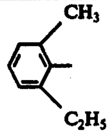 | $CH_2-OC_3H_7n$ | $CH_3$ |
| " | $CH_2-O-CH(CH_3)_2$ | $CH_3$ |
| 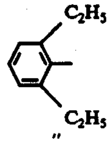 | $CH_2-OC_3H_7n$ | $CH_3$ |
| " | $CH_2-O-CH_2-CH=CH_2$ | $CH_3$ |
| 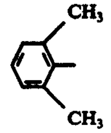 | $-CH_2-O-CH_2-C\equiv CH$ | $CH_3$ |
| 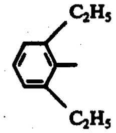 | $CH_2-O-CH(CH_3)_2$ | $CH_3$ |
| 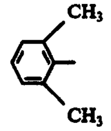 | $-CH_2-O-CH(CH_3)-C_2H_5$ | $CH_3$ |
| 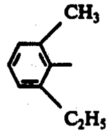 | $CH_2-O-C(CH_3)_3$ | $CH_3$ |
| 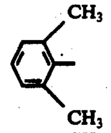 | $-CH_2-O-CH(CH_3)-C_2H_5$ | $C_2H_5$ |
| 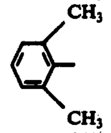 | $CH_2-O-CH_2-CH=CH_2$ | $CH_3$ |
| 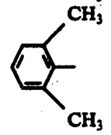 | $CH_2-O-CH_2-CH(CH_3)_2$ | $CH_3$ |

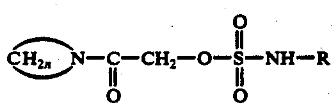

| R | n |
|---|---|
| $CH_3$ | 4 |
| $C_2H_5$ | 4 |
| $CH_2CH_2Cl$ | 4 |
| $i-C_3H_7$ | 4 |
| $n-C_3H_7$ | 4 |
| $n-C_4H_9$ | 4 |
| $sec.-C_4H_9$ | 4 |
| $i-C_4H_9$ | 4 |
| $CH_3$ | 5 |
| $C_2H_5$ | 5 |
| $n-C_3H_7$ | 5 |
| $i-C_3H_7$ | 5 |
| $n-C_4H_9$ | 5 |
| $CH_3$ | 6 |
| $C_2H_5$ | 6 |
| $CH_2CH_2Cl$ | 6 |
| $n-C_3H_7$ | 6 |
| $i-C_3H_7$ | 6 |
| $n-C_4H_9$ | 6 |
| $sec.-C_4H_9$ | 6 |
| $CH(C_2H_5)_2$ | 6 |
| $CH_2-CH(CH_3)C_2H_5$ | 6 |

-continued

| | |
|---|---|
| $CH_3$ | 7 |
| $C_2H_5$ | 7 |
| $i-C_3H_7$ | 7 |
| $n-C_3H_7$ | 7 |
| $-CH_2-CH_2-Cl$ | 7 |
| H | 8 (bicyclo) |
| $CH_3$ | 8 (bicyclo) |
| $C_2H_5$ | 8 (bicyclo) |
| $i-C_3H_7$ | 8 (bicyclo) |
| $n-C_3H_7$ | 8 (bicyclo) |
| $n-C_4H_9$ | 8 (bicyclo) |
| $sec-C_4H_9$ | 8 (bicyclo) |
| $i-C_4H_9$ | 8 (bicyclo) |

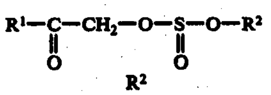

| $R^1$ | $R^2$ |
|---|---|
| 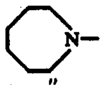 | $CH_3$ |
| " | $C_2H_5$ |
| " | $n-C_3H_7$ |
| " | $i-C_3H_7$ |
| " | $n-C_4H_9$ |
| " | $CH_2-CH=CH_2$ |
| 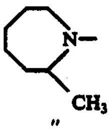 | $i-C_3H_7$ |
| " | $C_2H_5$ |
| 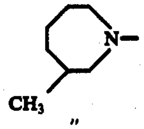 | $CH_3$ |
| " | $C_2H_5$ |
| " | $i-C_3H_7$ |
| 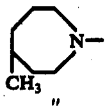 | $C_2H_5$ |
| " | $i-C_3H_7$ |
| 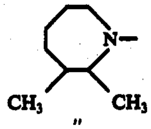 | $CH_3$ |
| " | $C_2H_5$ |
| " | $n-C_3H_7$ |
| " | $i-C_3H_7$ |

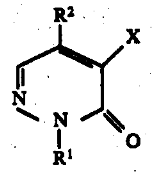

| $R^1$ | $R^2$ | X |
|---|---|---|
| 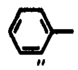 | $NH_2$ | Cl |
| " | $NH_2$ | Br |
| " | $NH-CHOHCCl_3$ | Br |
| " | 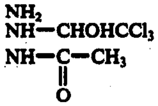 | Cl |
| " | 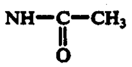 | Br |
| " | 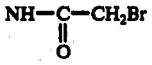 | Br |
| " | 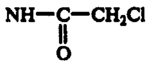 | Br |

-continued

| | | |
|---|---|---|
| " | $NH-C(=O)-CHCl_2$ | Br |
| " | $NH-C(=O)-CH_2-C(=O)-CH_3$ | Br |
| " | $NH-C(=O)-COONa$ | Br |
| " | $NH-C(=O)-COOCH_3$ | Br |
| " | $NH-C(=O)-COOC_2H_5$ | Br |
| " | $NH-C(=O)-COOCH(CH_3)_2$ | Br |
| " | $NH-C(=O)-COOC(CH_3)_3$ | Br |
| " | $NH-C(=O)-COOC_6H_5$ | Br |
| " | 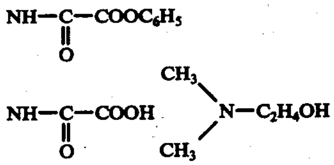 | Br |
| " | $OCH_3$ | Cl |
| " | $OCH_3$ | Br |
| " | $OCH_3$ | $OCH_3$ |
| " | $NH-C(=O)-(CH_2)_4-COOCH_3$ | Br |
| " | $NH-C(=O)-COOCH_2-CCl=CCl_2$ | Br |
| " | 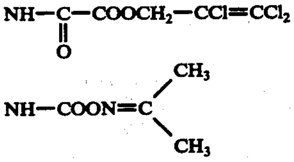 | Br |
| 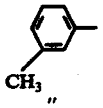 | $NH_2$ | Cl |
| " | $NH_2$ | Br |
| " | $NH-C(=O)-COOC(CH_3)_3$ | Br |
| " | $OCH_3$ | Br |
| " | $OCH_3$ | Cl |
| " | $OCH_3$ | $OCH_3$ |
| " | 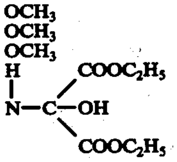 | Br |
| 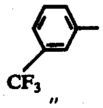 | $NH_2$ | Cl |
| " | $NH_2$ | Br |
| " | $NH-CHOHCCl_3$ | Br |
| " | $NH-CHOHCCl_3$ | Cl |
| " | $NH-C(=O)-CH_2Cl$ | Cl |
| " | $NH-C(=O)-CH_3$ | Br |
| " | 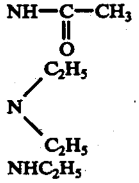 | Cl |
| " | $NHC_2H_5$ | Cl |
| " | $NH-C(=O)COOC_2H_5$ | Br |
| " | $NH-C(=O)-COOH$ | Br |

-continued

| | | |
|---|---|---|
| " | $NH-C(=O)-CHCl_2$ | Br |
| " | 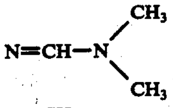 | Br |
| " | 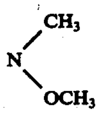 | Cl |
| " | 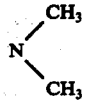 | Cl |
| " | 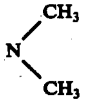 | Br |
| " | $NHCH_3$ | Cl |
| " | $NHCH_3$ | Br |
| " | $OCH_3$ | Cl |
| " | $OCH_3$ | Br |
| " | $OCH_3$ | $OCH_3$ |
| " | $NH-OCH_3$ | Cl |
| 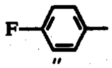 | $NH_2$ | Br |
| " | $NH-CHOH-CCl_3$ | Cl |
| " | $NH_2$ | Cl |
| " | $OCH_3$ | $OCH_3$ |
| " | $OCH_3$ | Br |
| 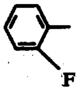 | $OCH_3$ | $OCH_3$ |
| 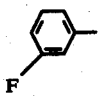 | $OCH_3$ | $OCH_3$ |
| 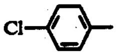 | $OCH_3$ | $OCH_3$ |
| 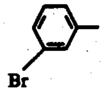 | $OCH_3$ | $OCH_3$ |
| 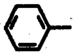 | $NH_2$ | J |
| " | $OCH_3$ | J |
| " | $NH-C(=O)-CH_2Cl$ | J |
| " | $NH-C(=O)-COOC_2H_5$ | J |
| " | $NH-C(=O)-CH=CH-CH_3$ | Cl |
| " | 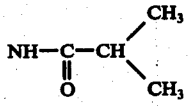 | Br |
| " | $NH-C(=O)-O-CH_2-CH_2OH$ | Cl |
| " | 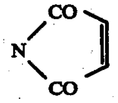 | Cl |
| " | 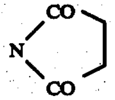 | Br |
| " | $NH-CHOHCCl_3$ | Cl |

-continued

| | | |
|---|---|---|
| " | $NH-\underset{\underset{O}{\|}}{C}-CH_2Cl$ | Cl |
| " | $N=CH-NHCH_3$ | Br |
| " | $N=CH-NH-CH_3$ | Cl |
| " | 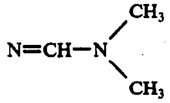 | Br |
| " | $NH-COSC_6H_5$ | Cl |
| " | 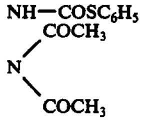 | Br |
| " | $NH-\underset{\underset{O}{\|}}{C}-(CH_2)_2COCH_3$ | Cl |
| " | $NH-\underset{\underset{O}{\|}}{C}-CH_2-COOC_2H_5$ | Br |
| " | $NH-\underset{\underset{O}{\|}}{C}-CCl_2-CH_3$ | Br |
| " | $NH-\underset{\underset{O}{\|}}{C}-CCl_3$ | Br |

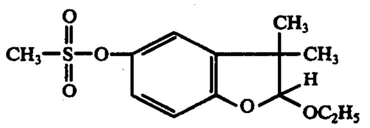

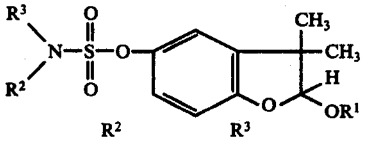

| $R^1$ | $R^2$ | $R^3$ |
|---|---|---|
| H | H | $i-C_3H_7$ |
| $CH_3$ | $CH_3$ | H |
| $CH_3$ | $i-C_3H_7$ | H |
| $CH_3$ | $n-C_3H_7$ | H |
| $C_2H_5$ | $CH_3$ | H |
| $C_2H_5$ | $C_2H_5$ | H |
| $C_2H_5$ | $i-C_3H_7$ | H |
| $CH_2CH_2Cl$ | $CH_3$ | H |
| $n-C_3H_7$ | $CH_3$ | H |
| $n-C_3H_7$ | $C_2H_5$ | H |
| $n-C_3H_7$ | $n-C_3H_7$ | H |
| $i-C_3H_7$ | $CH_3$ | H |
| $i-C_3H_7$ | $C_2H_5$ | H |
| $i-C_3H_7$ | $n-C_3H_7$ | H |
| $CH_2-CH=CH_2$ | $CH_3$ | H |
| $CH_2-C\equiv CH$ | $CH_3$ | H |
| H | $CH_3$ | $CH_3$ |
| H | $C_2H_5$ | $C_2H_5$ |
| $CH_3$ | $CH_3$ | $CH_3$ |
| $CH_3$ | $CH_3$ | $C_2H_5$ |
| $CH_3$ | $C_2H_5$ | $C_2H_5$ |
| $C_2H_5$ | $CH_3$ | $CH_3$ |
| $CH_2CH_2Cl$ | $CH_3$ | $CH_3$ |
| $CH_2-CH_2OCH_3$ | $CH_3$ | $CH_3$ |
| $C_2H_5$ | $CH_3$ | $CH_2-CH=CH_2$ |
| $C_2H_5$ | $C_2H_5$ | $C_2H_5$ |
| $n-C_3H_7$ | $CH_3$ | $CH_3$ |
| $i-C_3H_7$ | $CH_3$ | $CH_3$ |
| $CH_2-CH=CH_2$ | $CH_3$ | $CH_3$ |
| $CH_2-CH=CH_2$ | $C_2H_5$ | $C_2H_5$ |
| $CH_3$ | H | H |
| $C_2H_5$ | H | H |
| $\underset{\underset{O}{\|}}{C}-CH_3$ | $CH_3$ | $CH_3$ |
| $\underset{\underset{O}{\|}}{C}-CH_2Cl$ | $CH_3$ | $CH_3$ |
| $\underset{\underset{O}{\|}}{C}-CH_2Cl$ | $C_2H_5$ | $C_2H_5$ |
| $C_2H_5$ | $CH_3$ | $CH_2-C=CH$ |
| $C_2H_5$ | $CH_3$ | Na |
| $-\underset{\underset{O}{\|}}{C}-CH_3$ | $CH_3$ | $-\underset{\underset{O}{\|}}{C}-CH_3$ |
| $-\underset{\underset{O}{\|}}{C}-C_2H_5$ | $CH_3$ | $CH_3$ |
| $-\underset{\underset{O}{\|}}{C}-OCH_3$ | $CH_3$ | $CH_3$ |
| $-\underset{\underset{O}{\|}}{C}-OC_2H_5$ | $CH_3$ | $CH_3$ |
| $-CH_3$ | $CH_3$ | $-\underset{\underset{O}{\|}}{C}-CH_3$ |
| $CH_3$ | $CH_3$ | $-\underset{\underset{O}{\|}}{C}-CH_2Cl$ |
| $C_2H_5$ | $CH_3$ | $-\underset{\underset{O}{\|}}{C}-CH_3$ |
| $C_2H_5$ | $CH_3$ | $-\underset{\underset{O}{\|}}{C}-CH_2Cl$ |
| $C_2H_5$ | $C_2H_5$ | $O-\underset{\underset{O}{\|}}{C}-CH_3$ |
| $C_2H_5$ | $CH_3$ | $-\underset{\underset{O}{\|}}{C}-CHCl_2$ |
| $C_2H_5$ | $CH_3$ | $-\underset{\underset{O}{\|}}{C}-O-CH_3$ |
| $C_2H_5$ | $CH_3$ | $-\underset{\underset{O}{\|}}{C}-OC_2H_5$ |
| $C_2H_5$ | $CH_3$ | $-\underset{\underset{O}{\|}}{C}-O-CH(CH_3)_2$ |
| $-\underset{\underset{O}{\|}}{C}-OCH_3$ | $C_2H_5$ | $C_2H_5$ |

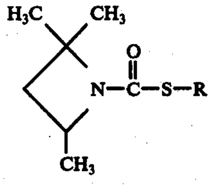

| R |
|---|
| 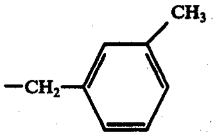 |
| 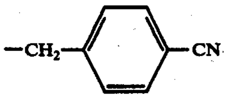 |
| 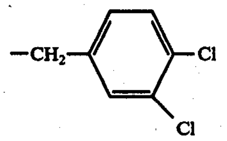 |
| 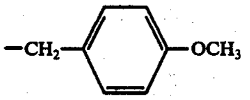 |
| 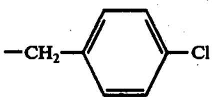 |
| $-CH_2-CCl=CH_2$ |

-continued

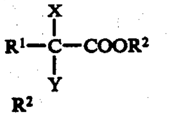

| $R^1$ | $R^2$ | X | Y |
|---|---|---|---|
| Cl | Na | Cl | Cl |
| $CH_3$ | Na | Cl | Cl |
| $CH_2Cl$ | Na | Cl | Cl |
| $CH_3$ | $CH_2-C_6H_5$ | Cl | Cl |
| $C_2H_5$ | Na | Cl | Cl |
| 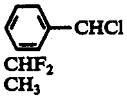 | $NH_4$ | H | Cl |
| $CHF_2$ | Na | F | F |
| $CH_3$ | $CH_2-CH_2Cl$ | Cl | Cl |
| 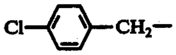 | $CH_3$ | H | Cl |
| 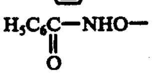 | H | H | H |

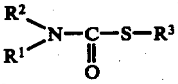

| $R^1$ | $R^2$ | $R^3$ |
|---|---|---|
| i-$C_3H_7$ | i-$C_3H_7$ | $CH_2-CCl=CHCl$ |
| i-$C_3H_7$ | i-$C_3H_7$ | $CH_2-CCl=CCl_2$ |
| n-$C_3H_7$ | n-$C_3H_7$ | $C_2H_5$ |
| i-$C_4H_9$ | i-$C_4H_9$ | $C_2H_5$ |
| n-$C_4H_9$ | $C_2H_5$ | n-$C_3H_7$ |
| n-$C_3H_7$ | n-$C_3H_7$ | n-$C_3H_7$ |
| n-$C_3H_7$ | n-$C_3H_7$ | tert-$C_4H_9$ |
| $C_2H_5$ | $C_2H_5$ | 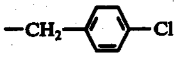 |
| 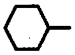 | $C_2H_5$ | $C_2H_5$ |
| 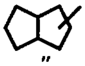 | $C_2H_5$ | $C_2H_5$ |
| " | $C_2H_5$ | $CH_3$ |
| " | $C_2H_5$ | i-$C_3H_7$ |
| 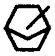 | $C_2H_5$ | $C_2H_5$ |
| 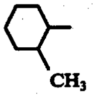 | $C_2H_5$ | $C_2H_5$ |
| 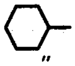 | $CH_2-CH=CH_2$ | $C_2H_5$ |
| " | $CH_2-C\equiv CH$ | $C_2H_5$ |
| " | $CH_2-C\equiv C-CH_3$ | $C_2H_5$ |

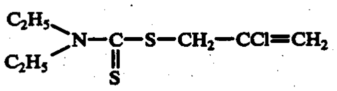

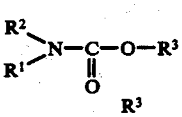

| $R^1$ | $R^2$ | $R^3$ |
|---|---|---|
| $CH_3$ | H | 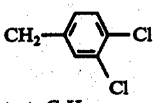 |
| $CH_3$ | H | 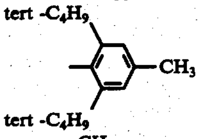 |
| H | 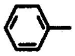 | 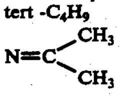 |

-continued

| | | |
|---|---|---|
| H | 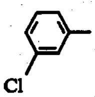 | i-$C_3H_7$ |
| H | 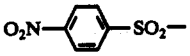 | $CH_3$ |
| H | 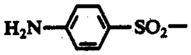 | $CH_3$ |
| H | 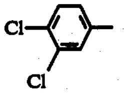 | $CH_3$ |
| H | 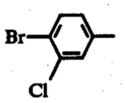 | $CH_3$ |
| H | 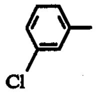 | |
| H | 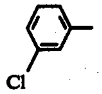 | $CH_2-C\equiv C-CH_2Cl$ |
| H | 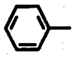 | i-$C_3H_7$ |
| H | 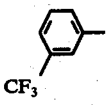 | 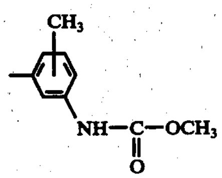 |
| H | 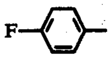 | 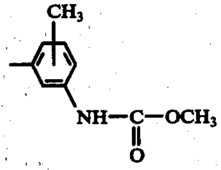 |

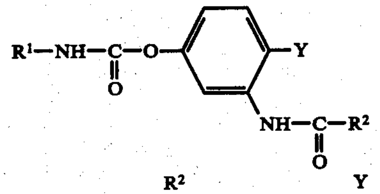

| $R^1$ | $R^2$ | Y |
|---|---|---|
| 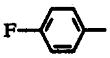 | 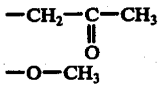 | H |
| 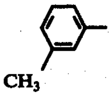 | $-O-CH_3$ | H |
| 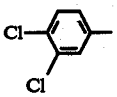 | $-O-CH_3$ | $CH_3$ |
| 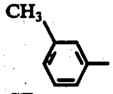 | 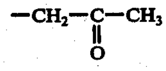 | H |
| 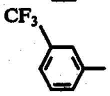 | 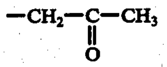 | H |
| 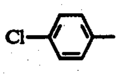 | 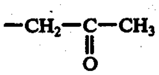 | H |

-continued

| | | |
|---|---|---|
| 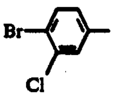 | 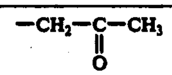 | H |
| 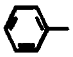 | 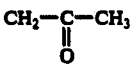 | H |
| 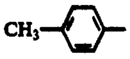 | 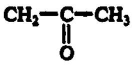 | H |
| 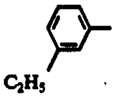 | 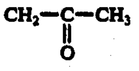 | H |

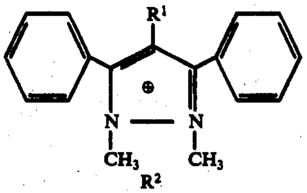 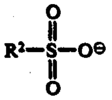

| $R^1$ | $R^2$ |
|---|---|
| H | $OCH_3$ |
| H | 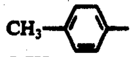 |
| Br | $OCH_3$ |
| $CH_3$ | $OCH_3$ |
| $OCH_3$ | $OCH_3$ |

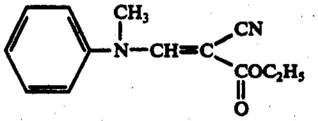

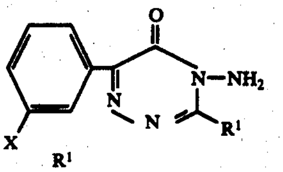

| X | $R^1$ |
|---|---|
| H | $CH_3$ |
| $CH_3$ | $CH_3$ |
| $CF_3$ | $CH_3$ |

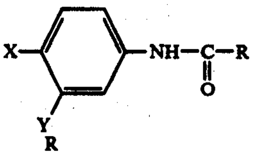

| X | Y | R |
|---|---|---|
| Cl | H | $-C(CH_3)_2-CH_2-CH_2-CH_3$ |
| Cl | Cl | $C_2H_5$ |
| Cl | Cl | $-C(CH_3)=CH_2$ |
| Cl | Cl | $-CH(CH_3)CH_2-CH_2-CH_3$ |
| $CH_3$ | Cl | $-CH(CH_3)-CH_2-CH_2-CH_3$ |

Sulfurous acid esters of glycolic acid amides, azetidine carbothioates and butynyl carbamates may also be used as components in addition to the active ingredients listed above.

The sulfurous acid esters of glycolic acid amides (a) may be obtained by reacting a glycolic acid amide with an alkyl chlorosulfinate at 10° to 15° C in an inert solvent and in the presence of an agent capable of binding hydrogen chloride.

For instance, O-ethyl-O-(1-carbonylmethylazacycloheptane)-sulfite may be prepared by dripping a solution of 12.9 parts by weight of ethyl chlorosulfinate in 50 parts by weight of benzene at 10° to 15° C into 15.7 parts by weight of glycolic acid hexamethylene amide dissolved together with 8 parts by weight of pyridine in 50 parts by weight of dry benzene. After 30 minutes the precipitated pyridinium hydrochloride is filtered off and the organic phase washed with water. After drying has been effected, the benzene is distilled off. There is obtained 20.4 parts by weight of the desired product. The compound has the following structure:

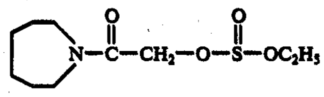

$n_{25} = 1.4910$.

The following active ingredients may for example be used:

N-methylacetanilido-(α-ethylsulfite)
N-methylacetanilido-(α-isopropylsulfite)
N-(butyn-1-yl-3)-acetanilido-(α-ethylsulfite)
N-(butyn-1-yl-3-)acetanilido-(α-isopropylsulfite)
N-(butyn-1-yl-3)-acetanilido-(α-methylsulfite) m.p.: 69° to 70° C
N-isopropylacetanilido-(α-methylsulfite) m.p.: 60° to 61° C
N-ethylacetanilido-(α-propylsulfite) $n_{25}^D$: 1.5295
N-ethylacetanilido-(α-isopropylsulfite) $n_{25}^D$: 1.5164
N-ethylacetanilido-(α-methylsulfite) $n_{25}^D$: 1.5118
N-ethylacetanilido-(α-ethylsulfite) $n_{25}^D$: 1.5010
N-methyl-(4-methoxyacetanilido)-(α-isopropylsulfite)
N-(butyn-1-yl-3)-(4-methoxyacetanilido)-(α-isopropylsulfite)
N-methyl-(p-methylacetanilido)-(α-isopropylsulfite)
N-butyn-1-yl-3)-(p-methylacetanilido)-(α-isopropylsulfite)
N-(2-methylbenzyl)-acetanilido-(α-methylsulfite)
N-(2-methylbenzyl)-acetanilido-(α-ethylsulfite)
N-(2-methylbenzyl)-acetanilido-(α-propylsulfite)
N-(2-methylbenzyl)-acetanilido-(α-isopropylsulfite)
N-tert-butylacetanilido-(α-isopropylsulfite) m.p.: 78° C
N-tert-butylacetanilido-(α-methylsulfite) m.p.: 57° C
N-methylacetanilido-(α-sec-butylsulfite), $n_{25} = 1.5083$
N-(butyn-1-yl-3)-acetanilido-(α-isobutylsulfite) $n_{25}$: 1.5098
N-(butyn-1-yl-3)-acetanilido-(α-sec-butylsulfite) $n_{25}$: 1.5132
N-(butyn-1-yl-3)-acetanilido-(α-n-butylsulfite) $n_{25}$: 1.5172
N-isobutylacetanilido-(α-methylsulfite) $n_{25}$: 1.5229
N-isobutylacetanilido-(α-ethylsulfite) $n_{25}$: 1.5100
N-methylacetanilido-(α-n-butylsulfite) $n_{25}$: 1.5144
N-isobutylacetanilido-(α-propylsulfite) $n_{25}$: 1.5059
N-isobutylacetanilido-(α-isopropylsulfite) $n_{25}$: 1.5028
N-methylacetanilido-(α-methylsulfite)
N-methylacetanilido-(α-isobutylsulfite)
N-(butyn-1-yl-3)-acetanilido-(α-methylsulfite)
N-methyl-(2-methylacetanilido)-(α-methylsulfite)
N-methyl-(4-methylacetanilido)-(α-methylsulfite)
N-methyl-(4-methoxyacetanilido)-(α-methylsulfite)
N-methyl-(3-chloroacetanilido)-(α-methylsulfite)
N-methyl-(2-methylacetanilido)-(α-ethylsulfite)
N-methylacetanilido-[α-(1-methyl-2-methoxy)-ethylsulfite]
N-methyl-(4-methylacetanilido)-(α-ethylsulfite)
N-methyl-(4-methoxyacetanilido)-(α-ethylsulfite)
N-methyl-(3-chloroacetanilido)-(α-ethylsulfite)
N-methyl-(2-methylacetanilido)-(α-isopropylsulfite)
N-methyl-(3-chloroacetanilido)-(α-isopropylsulfite)

N-methyl-(4-methylacetanilido)-(α-n-butylsulfite)
O-methyl-O-(1-carbonylmethylazacycloheptane)-sulfite; $n_{25} = 1.4955$
O-isopropyl-O-(1-carbonylmethylazacycloheptane)-sulfite; $n_{25} = 1.4695$
O-butyl-O-(1-carbonylmethylazacycloheptane)-sulfite; $n_{25} = 1.4875$
O-propyl-O-(1-carbonylmethylazacycloheptane)-sulfite; $n_{25} = 1.4828$
O-isopropyl-O-(1-carbonylmethylazacycloheptane)-sulfite; m.p. = 58° to 59° C
O-ethyl-O-(1-carbonylmethyl-2-methylazacycloheptane)-sulfite; $n_{25} = 1.4882$
O-isopropyl-O-(1-carbonylmethyl-2-methylazacycloheptane)-sulfite; $n_{25} = 1.4740$
O-methyl-O-(1-carbonylmethyl-2,3-dimethylazacycloheptane)-sulfite; $n_{25} = 1.4952$
O-ethyl-O-(1-carbonylmethyl-2,3-dimethylazacycloheptane)-sulfite; $n_{25} = 1.4860$
O-propyl-O-(1-carbonylmethyl-2,3-dimethylazacycloheptane)-sulfite; $n_{25} = 1.4849$
O-isopropyl-O-(1-carbonylmethyl-2,3-dimethylazacycloheptane)-sulfite; $n_{25} = 1.4749$
O-ethyl-O-(1-carbonylmethyl-3,5,5-trimethyl-(3,3,5-trimethyl)-azacycloheptane)-sulfite; $n_{25} = 1.4850$
(1:1 isomer mixture of the 3,3,5- and 3,5,5-trimethyl derivative)
O-isopropyl-O-(1-carbonylmethyl-3-methyl-(2-methyl)-azacycloheptane)-sulfite; $n_{25} = 1.4735$
(isomer mixture, 55% of which being the 3-methyl and 45% of which the 2-methyl derivative)
O-ethyl-O-(1-carbonylmethylazacycloheptane)-sulfite
O-n-propyl-O-(1-carbonylmethylazacycloheptane)-sulfite
O-methyl-O-(1-carbonylmethyl-3-methylazacycloheptane)-sulfite
O-ethyl-O-(1-carbonylmethyl-3-methylazacycloheptane)-sulfite
O-isopropyl-O-(1-carbonylmethyl-3-methylazacycloheptane)-sulfite
O-ethyl-O-(1-carbonylmethyl-4-methylazacycloheptane)-sulfite
O-isopropyl-O-(1-carbonylmethyl-4-methylazacycloheptane)-sulfite
O-methyl-(1-carbonylmethyl-3-azabicyclo-[3,2,0]-heptane)-sulfite
O-ethyl-(1-carbonylmethyl-3-azabicyclo-[3,2,0]-heptane)-sulfite
O-n-propyl-(1-carbonylmethyl-3-azabicyclo-[3,2,0]-heptane)-sulfite
O-isopropyl-(1-carbonylmethyl-3-azabicyclo-[3,2,0]-heptane)-sulfite
O-isopropyl-O-(1-carbonylmethyl-2-methyl-(3-methyl)-azacycloheptane)-sulfite; $n_{25} = 1.4698$
(isomer mixture, 75% of which is the 2-methyl and 25% of which the 3-methyl derivative)
O-allyl-O-(1-carbonylmethyl-2,3-dimethylazacycloheptane)-sulfite $n_{25} = 1.4970$
O-allyl-O-(1-carbonylmethylazacycloheptane)-sulfite; $n_{25} = 1.5026$
O-(butyn-1-yl-3)-O-(1-carbonylmethyl-2,3-dimethylazacycloheptane)-sulfite; $n_{25} = 1.4929$
O-(butyn-1-yl-3)-O-(1-carbonylmethyl-3-methylazacycloheptane)-sulfite; $n_{25} = 1.4965$
O-ethyl-O-(1-carbonylmethylazacyclohexane)-sulfite
O-isopropyl-O-(1-carbonylmethylazacyclohexane)-sulfite
O-methyl-O-(1-carbonylmethyl-2-methylazacyclohexane)-sulfite
O-allyl-O-(1-carbonylmethyl-2-methylazacycohexane)-sulfite
O-isopropyl-O-(1-carbonylmethyl-2-methylazacyclohexane)-sulfite
O-isopropyl-O-(1-carbonylmethyl-3-methylazacyclohexane)-sulfite
O-(β-chloroethyl)-O-(1-carbonylmethyl-3-methylazacyclohexane)-sulfite
O-ethyl-O-(1-carbonylmethyl-4-methylazacyclohexane)-sulfite
O-allyl-O-(1-carbonylmethyl-4-methylazacyclohexane)-sulfite
O-(β-chloroethyl)-O-(1-carbonylmethyl-4-methylazacyclohexane)-sulfite
O-methyl-O-(1-carbonylmethyl-3,3-dimethylazacyclohexane)-sulfite
O-isopropyl-O-(1-carbonylmethyl-3,3-dimethylazacyclohexane)-sulfite
O-(β-chloroethyl)-O-(1-carbonylmethyl-3,5,5-trimethyl)-(3,3,5-trimethylazacycloheptane)-sulfite
(1:1 isomer mixture of the 3,5,5- and the 3,3,5-trimethyl derivative).

The azetidine carbothioates may be prepared by reaction of a thiol chloroformate with an optionally substituted azetidine. The active ingredients may also be prepared by reaction of an azetidine in the form of its N-acyl chloride with a mercaptan.

For instance, S-ethyl-(2,2,4-trimethylazetidine)-1-carbothioate may be obtained by dripping 6.23 parts by weight of thioethyl chloroformate at 30° to 40° C into a mixture of 4.95 parts by weight of 2,2,4-trimethylazetidine and 6 parts by weight of triethylamine in 50 parts by weight of benzene. After 1 hour the triethylamine hydrochloride is filtered off and the filtrate washed with water. After drying has been effected, concentration is carried out in vacuo and the residue distilled off. There is obtained 6.7 parts by weight of the desired compound, which has the following structural formula:

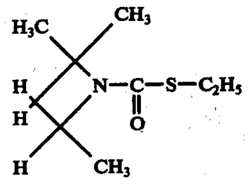

b.p. (0.01 mm) = 59° C

The following azetidine carbothioates may for example be used as herbicidally active ingredients:

S-methyl-(2,2,4-trimethylazetidine)-1-carbothioate, b.p. (0.05 mm): 70° C
S-propyl-(2,2,4-trimethylazetidine)-1-carbothioate, b.p. (0.05 mm): 81° C
S-isopropyl-(2,2,4-trimethylazetidine)-1-carbothioate, b.p. (0.01 mm): 67° to 71° C
S-sec-butyl-(2,2,4-trimethylazetidine)-1-carbothioate, b.p. (0.01 mm): 75° to 80° C
S-trichloroallyl-(2,2,4-trimethylazetidine)-1-carbothioate, b.p. (0.01 mm): 130° C
S-benzyl-(2,2,4-trimethylazetidine)-1-carbothioate, b.p. (0.01 mm): 135° C
S-(p-chlorobenzyl)-2,2,4-trimethylazetidine)-1-carbothioate, b.p. (0.05 mm): 154° C S-benzyl-(3,3-dimethylazetidine)-1-carbothioate, b.p. (0.01 mm): 128° C S-(β-phenylethyl)-(2,2,4-trimethylazetidine)-1-carbothioate, b.p. (0.01 mm): 120° to 125° C, $n_{20}$: 1.5398

S-(β-phenylethyl)-(3,3-dimethylazetidine)-1-carbothioate, b.p. (0.01 mm): 140° to 145° C, $n_{20}$ = 1.5996

S-benzyl-(2,2,4-trimethylazetidine)-1-thiocarbothioate, b.p. (0.01 mm): 160° C, $n_{25}$ = 1.6026

S-propyl-(2,2,4-trimethylazetidine)-1-thiocarbothioate, b.p. (0.01 mm): 100° C, $n_{25}$ = 1.5540

S-benzylacetidine-1-carbothioate

S-ethylazetidine-1-carbothioate

S-propylazetidine-1-carbothioate

S-isopropylacetidine-1-carbothioate

S-benzyl-(2-methylazetidine)-1-carbothioate

S-butyl-(2,2,4-trimethylazetidine)-1-carbothioate b.p. (0.01 mm) = 90° to 95° C, $n_{20}$ = 1.4835

S-propyl-(2,2,4-trimethylazetidine)-1-thiocarbothioate

S-2,3-dichloroallyl-(2,2,4-trimethylazetidine)-1-carbothiolate

S-4-methoxybenzyl-(2,2,4-trimethylazetidine)-1-carbothiolate

A component may make up from 5 to 95 wt%, preferably 20 to 80 wt%, of an active ingredient composition according to the invention.

The amount used of the agents according to the invention may vary and depends in essence on the type of effect to be achieved; it is generally from 0.1 to 15 (and more), preferably from 0.2 to 6, kg per hectare of active ingredient. The agents according to the invention may be used once or several times before or after planting, before sowing, and before, during or after emergence of the crop plant and unwanted plants.

Application may be effected for instance in the form of directly sprayable solutions, powders, suspensions, (including high-percentage oily or aqueous suspensions) dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfonated hexadecanols, heptadecanols, and octadecanols, salts of sulfonated fatty alcohols glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silica gel, silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and urea, and vegetable products such as grain flours, bark meal, wood meal, and nutshell meal, cellulocis powders, etc.

The formulations contain from 0.1 to 95, and preferably 0.5 to 90, % by weight of active ingredient.

There may be added to the compositions or individual active ingredients (if desired, immediately before use (tankmix)) oils of various types, wetting agents or adherents, herbicides, fungicides, nematocides, insecticides, bactericides, trace elements, fertilizers, antifoams (e.g., silicones), growth regulators, antidotes and other herbicidally effective compounds such as substituted anilines substituted aryloxycarboxylic acids and salts, esters and amides thereof, substituted ethers substituted arsonic acids and their salts, esters and amides substituted benzimidazoles substituted benzisothiazoles substituted benzothiadiazinone dioxides substituted benzoxazines substituted benzoxazinones substituted benzothiadiazoles substituted biurets substituted quinolines substituted carbamates substituted aliphatic carboxylic acids and their salts, esters and amides substituted aromatic carboxylic acids and their salts, esters and amides substituted carbamoylalkylthiol- or -dithiophosphates substituted quinazolines substituted cycloalkylamidocarbothiolic acids and their salts, esters and amides substituted cycloalkylcarbonamidothiazoles substituted dicarboxylic acids and their salts, esters and amides substituted dihydrobenzofuranyl sulfonates
substituted disulfides
substituted dipyridylium salts
substituted dithiocarbamates
substituted dithiophosphoric acids and their salts, esters and amides
substituted ureas
substituted hexahydro-1H-carbothioates
substituted hydantoins
substituted hydrazides
substituted hydrazonium salts
substituted isoxazole pyrimidones
substituted imidazoles
substituted isothiazole pyrimidones
substituted ketones
substituted naphthoquinones
substituted aliphatic nitriles
substituted aromatic nitriles
substituted oxadiazoles
substituted oxadiazinones
substituted oxadiazolidine diones
substituted oxadiazine diones
substituted phenols and their salts and esters
substituted phosphonic acids and their salts, esters and amides
substituted phosphonium chlorides
substituted phosphonalkyl glycines
substituted phosphites
substituted phosphoric acids and their salts, esters and amides
substitutes piperidines
substituted pyrazoles
substituted pyrazole alkylcarboxylic acids and their salts, esters and amides
substituted pyrazolium salts
substituted pyrazolium alkyl sulfates
substituted pyridazines
substituted pyridazones
substituted pyridine carboxylic acids and their salts, esters and amides
substituted pyridines
substituted pyridine carboxylates
substituted pyridinones
substituted pyrimidines
substituted pyrimidones
substituted pyrrolidine carboxylic acid and its salts, esters and amides
substituted pyrrolidines
substituted pyrrolidones
substituted arylsulfonic acids and their salts, esters and amides
substituted styrenes
substituted tetrahydrooxadiazine diones
substituted tetrahydroxadiazole diones
substituted tetrahydromethanoindenes
substituted tetrahydroxadiazole thiones
substituted tetrahydrothiadiazine thiones
substituted tetrahydrothiadiazole diones
substituted aromatic thiocarbonylamides
substituted thiocarboxylic acids and their salts, esters and amides
substituted thiol carbamates
substituted thioureas
substituted thiophosphoric acids and their salts, esters and amides
substituted triazines
substituted triazoles
substituted uracils, and
substituted uretidine diones.

The last-mentioned herbicidal compounds may also be applied before or after the compositions according to the invention.

These agents may be added to the compositions according to the invention in a ratio by weight of from 1:10 to 10:1. The same applies to oils, fungicides, nematocides, insecticides, bactericides, antidotes and growth regulators.

The new compositions have a strong herbicidal action and may therefore be used as weedkillers or for controlling the growth of unwanted plants. Whether the new active ingredients are used as total or selective agents depends in essence on the amount of ingredient used per unit area.

By weeds and unwanted plant growth are meant all monocotyledonous and dicotyledonous plants which grow in loci where they are not desired.

The agents according to the invention may therefore be used for controlling for instance

| | |
|---|---|
| *Gramineae*, such as | |
| *Cynodon* spp. | *Dactylis* spp. |
| *Digitaria* spp. | *Avena* spp. |
| *Echinochloa* spp. | *Bromus* spp. |
| *Setaria* spp. | *Uniola* spp. |
| *Panicum* spp. | *Poa* spp. |
| *Alopecurus* spp. | *Leptochloa* spp. |
| *Lolium* spp. | *Brachiaria* spp. |
| *Sorghum* spp. | *Eleusine* spp. |
| *Agropyron* spp. | *Cenchrus* spp. |
| *Phalaris* spp. | *Eragrostis* spp. |
| *Apera* spp. | *Phragmites communis* |
| etc.; | |
| *Cyperaceae*, such as | |
| *Carex* spp. | *Eleocharis* spp. |
| *Cyperus* spp. | *Scirpus* spp. |
| etc.; | |
| dicotyledonous weeds, such as | |
| *Malvaceae*, e.g. | |
| *Abutilon theoprasti* | *Hibiscus* spp. |
| *Sida* spp. | *Malva* spp. |
| etc.; | |
| *Compositae*, such as | |
| *Ambrosia* spp. | *Centaurea* spp. |
| *Lactuca* spp. | *Tussilago* spp. |
| *Senecio* spp. | *Lapsana communis* |
| *Sonchus* spp. | *Tagetes* spp. |
| *Xanthium* spp. | *Erigeron* spp. |
| *Iva* spp. | *Anthemis* spp. |
| *Galinsoga* spp. | *Matricaria* spp. |
| *Taraxacum* spp. | *Artemisia* spp. |
| *Chrysanthemum* spp. | *Bidens* spp. |
| *Cirsium* spp. | etc.; |
| *Convolvulaceae*, such as | |
| *Convolvulus* spp. | *Cuscuta* spp. |
| *Ipomoea* spp. | *Jaquemontia tamnifolia* |
| etc.; | |
| *Cruciferae*, such as | |
| *Barbarea vulgaris* | *Arabidopsis thaliana* |
| *Brassica* spp. | *Descurainia* spp. |
| *Capsella* spp. | *Draba* spp. |
| *Sisymbrium* spp. | *Coronopus didymus* |
| *Thlaspi* spp. | *Lepidium* spp. |
| *Sinapis arvensis* | *Raphanus* spp. |
| etc.; | |
| *Geraniaceae*, such as | |
| *Erodium* spp. | *Geranium* spp. |
| etc.; | |
| *Portulacaceae*, such as | |
| *Portulaca* spp. | etc.; |
| *Primalaceae*, such as | |
| *Anagallis arvensis* | *Lysimachia* spp. |
| etc.; | |
| *Rubiaceae*, such as | |
| *Richardia* spp. | *Diodia* spp. |
| *Galium* spp. | etc.; |
| *Scrophulariacea*, such as | |
| *Linaria* spp. | *Digitalis* spp. |
| *Veronica* spp. | etc.; |
| *Solanaceae*, such as | |
| *Physalis* spp. | *Nicandra* spp. |
| *Solanum* spp. | *Datura* spp. |
| etc.; | |
| *Urticaceae*, such as | |
| *Urtica* spp. | |

-continued

| | |
|---|---|
| *Violaceae*, such as | |
| *Viola* spp. | etc.; |
| *Zygophyllaceae*, such as | |
| *Tribulus terrestris* | etc.; |
| *Euphorbiaceae*, such as | |
| *Mercurialis annua* | *Euphorbia* spp. |
| *Umbelliferae*, such as | |
| *Daucus carota* | *Ammi majus* |
| *Aethusa cynapium* | etc.; |
| *Commelinaceae*, such as | |
| *Commelina* spp. | etc.; |
| *Labiatae*, such as | |
| *Lamium* spp. | *Galeopsis* spp. |
| etc.; | |
| *Leguminosae*, such as | |
| *Medicago* spp. | *Sesbania exaltata* |
| *Trifolium* spp. | *Cassia* spp. |
| *Vicia* spp. | *Lathyrus* spp. |
| etc.; | |
| *Plantaginaceae*, such as | |
| *Plantago* spp. | etc.; |
| *Polygonaceae*, such as | |
| *Polygonum* spp. | *Fagopyrum* spp. |
| *Rumex* spp. | etc.; |
| *Aizoaceae*, such as | |
| *Mollugo verticillata* | etc.; |
| *Amaranthaceae*, such as | |
| *Amaranthus* spp. | etc.; |
| *Boraginaceae*, such as | |
| *Amsinckia* spp. | *Anchusa* spp. |
| *Myostis* spp. | *Lithospermum* spp. |
| etc.; | |
| *Caryophyllaceae*, such as | |
| *Stellaria* spp. | *Silene* spp. |
| *Spergula* spp. | *Cerastium* spp. |
| *Saponaria* spp. | *Agrostemma githago* |
| *Scleranthus annuus* | etc.; |
| *Chenopodiaceae*, such as | |
| *Chenopodium* spp. | *Atriplex* spp. |
| *Kochia* spp. | *Monolepsis nuttalliana* |
| *Salsola Kali* | etc.; |
| *Lythraceae*, such as | |
| *Cuphea* spp. | etc.; |
| *Oxalidaceae*, such as | |
| *Oxalis* spp. | |
| *Ranunculaceae*, such as | |
| *Ranunculus* spp. | *Adonis* spp. |
| *Delphinium* spp. | etc.; |
| *Papaveraceae*, such as | |
| *Papaver* spp. | *Fumaria offinicalis* |
| etc.; | |
| *Onagraceae*, such as | |
| *Jussiaea* spp. | etc.; |
| *Rosaceae*, such as | |
| *Alchemillia* spp. | *Potentilla* spp. |
| etc.; | |
| *Potamogetonaceae*, such as | |
| *Potamogeton* spp. | etc.; |
| *Najadaceae*, such as | |
| *Najas* spp. | etc.; |
| *Equisetaceae* | |
| *Equisetum* spp. | etc.; |
| *Marsileaceae*, such as | |
| *Marsilea quadrifolia* | etc.; |
| *Polypodiaceae*, | |
| *Pteridium quilinum* | |
| *Alismataceae*, such as | |
| *Alisma* spp. | *Sagittaria sagittifolia* |
| etc. | |
| The herbicides according to the invention may be employed in cereal crops such as | |
| *Avena* spp. | *Sorghum* |
| *Triticum* spp. | *Zea mays* |
| *Hordeum* spp. | *Panicum miliaceum* |

-continued

| | |
|---|---|
| *Secale* spp. | *Oryza* spp. |
| *Saccharum offinicarum* | |
| and in dicotyledon crops such as | |
| *Cruciferae*, e.g. | |
| *Brassica* spp. | *Raphanus* spp. |
| *Sinapis* spp. | *Lepidium* spp. |
| *Compositae*, e.g. | |
| *Lactuca* spp. | *Carthamus* spp. |
| *Helianthus* spp. | *Scorzonera* spp. |
| *Malvaceae*, e.g. | |
| *Gossypium hirsutum* | |
| *Leguminosae*, e.g. | |
| *Medicago* spp. | *Phaseolus* spp. |
| *Trifolium* spp. | *Arachis* spp. |
| *Pisum* spp. | *Glycine max.* |
| *Chenopodiaceae*, e.g. | |
| *Beta vulgaris* | |
| *Spinacia* spp. | |
| *Solanaceae*, e.g. | |
| *Solanum* spp. | *Capsicum annuum* |
| *Nicotiania* spp. | |
| *Linaceae*, e.g. | |
| *Linum* spp. | |
| *Umbelliferae*, e.g. | |
| *Petroselinum* spp. | *Apium graveolens* |
| *Daucus carota* | |
| *Rosaceae*, e.g. | *Fragaria* |
| *Cucurbitaceae* e.g. | |
| *Cucumis* spp. | *Cucurbita* spp. |
| *Liliaceae*, e.g. | |
| *Allium* spp. | |
| *Vitaceae*, e.g. | |
| *Vitis vinifera* | |
| *Bromeliaceae*, e.g. | |
| *Ananas sativus.* | |

The compositions may also be used as total agents on ditches, aquatic areas, railway track, waste and barren land, etc.

The compositions according to the invention were tested in the greenhouse and in the open. Their action corresponds to that of the compositions employed in the following examples.

EXAMPLE 1

In the greenhouse, loamy sandy soil was filled into pots and sown with various seeds. The soil prepared in this manner was then treated with the following amounts of the following individual compounds and compositions thereof as emulsions or dispersions:

I: 1-phenyl-4-amino-5-chloropyradazone-(6)

II: O-(isopropylaminosulfonyl)-glycolic acid-N-butyn-1-yl-3-anilide

III: O-(methylaminosulfonyl)-glycolic acid-N-isopropylanilide, each at rates of 0.25, 0.75 and 1 kg/ha;

I+II, I+III, each at rates of 0.25+0.75, 0.75+0.25 and 0.5+0.5 kg/ha.

After 4 to 5 weeks it was ascertained that the compositions had a better herbicidal action than their components, combined with the same crop plant compatibility. The results are given below:

| Active ingredient | I | | | | II | | | | III | | | |
|---|---|---|---|---|---|---|---|---|---|---|---|---|
| kg/ha | 0.25 | 0.5 | 0.75 | 1 | 0.25 | 0.5 | 0.75 | 1 | 0.25 | 0.5 | 0.75 | 1 |
| Crop plants: | | | | | | | | | | | | |
| *Beta vulgaris* | 0 | 0 | 0 | 0 | 0 | 0 | 0 | 0 | 0 | 0 | 0 | 0 |
| *Beta vulgaris* var. *altissima* | 0 | 0 | 0 | 0 | 0 | 0 | 0 | 0 | 0 | 0 | 0 | 0 |
| *Beta vulgaris* var. *conditiva* | 0 | 0 | 0 | 0 | 0 | 0 | 0 | 0 | 0 | 0 | 0 | 0 |
| Unwanted plants: | | | | | | | | | | | | |
| *Avena fatua* | 0 | 5 | 8 | 12 | 30 | 40 | 55 | 60 | 10 | 15 | 30 | 40 |
| *Sinapis arvensis* | 15 | 20 | 25 | 30 | 5 | 10 | 15 | 20 | 3 | 10 | 15 | 20 |
| *Galium aparine* | 10 | 15 | 30 | 40 | 0 | 10 | 15 | 20 | 0 | 10 | 12 | 15 |
| *Echinochloa crus-galli* | 5 | 6 | 10 | 13 | 50 | 60 | 65 | 70 | 20 | 25 | 45 | 70 |

| Active ingredient | I + II | | | I + III | | |
|---|---|---|---|---|---|---|
| kg/ha | 0.25 + 0.75 | 0.75 + 0.25 | 0.5 + 0.5 | 0.25 + 0.75 | 0.75 + 0.25 | 0.5 + 0.5 |

-continued

| | | | | | | |
|---|---|---|---|---|---|---|
| Beta vulgaris | 0 | 0 | 0 | 0 | 0 | 0 |
| Beta vulgaris var. altissima | 0 | 0 | 0 | 0 | 0 | 0 |
| Beta vulgaris var. conditiva | 0 | 0 | 0 | 0 | 0 | 0 |
| Avena fatua | 90 | 70 | 85 | 75 | 60 | 65 |
| Sinapis arvensis | 70 | 70 | 68 | 67 | 70 | 69 |
| Galium aparine | 65 | 70 | 65 | 60 | 70 | 65 |
| Echinochloa crus-galli | 100 | 100 | 100 | 97 | 95 | 97 |

0 = no damage
100 = complete destruction

EXAMPLE 2 bility than the compositions I+X, combined with the same herbicidal action.

| Active ingredient | I | | | | | | | II | | | | | | |
|---|---|---|---|---|---|---|---|---|---|---|---|---|---|---|
| kg/ha | 1 | 1.5 | 2 | 2.5 | 3 | 4 | 5 | 1 | 1.5 | 2 | 2.5 | 3 | 4 | 5 |
| Crop plants: | | | | | | | | | | | | | | |
| Beta vulgaris | 0 | 0 | 0 | 0 | 0 | 10 | 15 | 0 | 0 | 0 | 0 | 5 | 10 | 25 |
| Unwanted plants: | | | | | | | | | | | | | | |
| Avena fatua | 12 | 15 | 20 | 25 | 40 | 75 | 90 | 60 | 65 | 75 | 80 | 85 | 90 | 95 |
| Sinapis arvensis | 30 | 50 | 70 | 75 | 80 | 90 | 100 | 20 | 25 | 30 | 35 | 45 | 55 | 60 |
| Galium aparine | 40 | 50 | 75 | 80 | 85 | 90 | 95 | 20 | 35 | 50 | 55 | 60 | 65 | 75 |
| Echinochloa crus-galli | 13 | 20 | 32 | 50 | 65 | 75 | 90 | 70 | 95 | 100 | 100 | 100 | 100 | 100 |

| Active ingredient | III | | | | | | |
|---|---|---|---|---|---|---|---|
| Beta vulgaris | 0 | 0 | 0 | 0 | 0 | 10 | 20 |
| Avena fatua | 40 | 45 | 54 | 70 | 75 | 80 | 90 |
| Sinapis arvensis | 20 | 30 | 35 | 40 | 45 | 50 | 55 |
| Galium aparine | 15 | 25 | 30 | 35 | 40 | 43 | 45 |
| Echinochloa crus-galli | 70 | 90 | 100 | 100 | 100 | 100 | 100 |

| Active ingredient | I + II | | | | | | | | X | |
|---|---|---|---|---|---|---|---|---|---|---|
| kg/ha | 2+1 | 1+2 | 1.5+1.5 | 3+1 | 1+3 | 2+2 | 2.5+1.5 | 3+2 | 3 | 4 |
| Crop plants: | | | | | | | | | | |
| Beta vulgaris | 0 | 0 | 0 | 0 | 5 | 0 | 0 | 0 | 100 | 100 |
| Unwanted plants: | | | | | | | | | | |
| Avena fatua | 100 | 100 | 100 | 100 | 100 | 100 | 100 | 100 | 100 | 100 |
| Sinapis arvensis | 100 | 100 | 100 | 100 | 100 | 100 | 100 | 100 | 100 | 100 |
| Galium aparine | 100 | 100 | 100 | 100 | 100 | 100 | 100 | 100 | 100 | 100 |
| Echinochloa crus-galli | 100 | 100 | 100 | 100 | 100 | 100 | 100 | 100 | 100 | 100 |

| Active ingredient | I + III | | | | | | | | I+X (1+3 kg/ha) |
|---|---|---|---|---|---|---|---|---|---|
| Beta vulgaris | 0 | 0 | 0 | 0 | 0 | 0 | 0 | 0 | 100 |
| Avena fatua | 100 | 100 | 100 | 100 | 100 | 100 | 100 | 100 | 100 |
| Sinapis arvensis | 100 | 100 | 100 | 100 | 100 | 100 | 100 | 100 | 100 |
| Galium aparine | 100 | 100 | 100 | 100 | 100 | 100 | 100 | 100 | 100 |
| Echinochloa crus-galli | 100 | 100 | 100 | 100 | 100 | 100 | 100 | 100 | 100 |

0 = no damage
100 = complete destruction

In the greenhouse, loamy sandy soil was filled into pots and sown with various seeds. The soil prepared in this manner was then treated with the following amounts of the following individual compounds and compositions thereof as emulsions or dispersions:

I: 1-phenyl-4-amino-5-chloropyradazone-(6)
II: O-(isopropylaminosulfonyl)-glycolic acid-N-butyn-1-yl-3-anilide
O-(methylaminosulfonyl)-glycolic acid-N-isopropylanilide,
each at rates of 1, 1.5, 2, 2.5, 3, 4 and 5 kg/ha;
I+II, I+III, each at rates of 2+1, 1+2, 1.5+1.5, 1+3, 3+1, 2+2, 2.5+1.5 and 3+2 kg/ha;
and
X: N-(4-chlorophenyl)-N',N-dimethylurea (comparative agent), 3 and 4 kg/ha;
I+X 1+3 kg/ha.

After 4 to 5 weeks it was ascertained that the compositions I+II and I+III had better crop plant compati-

EXAMPLE 3

In the open, various plants were treated at a growth height of from 4 to 17 cm with the following amounts of the following individual active ingredients and compositions thereof as suspensions or dispersions:

I: 1-phenyl-4-amino-5-chloropyridazone-(6)
II: O-(isopropylaminosufonyl)-glycolic acid-N-butyn-1-yl-3-anilide
III: O-(methylaminosulfonyl)-glycolic acid-N-isopropylanilide,
each at rates of 0.25, 0.5, 0.75 and 1 kg/ha;
I'II and I+III, each at rates of 0.25+0.75, 0.75+0.25 and 0.5+0.5 kg/ha,
and additionally 2 l/ha of a spreader (adduct of 6 to 7 moles of ethylene oxide to 1 mole of isooctylphenol).

After 2 to 3 weeks it was ascertained that the compositions had a better herbicidal action than their components, combined with the same crop plant compatibility.

The results are given below:

| Active ingredient | I + spreader | II + spreader | III + spreader |
|---|---|---|---|

-continued

| kg/ha or l/ha | 0.25+ 2.0 | 0.5+ 2.0 | 0.75+ 2.0 | 1+ 2.0 | 0.25+ 2.0 | 0.5+ 2.0 | 0.75+ 2.0 | 1+ 2.0 | 0.25+ 2.0 | 0.5+ 2.0 | 0.75+ 2.0 | 1+ 2.0 |
|---|---|---|---|---|---|---|---|---|---|---|---|---|
| Crop plants: | | | | | | | | | | | | |
| *Beta vulgaris* | 0 | 0 | 0 | 0 | 0 | 0 | 0 | 0 | 0 | 0 | 0 | 0 |
| *Beta vulgaris* var. *altissima* | 0 | 0 | 0 | 0 | 0 | 0 | 0 | 0 | 0 | 0 | 0 | 0 |
| *Beta vulgaris* var. *conditiva* | 0 | 0 | 0 | 0 | 0 | 0 | 0 | 0 | 0 | 0 | 0 | 0 |
| Unwanted plants: | | | | | | | | | | | | |
| *Avena fatua* | 3 | 5 | 8 | 13 | 20 | 30 | 45 | 50 | 15 | 25 | 45 | 50 |
| *Sinapis arvensis* | 20 | 30 | 33 | 35 | 10 | 20 | 25 | 30 | 10 | 25 | 30 | 45 |
| *Galium aparine* | 10 | 20 | 30 | 40 | 5 | 10 | 15 | 20 | 5 | 15 | 20 | 25 |
| *Echinochloa crus-galli* | 10 | 15 | 19 | 25 | 30 | 45 | 65 | 70 | 30 | 45 | 65 | 70 |

| | I + II + spreader | | | I + III + spreader | | |
|---|---|---|---|---|---|---|
| Active ingredient kg/ha or l/ha | 0.25+ 0.75+ 2.0 | 0.75+ 0.25+ 2.0 | 0.5+ 0.5+ 2.0 | 0.25+ 0.75+ 2.0 | 0.75+ 0.25+ 2.0 | 0.5+ 0.5+ 2.0 |
| Crop plants: | | | | | | |
| *Beta vulgaris* | 0 | 0 | 0 | 0 | 0 | 0 |
| *Beta vulgaris* var. *altissima* | 0 | 0 | 0 | 0 | 0 | 0 |
| *Beta vulgaris* var. *conditiva* | 0 | 0 | 0 | 0 | 0 | 0 |
| Unwanted plants: | | | | | | |
| *Avena fatua* | 90 | 70 | 70 | 90 | 65 | 68 |
| *Sinapis arvensis* | 90 | 81 | 91 | 86 | 79 | 83 |
| *Galium aparine* | 63 | 70 | 80 | 70 | 70 | 75 |
| *Echinochloa crus-galli* | 100 | 90 | 95 | 100 | 90 | 95 |

0 = no damage
100 = complete destruction

EXAMPLE 4

In the open, various plants were treated at a growth height of from 2 to 18 cm with the following amounts of the following individual active ingredients and compositions thereof, each being emulsified or dispersed in 500 liters of water per hectare:

I 1-phenyl-4-amino-5-chloropyridazone-(6)

II: O-(isopropylaminosulfonyl)-glycolic acid-N-butyn-1-yl-3-anilide

III: O-(methylaminosulfonyl)-glycolic acid-N-isopropylanilide, each at rates of 1, 1.5, 2, 2.5, 3, 4 and 5 kg/ha;

I+II and I+III, each at rates of 2+1, 1+2, 1.5+1.5, 3+1, 1+3, 2+2, 2.5+1.5 and 3+2 kg/ha;

and for comparison

X: N-(4-chlorophenyl)-N',N'-dimethylurea, 3 and 4 kg/ha;

I+X: 1+3 kg/ha.

After 2 to 3 weeks it was ascertained the compositions I+II and I+III had better crop tolerance than the composition I+X, combined with the same herbicidal action.

The results are given below:

| Active ingredient | I | | | | | | | II | | | | | | |
|---|---|---|---|---|---|---|---|---|---|---|---|---|---|---|
| kg/ha | 1 | 1.5 | 2 | 2.5 | 3 | 4 | 5 | 1 | 1.5 | 2 | 2.5 | 3 | 4 | 5 |
| Crop plants: | | | | | | | | | | | | | | |
| *Beta vulgaris* | 0 | 0 | 0 | 0 | 0 | 10 | 20 | 0 | 0 | 0 | 0 | 0 | 10 | 15 |
| Unwanted plants: | | | | | | | | | | | | | | |
| *Avena fatua* | 13 | 15 | 25 | 35 | 40 | 65 | 90 | 50 | 55 | 60 | 63 | 65 | 70 | 80 |
| *Sinapis arvensis* | 35 | 44 | 50 | 60 | 85 | 100 | 100 | 15 | 25 | 30 | 44 | 47 | 50 | 55 |
| *Galium aparine* | 40 | 50 | 70 | 75 | 80 | 90 | 100 | 10 | 24 | 28 | 35 | 40 | 46 | 50 |
| *Echinochloa crus-galli* | 25 | 40 | 53 | 70 | 80 | 90 | 100 | 70 | 78 | 80 | 90 | 95 | 100 | 100 |

| Active ingredient | III | | | | | | |
|---|---|---|---|---|---|---|---|
| *Beta vulgaris* | 0 | 0 | 0 | 0 | 0 | 10 | 14 |
| *Avena fatua* | 50 | 60 | 65 | 68 | 70 | 72 | 75 |
| *Sinapis arvensis* | 20 | 30 | 33 | 40 | 45 | 50 | 60 |
| *Galium aparine* | 25 | 27 | 30 | 35 | 41 | 45 | 50 |
| *Echinochloa crus-galli* | 70 | 75 | 80 | 85 | 90 | 100 | 100 |

| Active ingredient | I + II | | | | | | | | X | |
|---|---|---|---|---|---|---|---|---|---|---|
| kg/ha | 2+1 | 1+2 | 1.5+ 1.5+ | 3+1 | 1+3 | 2+2 | 2.5+ 1.5 | 3+2 | 3 | 4 |
| Crop plants: | | | | | | | | | | |
| *Beta vulgaris* | 0 | 0 | 0 | 0 | 0 | 0 | 0 | 0 | 100 | 100 |
| Unwanted plants: | | | | | | | | | | |
| *Avena fatua* | 100 | 100 | 100 | 100 | 100 | 100 | 100 | 100 | 95 | 100 |
| *Sinapis arvensis* | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 |

| Active ingredient | I + III | | | | | | | | I + X 1+3 kg/ha |
|---|---|---|---|---|---|---|---|---|---|
| *Beta vulgaris* | 0 | 0 | 0 | 0 | 0 | 0 | 0 | 0 | 100 |

-continued

| | | | | | | | | | |
|---|---|---|---|---|---|---|---|---|---|
| *Avena fatua* | 100 | 100 | 100 | 100 | 100 | 100 | 100 | 100 | 100 |
| *Sinapis arvensis* | 100 | 100 | 100 | 100 | 100 | 100 | 100 | 100 | 100 |
| *Galium aparine* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |

0 = no damage
100 = complete destruction

EXAMPLE 5

An agricultural plot was sown with various seeds. The soil was then immediately treated with the following amounts of the following individual active ingredients and compositions thereof as dispersions, emulsions or granules:

I: 1-phenyl-4-amino-5-chloropyradazone-(6)
III: O-(methylaminosulfonyl)-glycolic acid-N-isopropylanilide
IV: 2,3-dichloroallyl N,N-diisopropylthiocarbamate
V: 2,3,3-trichloroallyl N,N-diisopropylthiolcarbamate
VI: 2-ethoxy-2,3-dihydro-3,3-dimethyl-5-benzofuranylmethane sulfonate
VIII: 2,3-dihydro-3,3-dimethyl-2-ethoxybenzofuran-5-yldimethylamino sulfonate
IX: ethyl N-ethyl-N-cyclohexylthiolcarbamate,
each at rates of 0.5, 1 and 2 kg/ha;
I+III+IV, I+III+V, I+III+VI, I+III+VIII and I+III+IX,
each at rates of 1.0.5+0.5, 0.5+1+0.5 and 0.5+0.5+1 kg/ha.

After 4 to 5 weeks it was ascertained that the compositions had a better herbicidal action than their components, combined with the same crop tolerance.

The results are given below:

| Active ingredient kg/ha | I 0.5 | I 1 | I 2 | III 0.5 | III 1 | III 2 | IV 0.5 | IV 1 | IV 2 |
|---|---|---|---|---|---|---|---|---|---|
| Crop plants: | | | | | | | | | |
| *Beta vulgaris* | 0 | 0 | 0 | 0 | 0 | 0 | 0 | 0 | 10 |
| Unwanted plants: | | | | | | | | | |
| *Avena fatua* | 5 | 12 | 20 | 15 | 40 | 54 | 20 | 50 | 95 |
| *Echinochloa crus-galli* | 6 | 13 | 32 | 25 | 70 | 100 | 10 | 20 | 50 |
| *Matricaria chamomilla* | 20 | 40 | 85 | 15 | 35 | 80 | 5 | 10 | 19 |

| Active ingredient kg/ha | V 0.5 | V 1 | V 2 | VI 0.5 | VI 1 | VI 2 | VIII 0.5 | VIII 1 | VIII 2 | IX 0.5 | IX 1 | IX 2 |
|---|---|---|---|---|---|---|---|---|---|---|---|---|
| *Beta vulgaris* | 0 | 0 | 0 | 2.5 | 4 | 10 | 0 | 0 | 0 | 0 | 0 | 0 |
| *Avena fatua* | 25 | 50 | 95 | 16 | 40 | 80 | 45 | 80 | 100 | 10 | 30 | 60 |
| *Echinochloa crus-galli* | 10 | 20 | 50 | 20 | 30 | 70 | 70 | 90 | 100 | 20 | 30 | 80 |
| *Matricaria chamomilla* | 9 | 12 | 21 | 20 | 40 | 70 | 5 | 20 | 50 | 5 | 7 | 10 |

| Active ingredient kg/ha | I + III + IV 1+ 0.5+ 0.5 | I + III + IV 0.5+ 1+ 0.5 | I + III + IV 0.5+ 0.5+ 1 | I + III + V 1+ 0.5+ 0.5 | I + III + V 0.5+ 1+ 0.5 | I + III + V 0.5+ 0.5+ 1 | I + III + VI 1+ 0.5+ 0.5 | I + III + VI 0.5+ 1+ 0.5 | I + III + VI 0.5+ 0.5+ 1 |
|---|---|---|---|---|---|---|---|---|---|
| Crop plants: | | | | | | | | | |
| *Beta vulgaris* | 0 | 0 | 0 | 0 | 0 | 0 | 2.5 | 2.5 | 4 |
| Unwanted plants: | | | | | | | | | |
| *Avena fatua* | 85 | 95 | 100 | 90 | 100 | 100 | 85 | 90 | 95 |
| *Echinochloa crus-galli* | 91 | 100 | 100 | 98 | 100 | 100 | 100 | 100 | 100 |
| *Matricaria chamomilla* | 90 | 97 | 85 | 95 | 95 | 90 | 100 | 100 | 100 |

| Active ingredient | I + III + VIII | | | I + III + IX | | |
|---|---|---|---|---|---|---|
| *Beta vulgaris* | 0 | 0 | 0 | 0 | 0 | 0 |
| *Avena fatua* | 100 | 100 | 100 | 80 | 90 | 85 |
| *Echinochloa crus-galli* | 100 | 100 | 100 | 96 | 100 | 100 |
| *Matricaria chamomilla* | 90 | 90 | 95 | 100 | 97 | 90 |

0 = no damage
100 = complete destruction

EXAMPLE 6

An agricultural plot was sown with various seeds. The soil was then immediately treated with the following amounts of the following individual active ingredients and compositions thereof as dispersions or emulsions:

I: 1-phenyl-4-amino-5-chloropyridazone-(6)
III: O-(methylaminosulfonyl)-glycolic acid-N-isopropylanilide
IV: 2,3-dichloroallyl N,N-diisopropylthiocarbamate
V: 2,3,3-trichloroallyl N,N-diisopropylthiolcarbamate
VI: 2-ethoxy-2,3-dihydro-3,3-dimethyl-5-benzofuranylmethane sulfonate
VIII: 2,3-dihydro-3,3-dimethyl-2-ethoxybenzofuran-5-yldimethylamino sulfonate
IX: ethyl N-ethyl-N-cyclohexylthiolcarbamate,
each at rates of 1, 1.5, 2, 3, 4, 4.5, 5 and 6 kg/ha;
I+III+IV, I+III+V, I+III+VI, I+III+VIII and I+III+IX,
each at rates of 1+1+1, 2+1+1, 1+2+1, 1+1+2, 1.5°1.5°1.5, 3+1+1, 1+3+1, 1+1+3 and 2+2+2 kg/ha;
and for comparison
X: N-(4-chlorophenyl)-N',N'-dimethylurea, 3 and 5 kg/ha;
I+II+X 1+1+3 kg/ha.

After 4 to 5 weeks it was ascertained that the compositions I+III+IV, I+III+V, I+III+VI, I+III+VIII and I+III+IX had better crop tolerance than the composition I+II+X, combined with the same weed control.

The results are given below:

| Active ingredient kg/ha | 1 | 1.5 | 2 | 3 | I<br>4 | 4.5 | 5 | 6 |
|---|---|---|---|---|---|---|---|---|
| Crop plants: | | | | | | | | |
| *Beta vulgaris* | 0 | 0 | 0 | 0 | 10 | 13 | 15 | 20 |
| Unwanted plants: | | | | | | | | |
| *Avena fatua* | 12 | 15 | 20 | 40 | 75 | 85 | 90 | 100 |
| *Echinochloa crus-galli* | 13 | 20 | 32 | 65 | 75 | 80 | 90 | 100 |
| *Matricaria chamomilla* | 40 | 60 | 85 | 100 | 100 | 100 | 100 | 100 |
| Active ingredient | | | | | III | | | |
| *Beta vulgaris* | 0 | 0 | 0 | 0 | 10 | 15 | 20 | 30 |
| *Avena fatua* | 40 | 45 | 54 | 75 | 80 | 65 | 90 | 85 |
| *Echinochloa crus-galli* | 70 | 90 | 100 | 100 | 100 | 100 | 100 | 100 |
| *Matricaria chamomilla* | 35 | 65 | 80 | 90 | 95 | 100 | 100 | 100 |
| Active ingredient kg/ha | 1 | 1.5 | 2 | 3 | IV<br>4 | 4.5 | 5 | 6 |
| *Beta vulgaris* | 0 | 0 | 10 | 15 | 25 | 30 | 35 | 45 |
| *Avena fatua* | 50 | 83 | 95 | 100 | 100 | 100 | 100 | 100 |
| *Echinochloa crus-galli* | 20 | 40 | 50 | 80 | 90 | 100 | 100 | 100 |
| *Matricaria chamomilla* | 10 | 13 | 19 | 30 | 40 | 45 | 55 | 70 |
| Active ingredient | | | | | V | | | |
| Beta vulgaris | 0 | 0 | 7 | 10 | 20 | 28 | 35 | 40 |
| *Avena fatua* | 50 | 90 | 95 | 100 | 100 | 100 | 100 | 100 |
| *Echinochloa crus-galli* | 20 | 50 | 50 | 90 | 96 | 100 | 100 | 100 |
| *Matricaria chamomilla* | 12 | 15 | 21 | 32 | 45 | 50 | 60 | 75 |
| Active ingredient | | | | | VI | | | |
| *Beta vulgaris* | 4 | 5 | 10 | 20 | 25 | 30 | 35 | 40 |
| *Avena fatua* | 40 | 60 | 80 | 100 | 100 | 100 | 100 | 100 |
| *Echinochloa crus-galli* | 30 | 70 | 70 | 100 | 100 | 100 | 100 | 100 |
| *Matricaria chamomilla* | 40 | 50 | 70 | 80 | 95 | 100 | 100 | 100 |
| Active ingredient | | | | | VIII | | | |
| *Beta vulgaris* | 0 | 0 | 0 | 5 | 10 | 12 | 18 | 25 |
| *Avena fatua* | 80 | 100 | 100 | 100 | 100 | 100 | 100 | 100 |
| *Echinochloa crus-galli* | 90 | 100 | 100 | 100 | 100 | 100 | 100 | 100 |
| *Matricaria chamomilla* | 20 | 30 | 50 | 70 | 92 | 100 | 100 | 100 |
| Active ingredient | | | | | IX | | | |
| *Beta vulgaris* | 0 | 0 | 0 | 0 | 10 | 12 | 15 | 20 |
| *Avena fatua* | 30 | 40 | 60 | 95 | 100 | 100 | 100 | 100 |
| *Echinochloa crus-galli* | 30 | 60 | 80 | 95 | 100 | 100 | 100 | 100 |
| *Matricaria chamomilla* | 7 | 9 | 10 | 16 | 48 | 55 | 60 | 75 |

| Active Ingredient | | | | | I + III + IV | | | | |
|---|---|---|---|---|---|---|---|---|---|
| kg/ha | 1+<br>1+<br>1 | 2+<br>1+<br>1 | 1+<br>2+<br>1 | 1+<br>1+<br>2 | 1.5+<br>1.5+<br>1.5 | 3+<br>1+<br>1 | 1+<br>3+<br>1 | 1+<br>1+<br>3 | 2+<br>2+<br>2 |
| *Beta vulgaris* | 0 | 0 | 0 | 10 | 0 | 0 | 0 | 15 | 10 |
| *Avena fatua* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |
| *Matricaria chamomilla* | 100 | 100 | 100 | 100 | 100 | 100 | 100 | 100 | 100 |
| Active ingredient | | | | | I + III + V | | | | |
| *Beta vulgaris* | 0 | 0 | 0 | 7 | 0 | 0 | 0 | 10 | 7 |
| *Avena fatua* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |
| *Matricaria chamomilla* | 100 | 100 | 100 | 100 | 100 | 100 | 100 | 100 | 100 |
| Active ingredient | | | | | I + III + VI | | | | |
| *Beta vulgaris* | 4 | 4 | 4 | 10 | 5 | 4 | 4 | 20 | 10 |
| *Avena fatua* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |
| *Matricaria chamomilla* | 100 | 100 | 100 | 100 | 100 | 100 | 100 | 100 | 100 |
| Active ingredient | | | | | I + III + VIII | | | | |
| *Beta vulgaris* | 0 | 0 | 0 | 0 | 0 | 0 | 0 | 5 | 0 |
| *Avena fatua* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |
| *Matricaria chamomilla* | 100 | 100 | 100 | 100 | 100 | 100 | 100 | 100 | 100 |
| Active ingredient | | | | | I + III + IX | | | | |
| *Beta vulgaris* | 0 | 0 | 0 | 0 | 0 | 0 | 0 | 0 | 0 |
| *Avena fatua* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |
| *Matricaria chamomilla* | 100 | 100 | 100 | 100 | 100 | 100 | 100 | 100 | 100 |

-continued

| Active ingredient kg/ha | X 3 | X 5 | I + II + X 1+1+3 |
|---|---|---|---|
| *Beta vulgaris* | 100 | 100 | 100 |
| *Avena fatua* | 100 | 100 | 100 |
| *Echinochloa crus-galli* | 100 | 100 | 100 |
| *Matricaria chamomilla* | 100 | 100 | 100 |

0 = no damage
100 = complete destruction

EXAMPLE 7

In the greenhouse, various plants were treated at a growth height of from 2 to 16 cm with the following amounts of the following individual active ingredients and compositions thereof as dispersions, emulsions and tankmixes:

I: 1-phenyl-4-amino-5-chloropyridazone-(6)

II: O-(isopropylaminosulfonyl)-glycolic acid-N-butyn-1-yl-3-anilide

III: O-(methylaminosulfonyl)-glycolic acid-N-isopropylanilide,

XII: 3-methoxycarbonylaminophenyl-N-(3′-methylphenyl)-carbamate

XIII: 3-(N-m-trifluoromethylphenylcarbamoyloxy)-(p-methylphenyl)-methylcarbamate XIV: 3-(N-m-methylphenylcarbamoyloxy)-acetoacetic acid anilide XV: 4-chlorobutyn-2-yl-1-N-3-chlorophenylcarbamate XVI: methyl α-chloro-β-(4-chlorophenyl)-propionate XVII: 1,2-dimethyl-3,5-diphenylpyrazolium methyl sulfate each at rates of 0.5, 1, 1.5 and 2 kg/ha;

I+III+XII, I+III+XIII, I+III+XIV, each at rates of 0.5+0.5+0.5, 1+0.5+0.5, 0.5+1+0.5, and 0.5+0.5+1 kg/ha;

II+XII, II+XIII, II+XIV, II+XV, II+XVI, II+XVII, II+XII, III+XIII, III+XIV, III+XV, III+XVI, III+XVII, each at rates of 1+0.5, 0.5+1, 0.5+0.5 and 1+1 kg/ha.

After 2 to 3 weeks it was ascertained that the compositions had a better herbicidal action than their components, combined with the same crop tolerance.

The results are given below:

| Active ingredient kg/ha | I 0.5 | I 1 | I 1.5 | I 2 | II 0.5 | II 1 | II 1.5 | II 2 |
|---|---|---|---|---|---|---|---|---|
| Crop plants: | | | | | | | | |
| *Beta vulgaris* | 0 | 0 | 0 | 0 | 0 | 0 | 0 | 0 |
| Unwanted plants: | | | | | | | | |
| *Avena fatua* | 5 | 13 | 15 | 25 | 30 | 50 | 55 | 60 |
| *Echinochloa crus-galli* | 15 | 25 | 40 | 53 | 45 | 70 | 78 | 85 |
| *Matricaria chamomilla* | 35 | 40 | 50 | 60 | 25 | 45 | 55 | 60 |

| Active ingredient | III | | | |
|---|---|---|---|---|
| *Beta vulgaris* | 0 | 0 | 0 | 0 |
| *Avena fatua* | 25 | 50 | 60 | 65 |
| *Echinochloa crus-galli* | 45 | 70 | 75 | 80 |
| *Matricaria chamomilla* | 20 | 40 | 85 | 95 |

| Active ingredient | XII | | | | XIII | | | |
|---|---|---|---|---|---|---|---|---|
| *Beta vulgaris* | 0 | 0 | 5 | 15 | 0 | 0 | 0 | 0 |
| *Avena fatua* | 3 | 20 | 25 | 30 | 10 | 15 | 30 | 40 |
| *Echinochloa crus-galli* | 10 | 15 | 20 | 30 | 15 | 30 | 65 | 80 |
| *Matricaria chamomilla* | 15 | 30 | 60 | 80 | 15 | 30 | 50 | 70 |

| Active ingredient kg/ha | XIV 0.5 | XIV 1 | XIV 1.5 | XIV 2 | XV 0.5 | XV 1 | XV 1.5 | XV 2 |
|---|---|---|---|---|---|---|---|---|
| *Beta vulgaris* | 0 | 0 | 0 | 0 | 0 | 0 | 0 | 0 |
| *Avena fatua* | 5 | 10 | 15 | 20 | 30 | 60 | 75 | 90 |
| *Echinochloa crus-galli* | 10 | 30 | 50 | 65 | 7 | 12 | 20 | 30 |
| *Matricaria chamomilla* | 10 | 25 | 35 | 50 | 5 | 10 | 20 | 25 |

| Active ingredient | XVI | | | | XVII | | | |
|---|---|---|---|---|---|---|---|---|
| *Beta vulgaris* | 0 | 0 | 0 | 0 | 0 | 0 | 5 | 7 |
| *Avena fatua* | 30 | 45 | 60 | 75 | 32 | 60 | 80 | 90 |
| *Echinochloa crus-galli* | 0 | 2 | 10 | 14 | 0 | 3 | 5 | 10 |
| *Matricaria chamomilla* | 0 | 4 | 10 | 15 | 0 | 9 | 10 | 15 |

| Active ingredient kg/ha | I + III + XII | | | |
|---|---|---|---|---|
| *Beta vulgaris* | 0 | 0 | 0 | 0 |
| *Avena fatua* | 75 | 80 | 98 | 95 |
| *Echinochloa crus-galli* | 100 | 100 | 100 | 100 |
| *Matricaria chamomilla* | 100 | 100 | 100 | 100 |

| Active ingredient | I + III + XIII | | | | I + III + XIV | | | |
|---|---|---|---|---|---|---|---|---|
| *Beta vulgaris* | 0 | 0 | 0 | 0 | 0 | 0 | 0 | 0 |
| *Avena fatua* | 78 | 85 | 100 | 100 | 80 | 85 | 100 | 80 |
| *Echinochloa crus-galli* | 100 | 100 | 100 | 100 | 100 | 100 | 100 | 100 |

-continued

| | | | | | | | | |
|---|---|---|---|---|---|---|---|---|
| *Matricaria chamomilla* | 100 | 100 | 100 | 100 | 100 | 100 | 100 | 100 |

| Active ingredient | II + | XII | | |
|---|---|---|---|---|
| kg/ha | 1 + 0.5 | 0.5 + 1 | 0.5 + 0.5 | 1 + 1 |
| *Beta vulgaris* | 0 | 0 | 0 | 0 |
| *Avena fatua* | 91 | 88 | 71 | 100 |
| *Echinochloa crus-galli* | 100 | 100 | 95 | 100 |
| *Matricaria chamomilla* | 98 | 96 | 80 | 100 |

| Active ingredient | II + | XIII | | | II + | XIV | | |
|---|---|---|---|---|---|---|---|---|
| *Beta vulgaris* | 0 | 0 | 0 | 0 | 0 | 0 | 0 | 0 |
| *Avena fatua* | 100 | 100 | 80 | 100 | 93 | 80 | 73 | 100 |
| *Echinochloa crus-galli* | 100 | 100 | 94 | 100 | 100 | 100 | 92 | 100 |
| *Matricaria chamomilla* | 100 | 96 | 80 | 100 | 95 | 90 | 75 | 100 |

| Active ingredient | II + | XV | | | II + | XVI | | |
|---|---|---|---|---|---|---|---|---|
| *Beta vulgaris* | 0 | 0 | 0 | 0 | 0 | 0 | 0 | 0 |
| *Avena fatua* | 100 | 100 | 100 | 100 | 100 | 100 | 100 | 100 |
| *Echinochloa crus-galli* | 100 | 95 | 90 | 100 | 100 | 87 | 81 | 100 |
| *Matricaria chamomilla* | 90 | 72 | 70 | 95 | 85 | 68 | 63 | 90 |

| Active ingredient | II + | XVII | | |
|---|---|---|---|---|
| kg/ha | 1+ 0.5 | 0.5+ 1 | 0.5+ 0.5 | 1+1 |
| *Beta vulgaris* | 0 | 0 | 0 | 0 |
| *Avena fatua* | 100 | 100 | 100 | 100 |
| *Echinochloa crus-galli* | 100 | 88 | 85 | 100 |
| *Matricaria chamomilla* | 83 | 70 | 63 | 90 |

| Active ingredient | III + | XII | | |
|---|---|---|---|---|
| *Beta vulgaris* | 0 | 0 | 0 | 0 |
| *Avena fatua* | 92 | 85 | 69 | 100 |
| *Echinochloa crus-galli* | 100 | 100 | 95 | 100 |
| *Matricaria chamomilla* | 93 | 90 | 75 | 100 |

| Active ingredient | III + | XIII | | | III + | XIV | | |
|---|---|---|---|---|---|---|---|---|
| *Beta vulgaris* | 0 | 0 | 0 | 0 | 0 | 0 | 0 | 0 |
| *Avena fatua* | 100 | 95 | 72 | 100 | 95 | 75 | 70 | 100 |
| *Echinochloa crus-galli* | 100 | 100 | 90 | 100 | 100 | 100 | 95 | 100 |
| *Matricaria chamomilla* | 94 | 90 | 73 | 100 | 90 | 86 | 70 | 100 |

| Active ingredient | III + | XV | | | III + | XVI | | |
|---|---|---|---|---|---|---|---|---|
| kg/ha | 1 + 0.5 | 0.5 + 1 | 0.5 + 0.5 | 1 + 1 | 1 + 0.5 | 0.5 + 1 | 0.5 + 0.5 | 1 + 1 |
| *Beta vulgaris* | 0 | 0 | 0 | 0 | 0 | 0 | 0 | 0 |
| *Avena fatua* | 100 | 100 | 94 | 100 | 100 | 100 | 95 | 100 |
| *Echinochloa crus-galli* | 100 | 96 | 93 | 100 | 100 | 86 | 85 | 100 |
| *Matricaria chamomilla* | 87 | 80 | 67 | 90 | 85 | 75 | 60 | 92 |

| Active ingredient | III + | XVII | | |
|---|---|---|---|---|
| *Beta vulgaris* | 0 | 0 | 0 | 0 |
| *Avena fatua* | 100 | 100 | 96 | 100 |
| *Echinochloa crus-galli* | 100 | 89 | 80 | 100 |
| *Matricaria chamomilla* | 88 | 80 | 60 | 95 |

0 = no damage
100 = complete destruction

EXAMPLE 8

In the greenhouse, loamy sandy soil was filled into pots and sown with various seeds. The soil prepared in this manner was then treated with the following amounts of the following individual active ingredients and compositions thereof as granules:

II: O-(isopropylaminosulfonyl)-glycolic acid-N-butyn-1-yl-3-anilide

XIX: 1-m-trifluoromethylphenyl-4-methoxy-5-chloropyridazone-(6)

XX: 1-m-trifluoromethylphenyl-4-dimethylamino-5-chloropyradazone-(6)

XXI: 1-m-trifluoromethylphenyl-4-methylamino-5-chloropyridazone-(6)

XXII- O-(ethylaminosulfonyl)-glycolic acid-N-butyn-1-yl-3-anilide

XXIII: O-(methylaminosulfonyl)-glycolic acid-N-butyn-1-yl-3-anilide

XXIV: O-(methylaminosulfonyl)-glycolic acid hexamethylene amide

XXV: O-(ethylaminosulfonyl)-glycolic acid hexamethylene amide

XXVI: O-(n-propylaminosulfonyl)-glycolic acid hexamethylene amide

XXVII: 3-(ethylaminosulfonyloxyacetyl)-3-azabicyclo-[3,2,2]-nonane each at rates of 0.25, 0.75, 0.25 and 1.5 kg/ha, XIX+XXII, XIX+XXIII, XIX+XXIV, XIX+XXV, XIX+XXVI, XIX+XXVII, XIX+II, XX+XXII, XX+XXIII, XX+XXIV, XX+XXV, XX+XXVI, XX+XXVII, XX+II, XXI+XXII, XXI+XXIII, XXI+XXIV, XXI+XXV, XXI+XXVI, XXI+XXVII and XXI+II, each at rates of 1.25+0.25, 0.25+1.25 and 0.75+0.75 kg/ha.

After 4 to 5 weeks it was ascertained that the compositions had a better herbicidal action than their components, combined with the same crop plant compatibility. The results are given below:

| Active ingredient | XIX | | | | XX | | | |
|---|---|---|---|---|---|---|---|---|
| kg/ha | 0.25 | 0.75 | 1.25 | 1.5 | 0.25 | 0.75 | 1.25 | 1.5 |
| Crop plants: | | | | | | | | |
| *Gossypium hirsutum* | 0 | 0 | 0 | 0 | 0 | 0 | 0 | 0 |
| Unwanted plants: | | | | | | | | |
| *Echinochloa crus-galli* | 10 | 20 | 45 | 50 | 5 | 20 | 25 | 37 |
| *Amaranthus retroflexus* | 10 | 30 | 45 | 60 | 5 | 15 | 25 | 33 |

| Active ingredient | XXI | | | | XXII | | | |
|---|---|---|---|---|---|---|---|---|
| *Gossypium hirsutum* | 0 | 0 | 0 | 0 | 0 | 0 | 0 | 0 |
| *Echinochloa crus-galli* | 10 | 30 | 45 | 53 | 30 | 60 | 75 | 90 |
| *Amaranthus retroflexus* | 5 | 20 | 30 | 37 | 20 | 45 | 60 | 65 |

| Active ingredient | XXIII | | | | XXIV | | | |
|---|---|---|---|---|---|---|---|---|
| *Gossypium hirsutum* | 0 | 0 | 0 | 0 | 0 | 0 | 0 | 0 |
| *Echinochloa crus-galli* | 25 | 50 | 70 | 90 | 20 | 45 | 70 | 90 |
| *Amaranthus retroflexus* | 20 | 40 | 70 | 75 | 10 | 25 | 30 | 45 |

| Active ingredient | XXV | | | | XXVI | | | |
|---|---|---|---|---|---|---|---|---|
| kg/ha | 0.25 | 0.75 | 1.25 | 1.5 | 0.25 | 0.75 | 1.25 | 1.5 |
| *Gossypium hirsutum* | 0 | 0 | 0 | 0 | 0 | 0 | 0 | 0 |
| *Echinochloa crus-galli* | 25 | 55 | 75 | 90 | 25 | 50 | 65 | 80 |
| *Amaranthus retroflexus* | 15 | 30 | 45 | 55 | 10 | 20 | 30 | 40 |

| Active ingredient | XXVII | | | | II | | | |
|---|---|---|---|---|---|---|---|---|
| *Gossypium hirsutum* | 0 | 0 | 0 | 0 | 0 | 0 | 0 | 0 |
| *Echinochloa crus-galli* | 35 | 65 | 70 | 90 | 50 | 65 | 75 | 95 |
| *Amaranthus retroflexus* | 20 | 45 | 50 | 60 | 15 | 40 | 55 | 60 |

| Active ingredient | XIX+ XXII | | | XIX+ XXIII | | XIX+ XXIV | | | |
|---|---|---|---|---|---|---|---|---|---|
| kg/ha | 1.25+ 0.25 | 0.25+ 1.25 | 0.75+ 0.75 | 1.25+ 0.25 | 0.25+ 1.25 | 0.75+ 0.75 | 1.25+ 0.25 | 0.25+ 1.25 | 0.75+ 0.75 |
| *Gossypium hirsutum* | 0 | 0 | 0 | 0 | 0 | 0 | 0 | 0 | 0 |
| *Echinochloa crus-galli* | 100 | 100 | 100 | 100 | 100 | 100 | 100 | 100 | 100 |
| *Amaranthus retroflexus* | 100 | 100 | 100 | 100 | 100 | 100 | 84 | 90 | 95 |

| Active ingredient | XIX+ XXV | | | XIX+ XXVI | | XIX+ XXVII | | | |
|---|---|---|---|---|---|---|---|---|---|
| kg/ha | 1.25+ 0.25 | 0.25+ 1.25 | 0.75+ 0.75 | 1.25+ 0.25 | 0.25+ 1.25 | 0.75+ 0.75 | 1.25+ 0.25 | 0.25+ 1.25 | 0.75+ 0.75 |
| *Gossypium hirsutum* | 0 | 0 | 0 | 0 | 0 | 0 | 0 | 0 | |
| *Echinochloa crus-galli* | 100 | 100 | 95 | 100 | 100 | 100 | 100 | 100 | 100 |
| *Amaranthus retroflexus* | 100 | 90 | 100 | 93 | 85 | 90 | 92 | 86 | 90 |

| Active ingredient | XIX+ II | | | XX+ XXII | | XX+ XXIII | | | |
|---|---|---|---|---|---|---|---|---|---|
| *Gossypium hirsutum* | 0 | 0 | 0 | 0 | 0 | 0 | 0 | 0 | 0 |
| *Echinochloa crus-galli* | 100 | 100 | 100 | 92 | 100 | 100 | 94 | 100 | 100 |
| *Amaranthus retroflexus* | 95 | 100 | 100 | 90 | 100 | 100 | 90 | 100 | 100 |

| Active ingredient | XX+ XXIV | | | XX+ XXV | | XX+ XXVI | | | |
|---|---|---|---|---|---|---|---|---|---|
| *Gossypium hirsutum* | 0 | 0 | 0 | 0 | 0 | 0 | 0 | 0 | 0 |
| *Echinochloa crus-galli* | 93 | 100 | 100 | 95 | 100 | 93 | 92 | 100 | 100 |
| *Amaranthus retroflexus* | 80 | 80 | 84 | 90 | 85 | 90 | 80 | 77 | 80 |

| Active ingredient | XX+ XXVII | | | XX+ II | | XXI+ XXII | | | |
|---|---|---|---|---|---|---|---|---|---|
| *Gossypium hirsutum* | 0 | 0 | 0 | 0 | 0 | 0 | 0 | 0 | 0 |
| *Echinochloa crus-galli* | 95 | 100 | 100 | 100 | 100 | 100 | 100 | 100 | 100 |
| *Amaranthus retroflexus* | 90 | 96 | 98 | 80 | 95 | 95 | 95 | 90 | 100 |

| Active ingredient | XXI+ XXIII | | | XXI+ XXIV | | XXI+ XXV | | | |
|---|---|---|---|---|---|---|---|---|---|
| kg/ha | 1.25+ 0.25 | 0.25+ 1.25 | 0.75+ 0.75 | 1.25+ 0.25 | 0.25+ 1.25 | 0.75+ 0.75 | 1.25+ 0.25 | 0.25+ 1.25 | 0.75+ 0.75 |
| *Gossypium hirsutum* | 0 | 0 | 0 | 0 | 0 | 0 | 0 | 0 | 0 |
| *Echinochloa crus-galli* | 100 | 100 | 100 | 100 | 100 | 100 | 100 | 100 | 100 |
| *Amaranthus retroflexus* | 90 | 100 | 100 | 80 | 75 | 90 | 90 | 95 | 96 |

| Active ingredient | XXI+ XXVI | | | XXI+ XXVII | | XXI+ II | | | |
|---|---|---|---|---|---|---|---|---|---|
| *Gossypium hirsutum* | 0 | 0 | 0 | 0 | 0 | 0 | 0 | 0 | 0 |
| *Echinochloa crus-galli* | 100 | 100 | 100 | 100 | 100 | 100 | 100 | 100 | 100 |
| *Amaranthus retroflexus* | 80 | 76 | 85 | 95 | 95 | 100 | 85 | 96 | 98 |

EXAMPLE9

In the greenhouse, loamy sandy soil was filled into pots and sown with various seeds. The soil prepared in this manner was then treated with the following amounts of the following individual ingredients and compositions thereof as dispersions or emulsions:

XXXV: 1-phenyl-4-amino-5-bromopyridazone-(6)

XXXVI: O-(methylaminosulfonyl)-glycolic acid-N-butyn-1-yl-3-anilide

XXXVII: O-(methylaminosulfonyl)-glycolic acid-N butyn-1-yl-3-anilide

XXXVIII: ethyl N,N-diisobutylthiolcarbamate each at rates of 0.5, 1 and 1.5 kg/ha;

XXXV+XXXVI, XXXV+XXXVII, and XXXVIII+XXXVI, each at rates of 0.5+0.5, 1+0.5 and 0.5+1 kg/ha.

After 4 to 5 weeks it was ascertained that the compositions had a better herbicidal action than their components, combined with the same crop plant compatibility.

III: O-(methylaminosulfonyl)-glycolic acid-N-isopropylanilide,

XXXXII: ethyl N,N-di-n-propylthiolcarbamate

XXXXIII: n-propyl N-ethyl-N-n-butylthiolcarbamate each at rates of 0.5, 1, 1.5 and 2 kg/ha;

I+II+XXXXII, I+II+XXXXIII, I+III+XXXXII and I+III+XXXXIII,

| Active ingredient | XXXV | | | XXXVI | | | XXXVII | | | XXVIII | | |
|---|---|---|---|---|---|---|---|---|---|---|---|---|
| kg/ha | 0.5 | 1 | 1.5 | 0.5 | 1 | 1.5 | 0.5 | 1 | 1.5 | 0.5 | 1 | 1.5 |
| Crop plants: | | | | | | | | | | | | |
| *Zea mays* | 0 | 0 | 0 | 0 | 0 | 0 | 0 | 0 | 0 | 0 | 0 | 0 |
| Unwanted plants | | | | | | | | | | | | |
| *Alopecurus myosuroides* | 35 | 55 | 85 | 30 | 50 | 80 | 25 | 40 | 60 | 25 | 50 | 80 |
| *Sinapis arvensis* | 40 | 90 | 100 | 5 | 10 | 20 | 5 | 15 | 20 | 0 | 5 | 10 |
| *Echinochloa crus-galli* | 35 | 40 | 55 | 30 | 55 | 85 | 20 | 50 | 80 | 25 | 38 | 54 |
| | XXXV + XXXVI | | | XXXV+XXXVII | | | XXXVIII+XXXVI | | | | | |
| Active ingredient | 0.5+ | 1+ | 0.5+ | 0.5+ | 1+ | 0.5+ | 0.5+ | 1+ | 0.5+ | | | |
| kg/ha | 0.5 | 0.5 | 1 | 0.5 | 0.5 | 1 | 0.5 | 0.5 | 1 | | | |
| *Zea mays* | 0 | 0 | 0 | 0 | 0 | 0 | 0 | 0 | 0 | | | |
| *Alopecurus myosuroides* | 100 | 100 | 100 | 97 | 100 | 100 | 95 | 100 | 100 | | | |
| *Sinapis arvensis* | 86 | 100 | 90 | 85 | 100 | 97 | 50 | 55 | 50 | | | |
| *Echinochloa crus-galli* | 100 | 100 | 100 | 96 | 100 | 100 | 95 | 100 | 100 | | | |

0 = no damage
100 = complete destruction

EXAMPLE 10

In the greenhouse, loamy sandy soil was filled into pots and sown with various seeds. The soil prepared in this manner was then treated with the following amounts of the following individual active ingredients and compositions thereof as granules:

I: 1-phenyl-4-amino-5-chloropyridazone-(6)

II: O-(isopropylaminosulfonyl)-glycolic acid-N-butyn-1-yl-3-anilide each at rates of 0.5+0.5+0.5, 1+0.5+0.5, 0.5+1+0.5 and 0.5+0.5+1 kg/ha;

II+XXXXII, II+XXXXIII, III+XXXXII and III+XXXXIII, each at rates of 0.5+0.5, 1+0.5, 0.5+1 and 1+1 kg/has.

After 4 to 5 weeks it was ascertained that, at the low application rates, the compositions had a better weed control than their components, combined with the same crop tolerance. At the higher application rates, the crop tolerance was still good.

The results are given below:

| Active ingredient | I | | | | II | | | | III | | | |
|---|---|---|---|---|---|---|---|---|---|---|---|---|
| kg/ha | 0.5 | 1 | 1.5 | 2 | 0.5 | 1 | 1.5 | 2 | 0.5 | 1 | 1.5 | 2 |
| Crop plants: | | | | | | | | | | | | |
| *Beta vulgaris* | 0 | 0 | 0 | 0 | 0 | 0 | 0 | 0 | 0 | 0 | 0 | 0 |
| Unwanted plants: | | | | | | | | | | | | |
| *Avena fatua* | 5 | 12 | 15 | 20 | 40 | 60 | 65 | 75 | 15 | 40 | 45 | 54 |
| *Echinochloa crus-galli* | 6 | 13 | 20 | 32 | 60 | 70 | 95 | 100 | 60 | 70 | 90 | 100 |
| *Matricaria chamomilla* | 20 | 40 | 60 | 85 | 15 | 40 | 60 | 80 | 15 | 35 | 55 | 80 |
| Active ingredient | XXXXII | | | | XXXXIII | | | | | | | |
| *Beta vulgaris* | 0 | 0 | 0 | 0 | 0 | 0 | 0 | 0 | | | | |
| *Avena fatua* | 20 | 27 | 40 | 54 | 20 | 30 | 45 | 59 | | | | |
| *Echinochloa crus-galli* | 28 | 45 | 60 | 80 | 24 | 41 | 55 | 75 | | | | |
| *Matricaria chamomilla* | 10 | 26 | 40 | 50 | 20 | 20 | 25 | 35 | | | | |
| | I + II + XXXXII | | | | I + II + XXXXIII | | | | I + III+ XXXXII | | | |
| Active ingredient | 0.5+ 0.5+ | 1+ 0.5+ | 0.5+ 1+ | 0.5+ 0.5+ | 0.5+ 0.5+ | 1+ 0.5+ | 0.5+ 1+ | 0.5+ 0.5+ | 0.5+ 0.5+ | 1+ 0.5+ | 0.5+ 1+ | 0.5+ 0.5+ |
| kg/ha | 0.5 | 0.5 | 0.5 | 1 | 0.5 | 0.5 | 0.5 | 1 | 0.5 | 0.5 | 0.5 | 1 |
| *Beta vulgaris* | 0 | 0 | 0 | 0 | 0 | 0 | 0 | 0 | 0 | 0 | 0 | 0 |
| *Avena fatua* | 100 | 100 | 100 | 100 | 100 | 100 | 100 | 100 | 80 | 89 | 100 | 87 |
| *Echinochloa crus-galli* | 100 | 100 | 100 | 100 | 100 | 100 | 100 | 100 | 100 | 100 | 100 | 100 |
| *Matricaria chamomilla* | 85 | 100 | 100 | 100 | 95 | 100 | 100 | 100 | 86 | 100 | 100 | 100 |
| Active ingredient | I + III + XXXXIII | | | | | | | | | | | |
| *Beta vulgaris* | 0 | 0 | 0 | 0 | | | | | | | | |
| *Avena fatua* | 80 | 88 | 100 | 92 | | | | | | | | |
| *Echinochloa crus-galli* | 100 | 100 | 100 | 100 | | | | | | | | |
| *Matricaria chamomilla* | 95 | 100 | 100 | 95 | | | | | | | | |
| | II + XXXXII | | | | II + XXXXIII | | | | | | | |
| Active ingredient | 0.5+ | 1+ | 0.5+ | 1+1 | 0.5+ | 1+ | 0.5+ | 1+1 | | | | |
| kg/ha | 0.5 | 0.5 | 1 | | 0.5 | 0.5 | 1 | | | | | |
| *Beta vulgaris* | 0 | 0 | 0 | 0 | 0 | 0 | 0 | 0 | | | | |
| *Avena fatua* | 97 | 100 | 100 | 100 | 98 | 100 | 100 | 100 | | | | |
| *Echinochloa crus-galli* | 100 | 100 | 100 | 100 | 100 | 100 | 100 | 100 | | | | |
| *Matricaria chamomilla* | 65 | 90 | 82 | 100 | 75 | 100 | 76 | 100 | | | | |
| Active ingredient | III + XXXXII | | | | III + XXXXIII | | | | | | | |
| *Beta vulgaris* | 0 | 0 | 0 | 0 | 0 | 0 | 0 | 0 | | | | |
| *Avena fatua* | 75 | 100 | 85 | 100 | 76 | 97 | 85 | 100 | | | | |
| *Echinochloa crus-galli* | 100 | 100 | 100 | 100 | 100 | 100 | 100 | 100 | | | | |

-continued

| | | | | | | | | |
|---|---|---|---|---|---|---|---|---|
| *Matricaria chamomilla* | 67 | 85 | 82 | 100 | 75 | 95 | 75 | 97 |

0 = no damage
100 = complete destruction

EXAMPLE 11

In the greenhouse, loamy sandy soil was filled into pots and sown with various seeds. The soil prepared in this manner was then treated with the following amounts of the following individual active ingredients and compositions thereof as emulsions or dispersions:

II: O-(isopropylaminosulfonyl)-glycolic acid-N-butyn-1-yl-3-anilide

III: O-(methylaminosulfonyl)-glycolic acid-N-isopropylanilide

IV: 2,3-dichloroallyl N,N-diisopropylthiolcarbamate

V: 2,3,3-trichloroallyl N,N-diisopropylthiolcarbamate

VI: 2-ethoxy-2,3-dihydro-3,3-dimethyl-5-benzofuranylmethane sulfonate

VII: 2,3-dihydro-3,3-dimethyl-2-ethoxybenzofuran-5-ylmethylamino sulfonate

VIII: 2,3-dihydro-3,3-dimethyl-2-ethoxybenzofuran-5-yldimethylamino sulfonate

IX: ethyl N-ethyl-N-cyclohexylthiolcarbamate

XXXXVII: α,α-dichloropropionic acid, sodium salt

XXXXVIII: trichloroacetic acid, sodium salt, each at rates of 0.5, 1, 1.5 and 2 kg/ha;

II+IV, II+V, II+VI, II+VII, II+VIII, II+IX, III+IV, III+V, III+VI, III+VII, III+VIII, III+IX, II+XXXXVII, II+XXXXVIII, III+XXXXVII, and III+XXXXVIII, each at rates of 0.5+1, 1+0.5 and 0.5+0.5 kg/ha.

After 2 to 3 weeks it was ascertained that, at the lower application rates, the compositions had a better herbicidal action than their components, combined with the same crop plant compatibility. At higher application rates the compatibility was still good.

The results are given below:

| Active ingredient | II | | | | III | | | | IV | | | |
|---|---|---|---|---|---|---|---|---|---|---|---|---|
| kg/ha | 0,5 | 1 | 1,5 | 2 | 0,5 | 1 | 1,5 | 2 | 0,5 | 1 | 1,5 | 2 |
| Crop plants: | | | | | | | | | | | | |
| *Beta vulgaris* | 0 | 0 | 0 | 0 | 0 | 0 | 0 | 0 | 0 | 0 | 0 | 10 |
| Unwanted plants: | | | | | | | | | | | | |
| *Avena fatua* | 40 | 60 | 65 | 75 | 15 | 40 | 45 | 54 | 20 | 50 | 83 | 95 |
| *Echinochloa crus-galli* | 60 | 70 | 95 | 100 | 25 | 70 | 90 | 100 | 10 | 20 | 40 | 50 |
| *Matricaria chamomilla* | 15 | 40 | 60 | 80 | 15 | 35 | 55 | 80 | 5 | 10 | 13 | 19 |

| Active ingredient | V | | | | VI | | | |
|---|---|---|---|---|---|---|---|---|
| *Beta vulgaris* | 0 | 0 | 0 | 0 | 2,5 | 4 | 5 | 10 |
| *Avena fatua* | 25 | 50 | 90 | 95 | 16 | 40 | 60 | 80 |
| *Echinochloa crus-galli* | 10 | 20 | 50 | 50 | 20 | 30 | 70 | 70 |
| *Matricaria chamomilla* | 9 | 12 | 15 | 21 | 20 | 40 | 50 | 70 |

| Active ingredient | VII | | | | VIII | | | | |
|---|---|---|---|---|---|---|---|---|---|
| *Beta vulgaris* | 0 | 0 | | 0 | 0 | 0 | 0 | 0 | |
| *Avena fatua* | 20 | 40 | | 60 | 90 | 45 | 80 | 100 | 100 |
| *Echinochloa crus-galli* | 10 | 30 | | 37 | 58 | 70 | 90 | 100 | 100 |
| *Matricaria chamomilla* | 7 | 30 | | 35 | 40 | 5 | 20 | 30 | 50 |

| Active ingredient | XXXXVII | | | | XXXXVIII | | | |
|---|---|---|---|---|---|---|---|---|
| kg/ha | 0.5 | 1 | 1.5 | 2 | 0.5 | 1 | 1.5 | 2 |
| *Beta vulgaris* | 0 | 0 | 0 | 0 | 0 | 0 | 0 | 0 |
| *Avena fatua* | 7 | 27 | 60 | 76 | 5 | 24 | 45 | 56 |
| *Echinochloa crus-galli* | 3 | 23 | 35 | 44 | 3 | 17 | 30 | 40 |
| *Matricaria chamomilla* | 0 | 0 | 3 | 5 | 3 | 0 | 2 | 7 |

| Active ingredient | IX | | | |
|---|---|---|---|---|
| *Beta vulgaris* | 0 | 0 | 0 | 0 |
| *Avena fatua* | 10 | 30 | 40 | 60 |
| *Echinochloa crus-galli* | 20 | 30 | 60 | 80 |
| *Matricaria chamomilla* | 5 | 7 | 9 | 10 |

| Active ingredient | II + IV | | | II + V | | | II + VI | | |
|---|---|---|---|---|---|---|---|---|---|
| kg/ha | 0.5+ 1 | 1+ 0.5 | 0.5+ 0.5 | 0.5+ 1 | 1+ 0.5 | 0.5+ 0.5 | 0.5+ 1 | 1+ 0.5 | 0.5+ 0.5 |
| *Beta vulgaris* | 0 | 0 | 0 | 0 | 0 | 0 | 4 | 2,5 | 2,5 |
| *Avena fatua* | 100 | 100 | 95 | 100 | 100 | 100 | 100 | 100 | 98 |
| *Echinochloa crus-galli* | 100 | 100 | 100 | 100 | 100 | 100 | 100 | 100 | 100 |
| *Matricaria chamomilla* | 70 | 90 | 67 | 74 | 94 | 70 | 100 | 98 | 80 |

| Active ingredient | II + VII | | | II + VIII | | | II + IX | | |
|---|---|---|---|---|---|---|---|---|---|
| *Beta vulgaris* | 0 | 0 | 0 | 0 | 0 | 0 | 0 | 0 | 0 |
| *Avena fatua* | 100 | 100 | 96 | 100 | 100 | 100 | 100 | 100 | 93 |
| *Echinochloa crus-galli* | 100 | 100 | 100 | 100 | 100 | 100 | 100 | 100 | 100 |
| *Matricaria chamomilla* | 90 | 90 | 67 | 80 | 90 | 70 | 70 | 90 | 65 |

| Active ingredient | III + IV | | | XXX + V | | | III + VI | | |
|---|---|---|---|---|---|---|---|---|---|
| *Beta vulgaris* | 0 | 0 | 0 | 0 | 0 | 0 | 4 | 2,5 | 2,5 |
| *Avena fatua* | 100 | 98 | 80 | 100 | 100 | 76 | 98 | 87 | 62 |
| *Echinochloa crus-galli* | 94 | 100 | 86 | 90 | 100 | 80 | 96 | 100 | 80 |
| *Matricaria chamomilla* | 70 | 80 | 68 | 70 | 90 | 68 | 100 | 98 | 80 |

| Active ingredient | III + VII | | | III + VIII | | | III + IX | | |
|---|---|---|---|---|---|---|---|---|---|
| kg/ha | 0,5+ 1 | 1+ 0,5 | 0,5+ 0,5 | 0,5 1 | 1+ 0,5 | 0,5+ 0,5 | 0,5+ 1 | 1+ 0,5 | 0,5+ 0,5 |
| *Beta vulgaris* | 0 | 0 | 0 | 0 | 0 | 0 | 0 | 0 | 0 |
| *Avena fatua* | 92 | 97 | 78 | 100 | 100 | 100 | 87 | 85 | 65 |

-continued

| | | | | | | | | | |
|---|---|---|---|---|---|---|---|---|---|
| *Echinochloa crus-galli* | 98 | 100 | 80 | 100 | 100 | 100 | 96 | 100 | 80 |
| *Matricaria chamomilla* | 90 | 80 | 67 | 70 | 78 | 80 | 64 | 75 | 60 |
| Active ingredient | II + XXXXVII | | | II + XXXXVIII | | | III + XXXXVII | | |
| *Beta vulgaris* | 0 | 0 | 0 | 0 | 0 | 0 | 0 | 0 | 0 |
| *Avena fatua* | 100 | 100 | 90 | 100 | 100 | 80 | 85 | 86 | 65 |
| *Echinochloa crus-galli* | 100 | 100 | 98 | 100 | 100 | 95 | 90 | 100 | 90 |
| *Matricaria chamomilla* | 60 | 80 | 52 | 60 | 78 | 60 | 57 | 75 | 58 |
| Active ingredient | III + XXXVIII | | | | | | | | |
| *Beta vulgaris* | 0 | 0 | 0 | | | | | | |
| *Avena fatua* | 85 | 80 | 65 | | | | | | |
| *Echinochloa crus-galli* | 90 | 100 | 87 | | | | | | |
| *Matricaria chamomilla* | 57 | 70 | 55 | | | | | | |

0 = no damage
100 = complete destruction

EXAMPLE 12

In the greenhouse, loamy sandy soil was filled into pots and sown with various seeds. The soil prepared in this manner was then treated with the following amounts of the following individual active ingredients and compositions thereof as emulsions or dispersions:

II: O-(isopropylaminosulfonyl)-glycolic acid-N-butyn-1-yl-3-anilide

XXII: O-(ethylaminosulfonyl)-glycolic acid-N-butyn-1-yl-3-anilide

XXIII: O-(methylaminosulfinyl)-glycolic acid-N-butyn-1-yl-3-anilide

XXXXIV: ethyl β-(N-phenyl-N-methyl)-amino-α-cyanoacrylate each at rates of 0.25, 0.5, 0.75, 1, 1.5, 2, 2.5, 3 and 4 kg/ha;

XXXXIV+II, XXXXIV+XXII, XXXXIV+XXIII, each at rates of 0.25+0.75, 0.75+0.25, 0.5+0.5, 0.5+1, 1+0.5, 0.75+0.75, 0.5+1.5, 1.5+0.5, 1+1, 0.5+2.5, 2.5+0.5, 1.5+1.5, 1+2, 2+1 and 2+2 kg/ha.

After 4 to 5 weeks it was ascertained that, at the low application rates, the compositions had a better herbicidal action than their components, combined with the same crop plant compatibility. The crop tolerance was still good at the higher application rates.

The results are given below:

| Active ingredient kg/ha | 0.25 | 0,5 | 0.75 | 1 | 1.5 | 2 | 2.5 | 3 | 4 |
|---|---|---|---|---|---|---|---|---|---|
| Crop plants: | | | | | | | | | |
| *Gossypium hirsutum* | 0 | 0 | 0 | 0 | 0 | 0 | 0 | 10 | 15 |
| Unwanted plants: | | | | | | | | | |
| *Digitaria sanguinalis* | 20 | 50 | 70 | 80 | 95 | 100 | 100 | 100 | 100 |
| *Amaranthus retroflexus* | 10 | 15 | 40 | 50 | 60 | 100 | 100 | 100 | 100 |
| Active ingredients | | | | | XXIII | | | | |
| *Gossypium hirsutum* | 0 | 0 | 0 | 0 | 0 | 0 | 5 | 10 | 20 |
| *Digitaria sanguinalis* | 30 | 60 | 80 | 90 | 100 | 100 | 100 | 100 | 100 |
| *Amaranthus retroflexus* | 20 | 30 | 40 | 60 | 75 | 100 | 100 | 100 | 100 |
| Active ingredients | | | | | XXII | | | | |
| *Gossypium hirsutum* | 0 | 0 | 0 | 0 | 0 | 0 | 5 | 10 | 20 |
| *Digitaria sanguinalis* | 25 | 54 | 75 | 86 | 98 | 100 | 100 | 100 | 100 |
| *Amaranthus retroflexus* | 20 | 30 | 45 | 50 | 65 | 100 | 100 | 100 | 100 |
| Active ingredients | | | | | XXXXIV | | | | |
| *Gossypium hirsutum* | 0 | 0 | 0 | 0 | 0 | 0 | 0 | 0 | 10 |
| *Digitaria sanguinalis* | 10 | 30 | 60 | 80 | 95 | 100 | 100 | 100 | 100 |
| *Amaranthus retroflexus* | 20 | 30 | 40 | 50 | 80 | 95 | 100 | 100 | 100 |

| Active ingredient kg/ha | 0.25+ 0.75 | 0.75+ 0.25 | | 0.5+ 0.5 | 1+ 1 | 0.75+ 0.5 | 0.5+ 0.75 | 1.5+ 1.5 | 1+1 0.5 | 0.5+ | 2,5 |
|---|---|---|---|---|---|---|---|---|---|---|---|
| | | | | | XXXXIV + XXIII | | | | | | |
| *Gossypium hirsutum* | 0 | 0 | | 0 | 0 | 0 | 0 | 0 | 0 | 0 | 0 |
| *Digitaria sanguinalis* | 100 | 100 | | 100 | 100 | 100 | 100 | 100 | 100 | 100 | 100 |
| *Amaranthus retroflexus* | 100 | 98 | | 95 | 100 | 100 | 100 | 100 | 100 | 100 | 100 |
| Active ingredient | | | | | XXXXIV + II | | | | | | |
| *Gossypium hirsutum* | 0 | 0 | 0 | 0 | 0 | 0 | 0 | 0 | 0 | 0 | |
| *Digitaria sanguinalis* | 100 | 100 | 100 | 100 | 100 | 100 | 100 | 100 | 100 | 100 | |
| *Amaranthus retroflexus* | 98 | 85 | 80 | 100 | 100 | 100 | 100 | 100 | 100 | 100 | |
| Active ingredient | | | | | XXXXIV + XXII | | | | | | |
| *Gossypium hirsutum* | 0 | 0 | 0 | 0 | 0 | 0 | | 0 | 0 | 0 | |
| *Digitaria sanguinalis* | 100 | 100 | 100 | 100 | 100 | 100 | | 100 | 100 | 100 | 100 |
| *Amaranthus retroflexus* | 100 | 100 | 100 | 100 | 100 | 100 | | 100 | 100 | 100 | 100 |

| Active ingredient kg/ha | 2.5+ 0.5 | 1.5+ 1.5 | 1+2 | 2+1 | 2+2 |
|---|---|---|---|---|---|
| | | XXXXIV + XXIII | | | |
| *Gossypium hirsutum* | 0 | 0 | 0 | 0 | 0 |
| *Digitaria sanguinalis* | 100 | 100 | 100 | 100 | 100 |
| *Amaranthus retroflexus* | 100 | 100 | 100 | 100 | 100 |
| Active ingredient | | XXXXIV + II | | | |
| *Gossypium hirsutum* | 0 | 0 | 0 | 0 | 0 |
| *Digitaria sanguinalis* | 100 | 100 | 100 | 100 | 100 |
| *Amaranthus retroflexus* | 100 | 100 | 100 | 100 | 100 |
| Active ingredient | | XXXXIV + XXII | | | |
| *Gossypium hirsutum* | 0 | 0 | 0 | 0 | 0 |
| *Digitaria sanguinalis* | 100 | 100 | 100 | 100 | 100 |

-continued

| | | | | | |
|---|---|---|---|---|---|
| *Amaranthus retroflexus* | 100 | 100 | 100 | 100 | 100 |

0 = no damage
= complete destruction

EXAMPLE 13

In the greenhouse, loamy sandy soil was fitted into pots and sown with various seeds. The soil prepared in this manner was then treated with the following amounts of the following individual active ingredients and compositions thereof as emulsions or dispersions:

I: 1-phenyl-4-amino-5-chloropyridazone-(6)
II: O-(isopropylaminosulfonyl)-glycolic acid-N-butyn-1-yl-3-anilide
III: O-(methylaminosulfonyl)-glycolic acid-N-isopropylanilide
VI: 2-ethoxy-2,3-dihydro-3,3-dimethyl-5-benzofuranylmethane sulfonate
VII: 2,3-dihydro-3,3-dimethyl-2-ethoxybenzofuran-5-ylmethylamino sulfonate
VIII: 2,3-dihydro-3,3-dimethyl-2-ethoxybenzofuran-5-yldimethylamino sulfonate
XXXIII: 2,3-dihydro-3,3-dimethyl-2-methoxybenzofuran-5-yldimethylamino sulfonate
XXXIX: O-(methylsulfonyl)-glycolic acid-N-ethoxymethyl-2-methyl-6-ethylanilide
XXXX: S-(p-chlorobenzyl)-(2,2,4-trimethylazetidine)-1-carbothiolate
XXXXI: S-(2,3,3-trichloroallyl)-(2,2,4-trimethylazetidine)-1-carbothiolate
XXXXV: 2,3-dihydro-3,3-dimethyl-2-ethoxybenzofuran-5-yl-(N-methyl-N-chloroacetyl)-amionsulfonate
XXXXVI: 2,3-dihydro-3,3-dimethyl-2-ethozybenzofuran-5-yl-N-methyl-N-acetylamino sulfonate
XXXXIX: O-(methylsulfonyl)-glycolic acid-N-ethoxymethyl-2,6-dimethylanilide
L isopropyl N-[1-phenyl-5-bromopyridazon-6-yl-(4)]-oxamate
LI tert-butyl N-[1-phenyl-5-bromopyridazon-6-yl-(4)]-oxamate
LII: 1-phenyl-4-bromacetylamino-5-bromopyridazone-(6)
LIII: 1-phenyl-4-dichloroacetylamino-5-bromopyridazone-(6)

each at rates of 0.25, 0.5, 0.75, 1, 1.5, 2, 3 and 4 kg/ha
I+XXXIX, I+XXXXIX, II+VI, II+VII, II+VIII, I+XXXIII, II+XXXIX, II+XXXX, II+XXXXI, II+XXXXV, II+XXXXVI, II+XXXXIX, II+L, II+LI, II+LII, II+LIII, III+VI, III+VII, III+λ VIII, III+XXXIII, III+XXXIX, III+XXXX, III+XXXXI, III+XXXXV, III+XXXXVI, III+XXXXIX, III+L, III+LI, III+LII, and III+λ LIII,
each at rates of 0.25+0.75, 0.75+0.25, 2+1, 1+2, 1.5+1.5, and 2+2 kg/ha;
I+III+XXXXVI,
at rates of 0.25+0.25+0.5, 0.25+0.5+0.25, 0.5+0.25+0.25, 0.25+0.25+1.5, 0.25+1.5+0.25, and 1.5+0.25+0.25 kg/ha.

During the experiment the soil and plants were kept fairly dry.

After 2 to 3 weeks it was ascertained that, at the lower application rates, the compositions had a better herbicidal action than their components, combined with the same crop plant compatibility. The crop tolerance at the higher application rates was still good.

The results are given below:

| Active ingredient kg/ha | 0,25 | 0,5 | 0,75 | I 1 | 1,5 | 2 | 3 | 4 |
|---|---|---|---|---|---|---|---|---|
| Crop plants: | | | | | | | | |
| *Beta vulgaris* | 0 | 0 | 0 | 0 | 0 | 0 | 0 | 10 |
| Unwanted plants: | | | | | | | | |
| *Avena fatua* | 0 | 5 | 8 | 12 | 15 | 20 | 40 | 75 |
| *Echinochloa crus-galli* | 5 | 6 | 10 | 13 | 20 | 32 | 65 | 75 |
| *Matricaria chamomilla* | 15 | 20 | 30 | 40 | 60 | 85 | 100 | 100 |
| Active ingredient | | | | II | | | | |
| *Beta vulgaris* | 0 | 0 | 0 | 0 | 0 | 0 | 5 | 10 |
| *Avena fatua* | 30 | 40 | 55 | 60 | 65 | 75 | 85 | 90 |
| *Echinochloa crus-galli* | 50 | 60 | 65 | 70 | 95 | 100 | 100 | 100 |
| *Matricaria chamomilla* | 5 | 15 | 30 | 40 | 60 | 80 | 90 | 95 |
| Active ingredient | | | | III | | | | |
| *Beta vulgaris* | 0 | 0 | 0 | 0 | 0 | 0 | 0 | 10 |
| *Avena fatua* | 10 | 15 | 30 | 40 | 45 | 54 | 78 | 80 |
| *Echinochloa crus-galli* | 20 | 25 | 45 | 70 | 90 | 100 | 100 | 100 |
| *Matricaria chamomilla* | 5 | 15 | 25 | 35 | 55 | 80 | 90 | 95 |
| Active ingredient kg/ha | 0,25 | 0,5 | 0,75 | VI 1 | 1,5 | 2 | 3 | 4 |
| *Beta vulgaris* | 0 | 2,5 | 3 | 4 | 5 | 10 | 20 | 25 |
| *Avena fatua* | 10 | 16 | 30 | 40 | 60 | 80 | 100 | 100 |
| *Echinochloa crus-galli* | 20 | 25 | 45 | 70 | 90 | 100 | 100 | 100 |
| *Matricaria chamomilla* | 5 | 15 | 25 | 35 | 55 | 80 | 90 | 95 |
| Active ingredient | | | | VII | | | | |
| *Beta vulgaris* | 0 | 0 | 0 | 0 | 0 | 0 | 0 | 7 |
| *Avena fatua* | 10 | 20 | 30 | 40 | 60 | 90 | 100 | 100 |
| *Echinochloa crus-galli* | 5 | 10 | 20 | 30 | 37 | 58 | 70 | 80 |
| *Matricaria chamomilla* | 5 | 7 | 15 | 30 | 35 | 40 | 60 | 80 |
| Active ingredient | | | | VIII | | | | |
| *Beta vulgaris* | 0 | 0 | 0 | 0 | 0 | 0 | 5 | 10 |
| *Avena fatua* | 30 | 45 | 65 | 80 | 100 | 100 | 100 | 100 |
| *Echinochloa crus-galli* | 50 | 70 | 80 | 90 | 100 | 100 | 100 | 100 |

-continued

| | | | | | | | | |
|---|---|---|---|---|---|---|---|---|
| *Matricaria chamomilla* | 3 | 5 | 15 | 20 | 30 | 50 | 70 | 92 |

| Active ingredient | | | | XXXIII | | | | |
|---|---|---|---|---|---|---|---|---|
| kg/ha | 0,25 | 0,5 | 0,75 | 1 | 1,5 | 2 | 3 | 4 |
| *Beta vulgaris* | 0 | 0 | 0 | 0 | 0 | 0 | 4 | 10 |
| *Avena fatua* | 35 | 60 | 70 | 80 | 95 | 100 | 100 | 100 |
| *Echinochloa crus-galli* | 30 | 45 | 50 | 60 | 78 | 80 | 100 | 100 |
| *Matricaria chamomilla 0* | 5 | 10 | 20 | 28 | 45 | 65 | 85 | |

| Active ingredient | | | | XXXIX | | | | |
|---|---|---|---|---|---|---|---|---|
| *Beta vulgaris* | 0 | 0 | 0 | 0 | 0 | 0 | 10 | 15 |
| *Avena fatua* | 15 | 20 | 30 | 40 | 65 | 80 | 90 | 100 |
| *Echinochloa crus-galli* | 20 | 30 | 40 | 50 | 85 | 100 | 100 | 100 |
| *Matricaria chamomilla* | 20 | 30 | 40 | 60 | 75 | 95 | 100 | 100 |

| Active ingredient | | | | XXXX | | | | |
|---|---|---|---|---|---|---|---|---|
| *Beta vulgaris* | 0 | 0 | 0 | 0 | 0 | 0 | 5 | 20 |
| *Avena fatua* | 20 | 35 | 45 | 50 | 70 | 90 | 95 | 100 |
| *Echinochloa crus-galli* | 35 | 50 | 60 | 70 | 85 | 100 | 100 | 100 |
| *Matricaria chamomilla* | 5 | 10 | 20 | 30 | 60 | 80 | 95 | 100 |

| Active ingredient | | | | XXXXI | | | | |
|---|---|---|---|---|---|---|---|---|
| kg/ha | 0,25 | 0,5 | 0,75 | 1 | 1,5 | 2 | 3 | 4 |
| *Beta vulgaris* | 0 | 0 | 0 | 0 | 0 | 0 | 0 | 15 |
| *Avena fatua* | 20 | 30 | 50 | 60 | 70 | 90 | 100 | 100 |
| *Echinochloa crus-galli* | 3 | 5 | 10 | 15 | 20 | 30 | 45 | 50 |
| *Matricaria chamomilla* | 0 | 0 | 0 | 5 | 10 | 20 | 30 | 40 |

| Active ingredient | | | | XXXXV | | | | |
|---|---|---|---|---|---|---|---|---|
| *Beta vulgaris* | 0 | 0 | 0 | 0 | 0 | 0 | 0 | 10 |
| *Avena fatua* | 15 | 25 | 40 | 50 | 70 | 90 | 100 | 100 |
| *Echinochloa crus-galli* | 15 | 30 | 35 | 40 | 50 | 70 | 95 | 100 |
| *Matricaria chamomilla* | 0 | 0 | 10 | 15 | 25 | 35 | 45 | 60 |

| Active ingredient | | | | XXXXVI | | | | |
|---|---|---|---|---|---|---|---|---|
| *Beta vulgaris* | 0 | 0 | 0 | 0 | 0 | 0 | 10 | 20 |
| *Avena fatua* | 20 | 30 | 45 | 60 | 80 | 100 | 100 | 100 |
| *Echinochloa crus-galli* | 20 | 40 | 60 | 70 | 90 | 100 | 100 | 100 |
| *Matricaria chamomilla* | 0 | 5 | 10 | 20 | 30 | 40 | 50 | 70 |

| Active ingredient | | | | XXXXIX | | | | |
|---|---|---|---|---|---|---|---|---|
| kg/ha | 0.25 | 0.5 | 0.75 | 1 | 1.5 | 2 | 3 | 4 |
| *Beta vulgaris* | 0 | 0 | 0 | 0 | 0 | 0 | 5 | 25 |
| *Avena fatua* | 10 | 20 | 30 | 45 | 60 | 85 | 100 | 100 |
| *Echinochloa crus-galli* | 15 | 25 | 35 | 50 | 80 | 100 | 100 | 100 |
| *Matricaria chamomilla* | 0 | 0 | 10 | 20 | 35 | 40 | 50 | 70 |

| Active ingredient | | | | L | | | | |
|---|---|---|---|---|---|---|---|---|
| *Beta vulgaris* | 0 | 0 | 0 | 0 | 0 | 0 | 0 | 5 |
| *Avena fatua* | 0 | 3 | 10 | 12 | 15 | 20 | 35 | 60 |
| *Echinochloa crus-galli* | 0 | 5 | 10 | 15 | 20 | 30 | 60 | 70 |
| *Matricaria chamomilla* | 10 | 15 | 25 | 40 | 60 | 80 | 95 | 100 |

| Active ingredient | | | | | | | LI | |
|---|---|---|---|---|---|---|---|---|
| *Beta vulgaris* | 0 | 0 | 0 | 0 | 0 | 0 | 10 | 20 |
| *Avena fatua* | 0 | 5 | 10 | 15 | 18 | 23 | 40 | 70 |
| *Echinochloa crus-galli* | 5 | 8 | 12 | 15 | 23 | 30 | 60 | 65 |
| *Matricaria chamomilla* | 10 | 20 | 25 | 35 | 55 | 70 | 90 | 100 |

| Active ingredient | | | | LII | | | | |
|---|---|---|---|---|---|---|---|---|
| kg/ha | 0.25 | 0.5 | 0.75 | 1 | 1.5 | 2 | 3 | 4 |
| *Beta vulgaris* | 0 | 0 | 0 | 0 | 0 | 0 | 0 | 10 |
| *Avena fatua* | 3 | 5 | 7 | 10 | 15 | 20 | 40 | 60 |
| *Echinochloa crus-galli* | 5 | 7 | 10 | 15 | 20 | 30 | 45 | 65 |
| *Matricaria chamomilla* | 5 | 13 | 20 | 30 | 50 | 70 | 90 | 95 |

| Active ingredient | | | | LIII | | | | |
|---|---|---|---|---|---|---|---|---|
| *Beta vulgaris* | 0 | 0 | 0 | 0 | 0 | 0 | 0 | 10 |
| *Avena fatua* | 0 | 7 | 10 | 13 | 17 | 21 | 35 | 60 |
| *Echinochloa crus-galli* | 5 | 10 | 13 | 15 | 20 | 30 | 50 | 70 |
| *Matricaria chamomilla* | 15 | 20 | 30 | 45 | 60 | 80 | 95 | 100 |

| | I + XXXIX | | | | | | I + XXXXIX | | | | | |
|---|---|---|---|---|---|---|---|---|---|---|---|---|
| Active ingredient | 0.25+ | 0.75+ | 2+1 | 1+2 | 1.5+ | 2+2 | 0.25+ | 0.75+ | 2+1 | 1+2 | 1.5+ | 2+2 |
| kg/ha | 0.75 | 0.25 | | | 1.5 | | 0.75 | 0.25 | | | 1.5 | |
| *Beta vulgaris* | 0 | 0 | 0 | 0 | 0 | 0 | 0 | 0 | 0 | 0 | 0 | 0 |
| *Avena fatua* | 72 | 55 | 100 | 100 | 100 | 100 | 70 | 60 | 100 | 100 | 100 | 100 |
| *Echinochloa crus-galli* | 85 | 70 | 100 | 100 | 100 | 100 | 80 | 65 | 100 | 100 | 100 | 100 |
| *Matricaria chamomilla* | 95 | 90 | 100 | 100 | 100 | 100 | 65 | 68 | 100 | 100 | 100 | 100 |

| Active ingredient | II + VI | | | | | | II + VII | | | | | |
|---|---|---|---|---|---|---|---|---|---|---|---|---|
| *Beta vulgaris* | 3 | 0 | 4 | 10 | 5 | 10 | 0 | 0 | 0 | 0 | 0 | 0 |
| *Avena fatua* | 98 | 100 | 100 | 100 | 100 | 100 | 97 | 100 | 100 | 100 | 100 | 100 |
| *Echinochloa crus-galli* | 100 | 100 | 100 | 100 | 100 | 100 | 100 | 100 | 100 | 100 | 100 | 100 |
| *Matricaria chamomilla* | 75 | 80 | 100 | 100 | 100 | 100 | 60 | 75 | 100 | 100 | 100 | 100 |

| Active ingredient | II + VIII | | | | | | II + XXXIII | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 100 | 100 | 100 | 100 | 100 | 100 | 100 | 100 | 100 | 100 | 100 | 100 |

-continued

| | | | | | | | | | | | | |
|---|---|---|---|---|---|---|---|---|---|---|---|---|
| *Echinochloa crus-galli* | 100 | 100 | 100 | 100 | 100 | 100 | 100 | 100 | 100 | 100 | 100 | 100 |
| *Matricaria chamomilla* | 58 | 70 | 100 | 100 | 100 | 100 | 58 | 70 | 100 | 100 | 100 | 100 |

| | II + XXXIX | | | | | | II + XXXX | | | | | |
|---|---|---|---|---|---|---|---|---|---|---|---|---|
| Active ingredient kg/ha | 0.25+ 0.75 | 0.75+ 0.25 | 2+1 | 1+2 | 1.5+ 1.5 | 2+2 | 0.25+ 0.75 | 0.75+ 0.25 | 2+1 | 1+2 | 1.5+ 1.5 | 2+2 |
| *Beta vulgaris* | 0 | 0 | 0 | 0 | 0 | 0 | 0 | 0 | 0 | 0 | 0 | 0 |
| *Avena fatua* | 98 | 100 | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 | 100 |
| *Matricaria chamomilla* | 85 | 90 | 100 | 100 | 100 | 100 | 68 | 70 | 100 | 100 | 100 | 100 |

| Active ingredient | II + XXXXI | | | | | | II + XXXXV | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 100 | 100 | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 | 100 |
| *Matricaria chamomilla* | 50 | 70 | 100 | 100 | 100 | 100 | 62 | 75 | 100 | 100 | 100 | 100 |

| Active ingredient | II + XXXXVI | | | | | | II + XXXXIX | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 100 | 100 | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 | 100 |
| *Matricaria chamomilla* | 57 | 70 | 100 | 100 | 100 | 100 | 60 | 71 | 100 | 100 | 100 | 100 |

| | II + L | | | | | | III + VI | | | | | |
|---|---|---|---|---|---|---|---|---|---|---|---|---|
| Active ingredient kg/ha | 0.25+ 0.75 | 0.75+ 0.25 | 2+1 | 1+2 | 1.5+ 1.5 | 2+2 | 0.25+ 0.75 | 0.75+ 0.25 | 2+1 | 1+2 | 1.5+ 1.5 | 2+2 |
| *Beta vulgaris* | 0 | 0 | 0 | 0 | 0 | 0 | 3 | 0 | 4 | 10 | 5 | 10 |
| *Avena fatua* | 82 | 95 | 100 | 100 | 100 | 100 | 80 | 80 | 100 | 100 | 100 | 100 |
| *Echinochloa crus-galli* | 98 | 100 | 100 | 100 | 100 | 100 | 85 | 100 | 100 | 100 | 100 | 100 |
| *Matricaria chamomilla* | 70 | 80 | 100 | 100 | 100 | 100 | 75 | 77 | 100 | 100 | 100 | 100 |

| Active ingredient | III + VII | | | | | | III + VIII | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 80 | 82 | 100 | 100 | 100 | 100 | 100 | 100 | 100 | 100 | 100 | 100 |
| *Echinochloa crus-galli* | 80 | 90 | 100 | 100 | 100 | 100 | 100 | 100 | 100 | 100 | 100 | 100 |
| *Matricaria chamomilla* | 60 | 70 | 100 | 100 | 100 | 100 | 62 | 70 | 100 | 100 | 100 | 100 |

| Active ingredient | III + XXXIII | | | | | | III + XXXIX | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 100 | 100 | 100 | 100 | 100 | 100 | 80 | 77 | 100 | 100 | 100 | 100 |
| *Echinochloa crus-galli* | 100 | 100 | 100 | 100 | 100 | 100 | 100 | 100 | 100 | 100 | 100 | 100 |
| *Matricaria chamomilla* | 57 | 65 | 100 | 100 | 100 | 100 | 85 | 86 | 100 | 100 | 100 | 100 |

| | III + XXXX | | | | | | III + XXXXI | | | | | |
|---|---|---|---|---|---|---|---|---|---|---|---|---|
| Active ingredient kg/ha | 0.25+ 0.75 | 0.75+ 0.25 | 2+1 | 1+2 | 1.5+ 1.5 | 2+2 | 0.25+ 0.75 | 0.75+ 0.25 | 2+1 | 1+2 | 1.5+ 1.5 | 2+2 |
| *Beta vulgaris* | 0 | 0 | 0 | 0 | 0 | 0 | 0 | 0 | 0 | 0 | 0 | 0 |
| *Avena fatua* | 96 | 90 | 100 | 100 | 100 | 100 | 98 | 90 | 100 | 100 | 100 | 100 |
| *Echinochloa crus-galli* | 100 | 100 | 100 | 100 | 100 | 100 | 70 | 89 | 100 | 100 | 100 | 100 |
| *Matricaria chamomilla* | 68 | 70 | 100 | 100 | 100 | 100 | 50 | 65 | 100 | 97 | 100 | 100 |

| Active ingredient | III + XXXXV | | | | | | III + XXXXVI | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 90 | 85 | 100 | 100 | 100 | 100 | 95 | 90 | 100 | 100 | 100 | 100 |
| *Echinochloa crus-galli* | 85 | 100 | 100 | 100 | 100 | 100 | 100 | 100 | 100 | 100 | 100 | 100 |
| *Matricaria chamomilla* | 60 | 66 | 100 | 100 | 100 | 100 | 58 | 65 | 100 | 100 | 100 | 100 |

| Active ingredient | II + LI | | | | | | II + LII | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 80 | 95 | 100 | 100 | 100 | 100 | 77 | 98 | 100 | 100 | 100 | 100 |
| *Echinochloa crus-galli* | 100 | 100 | 100 | 100 | 100 | 100 | 98 | 100 | 100 | 100 | 100 | 100 |
| *Matricaria chamomilla* | 70 | 80 | 100 | 100 | 100 | 100 | 66 | 75 | 100 | 100 | 100 | 100 |

| | II + LIII | | | | | | III + XXXXIX | | | | | |
|---|---|---|---|---|---|---|---|---|---|---|---|---|
| Active ingredient kg/ha | 0.25+ 0.75 | 0.75+ 0.25 | 2+1 | 1+2 | 1.5+ 1.5 | 2+2 | 0.25+ 0.75 | 0.75+ 0.25 | 2+1 | 1+2 | 1.5+ 1.5 | 2+2 |
| *Beta vulgaris* | 0 | 0 | 0 | 0 | 0 | 0 | 0 | 0 | 0 | 0 | 0 | 0 |
| *Avena fatua* | 80 | 95 | 100 | 100 | 100 | 100 | 80 | 82 | 100 | 100 | 100 | 100 |
| *Echinochloa crus-galli* | 100 | 100 | 100 | 100 | 100 | 100 | 95 | 95 | 100 | 100 | 100 | 100 |
| *Matricaria chamomilla* | 75 | 85 | 100 | 100 | 100 | 100 | 60 | 65 | 100 | 100 | 100 | 100 |

| Active ingredient | III + L | | | | | | III + LI | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 63 | 70 | 100 | 100 | 100 | 100 | 60 | 70 | 100 | 100 | 100 | 100 |
| *Echinochloa crus-galli* | 70 | 83 | 100 | 100 | 100 | 100 | 73 | 90 | 100 | 100 | 100 | 100 |
| *Matricaria chamomilla* | 70 | 75 | 100 | 100 | 100 | 100 | 70 | 75 | 100 | 100 | 100 | 100 |

| Active ingredient | III + LII | | | | | | III + LIII | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 60 | 75 | 100 | 100 | 100 | 100 | 60 | 70 | 100 | 100 | 100 | 100 |
| *Echinochloa crus-galli* | 70 | 90 | 100 | 100 | 100 | 100 | 74 | 90 | 100 | 100 | 100 | 100 |
| *Matricaria chamomilla* | 66 | 70 | 100 | 100 | 100 | 100 | 75 | 80 | 100 | 100 | 100 | 100 |

| Active ingredient | I + III + XXXXVI | | | | | |
|---|---|---|---|---|---|---|
| *Beta vulgaris* | 0 | 0 | 0 | 0 | 0 | 0 |
| *Avena fatua* | 80 | 76 | 75 | 100 | 100 | 100 |
| *Echinochloa crus-galli* | 100 | 90 | 86 | 100 | 100 | 100 |

-continued

| | | | | | | |
|---|---|---|---|---|---|---|
| *Matricaria chamomilla* | 63 | 70 | 65 | 100 | 100 | 100 |

0 = no damage
100 = complete destruction

EXAMPLE 14

In the greenhouse, various plants were treated at a growth height of from 5 to 27 cm with the following amounts of the following individual active ingredients and compositions thereof as emulsions or dispersions:

XXIV: O-(methylaminosulfonyl)-glycolic acid hexamethylene amide

LVI: O-(methylaminosulfonyl)-glycolic acid heptamethylene amide

LVIII: propionic acid-3,4-dichloroanilide each at rates of 0.25, 0.5, 0.75, 1, 1.25, 1.5, 2, 3 and 4 kg/ha, + 4 l/ha of 11E oil+)

XXIV+LVIII: 0.25+0.25, 0.5+0.5, 0.75+0.25, 0.25+0.75, 1+0.25, 0.25+1, 1+2, 2+1, 1+3, 3+1, 2+2, 1+0.5, 0.5+1, 0.75+0.75, 1+1, 0.5+1.5 1.5+0.5 and 1.5+1.5 kg/ha, +4 l/ha of 11E oil+)

+) product of the Sun Oil Company

After 2 to 3 weeks it was ascertained that, at the lower application rates, the compositions had a better herbicidal action then their components, combined with the same crop plant compatibility. The crop tolerance is still good at the higher application rates.

The results are given below:

| Active ingredient | LVI + 11e Oil | | | | | | | | |
|---|---|---|---|---|---|---|---|---|---|
| kg/ha | 0.25+ 4 | 0.5+ 4 | 0.75+ 4 | 1+ 4 | 1.25+ 4 | 1.5+ 4 | 2+ 4 | 3+ 4 | 4+ 4 |
| Crop plants: | | | | | | | | | |
| *Oryza sativa* | 0 | 0 | 0 | 0 | 0 | 0 | 0 | 5 | 10 |
| Unwanted plants: | | | | | | | | | |
| *Cyperus esculentus* | 0 | 5 | 10 | 15 | 20 | 30 | 40 | 50 | 60 |
| *Echinochloa crus-galli* | 30 | 35 | 50 | 75 | 80 | 85 | 90 | 97 | 100 |
| *Alisma plantago-aquatica* | 0 | 0 | 0 | 5 | 10 | 15 | 20 | 25 | 32 |

| Active ingredient | XXIV + 11e Oil | | | | | | | | |
|---|---|---|---|---|---|---|---|---|---|
| Oryza sativa | 0 | 0 | 0 | 0 | 0 | 0 | 0 | 5 | 10 |
| *Cyperus esculentus* | 10 | 20 | 30 | 40 | 45 | 50 | 65 | 80 | 95 |
| *Echinochloa crus-galli* | 30 | 40 | 50 | 70 | 75 | 80 | 90 | 98 | 100 |
| *Alisma plantago-aquatica* | 0 | 5 | 10 | 15 | 20 | 25 | 30 | 35 | 40 |

| Active ingredient | LVIII + 11e Oil | | | | | | | | |
|---|---|---|---|---|---|---|---|---|---|
| kg/ha | 0.25+ 4 | 0.5+ 4 | 0.75+ 4 | 1+ 4 | 1.25+ 4 | 1.5+ 4 | 2+ 4 | 3+ 4 | 4+ 4 |
| *Oryza sativa* | 0 | 0 | 0 | 0 | 0 | 0 | 0 | 10 | 30 |
| *Cyperus esculentus* | 0 | 0 | 0 | 0 | 3 | 5 | 10 | 20 | 35 |
| *Echinochloa crus-galli* | 10 | 18 | 25 | 30 | 35 | 45 | 60 | 90 | 100 |
| *Alisma plantago-aquatica* | 3 | 5 | 7 | 10 | 15 | 25 | 35 | 55 | 70 |

| Active ingredient | XXIV + LVIII | | | | | | | | | |
|---|---|---|---|---|---|---|---|---|---|---|
| kg/ha | 0.25+ 0.25+ 4 | 0,5+ 0.5+ 4 | 0.75+ 0.25+ 4 | 0,25+ 0.75+ 4 | 1+ 0.25+ 4 | 0,25+ 1+ 4 | 1+ 0.5+ 4 | 0.5+ 1+ 4 | 0.75+ 0.75+ 4 | 1+ 1+ 4 |
| *Oryza sativa* | 0 | 0 | 0 | 0 | 0 | 0 | 0 | 0 | 0 | 0 |
| *Cyperus esculentus* | 50 | 60 | 70 | 53 | 80 | 54 | 80 | 60 | 70 | 80 |
| *Echinochloa crus-galli* | 78 | 95 | 98 | 95 | 100 | 100 | 100 | 100 | 100 | 100 |
| *Alisma plantago-aquatica* | 45 | 50 | 55 | 50 | 59 | 50 | 60 | 57 | 59 | 65 |

| kg/ha | 0.5+ 1.5+ 4 | 1.5+ 0.5+ 4 | 1.5+ 1.5+ 4 | 1+ 2+ 4 | 2+ 1+ 4 | 1+ 3+ 4 | 3+ 1+ 4 | 2+ 2+ 4 |
|---|---|---|---|---|---|---|---|---|
| *Oryza sativa* | 0 | 0 | 0 | 0 | 0 | 0 | 5 | 0 |
| *Cyperus esculentus* | 70 | 90 | 95 | 90 | 100 | 100 | 100 | 100 |
| *Echinochloa crus-galli* | 100 | 100 | 100 | 100 | 100 | 100 | 100 | 100 |
| *Alisma plantago-aquatica* | 70 | 70 | 90 | 90 | 80 | 100 | 85 | 100 |

EXAMPLE 15

In the greenhouse, various plants were treated at a growth height of from 3 to 18 cm with the following amounts of the following individual active ingredients and compositions thereof as emulsions or dispersions:

I: 1-phenyl-4-amino-5-chloropyridazone-(6)
0.25, 0.5, 1, 1.5, 2, 2.5 and 3 kg/ha;

II: O-(isopropylaminosulfonyl)-glycolic acid-N-butyn-1-yl-3-anilide
0.25, 0.5, 0.75, 1, 2 and 3 kg/ha III: O-(methylaminosulfonyl)-glycolic acid-N-isopropylanilide
0.25, 0.5, 0.75, 1, 2 and 3 kg/ha XXXII: benzamidooxyacetic acid
0.25, 0.5, 0.75, 1, 2 and 3 kg/ha LIV: N-methylacetanilido-d-isopropyl sulfite
0.5, 1, 1.5, 2 and 3 kg/ha II+XXXII, and III+XXXII each at rates of 0.25+0.75, 0.75+0.25, and 0.5+0.5 kg/ha I+LIV: 0.5+0.5, 1+1, and 1.5+1.5 kg/ha.

After 2 to 3 weeks it was ascertained that, at the lower application rates, the compositions had a better herbicidal action than their components, combined with the same crop plant compatibility. The crop tolerance was still good at the higher application rates.

The results are given below:

| Active ingredient | I | II |
|---|---|---|

-continued

| kg/ha | 0.25 | 0.5 | 1 | 2 | 3 | 0.25 | 0.5 | 0.75 | 1 | 2 | 3 |
|---|---|---|---|---|---|---|---|---|---|---|---|
| Crop plants: | | | | | | | | | | | |
| *Beta vulgaris* | 0 | 0 | 0 | 0 | 0 | 0 | 0 | 0 | 0 | 0 | 0 |
| Unwanted plants: | | | | | | | | | | | |
| *Kochia scoparia* | 7 | 10 | 20 | 40 | 80 | 5 | 12 | 15 | 20 | 40 | 50 |
| *Chenopodium album* | 20 | 30 | 45 | 65 | 90 | 5 | 15 | 20 | 40 | 55 | 60 |
| *Echinochloa crus-galli* | 10 | 15 | 25 | 53 | 80 | 30 | 45 | 65 | 70 | 80 | 95 |

| Active ingredient | I | | III | | | | | |
|---|---|---|---|---|---|---|---|---|
| kg/ha | 1.5 | 2.5 | 0.25 | 0.5 | 0.75 | 1 | 2 | 3 |
| *Beta vulgaris* | 0 | 0 | 0 | 0 | 0 | 0 | 0 | 0 |
| *Kochia scoparia* | 30 | 65 | 0 | 5 | 10 | 15 | 30 | 40 |
| *Chenopodium album* | 50 | 80 | 4 | 10 | 20 | 30 | 40 | 45 |
| *Echinochloa crus-galli* | 40 | 70 | 30 | 45 | 65 | 70 | 80 | 90 |

| Active ingredient | XXXII | | | | | | LIV | | | | |
|---|---|---|---|---|---|---|---|---|---|---|---|
| kg/ha | 0,25 | 0.5 | 0.75 | 1 | 2 | 3 | 0.5 | 1 | 1.5 | 2 | 3 |
| *Beta vulgaris* | 0 | 0 | 0 | 0 | 0 | 10 | 0 | 0 | 0 | 0 | 5 |
| *Kochia scoparia* | 20 | 30 | 35 | 40 | 80 | 90 | 0 | 7 | 10 | 20 | 30 |
| *Chenopodium album* | 10 | 20 | 25 | 30 | 53 | 70 | 0 | 5 | 20 | 30 | 35 |
| *Echinochloa crus-galli* | 0 | 4 | 6 | 10 | 20 | 30 | 20 | 50 | 60 | 80 | 90 |

| Active ingredient | II + XXXII | | | III + XXXII | | | I + LIV | | |
|---|---|---|---|---|---|---|---|---|---|
| kg/ha | 0.25+ 0.75 | 0.75+ 0.25 | 0.5+ 0.5 | 0.25+ 0.75 | 0.75+ 0.25 | 0.5+ 0.5 | 0.5+ 0.5 | 1+ 1 | 1.5+ 1.5 |
| *Beta vulgaris* | 0 | 0 | 0 | 0 | 0 | 0 | 0 | 0 | 0 |
| *Kochia scoparia* | 82 | 75 | 83 | 74 | 70 | 76 | 51 | 69 | 85 |
| *Chenopodium album* | 70 | 70 | 75 | 70 | 70 | 70 | 70 | 90 | 100 |
| *Echinochloa crus-galli* | 78 | 98 | 90 | 76 | 98 | 90 | 75 | 100 | 100 |

0 = no damage
100 = complete destruction

EXAMPLE 16

In the greenhouse, various plants were treated at a growth height of from 3 to 18 cm with the following amounts of the following individual active ingredients and compositions thereof as dispersions:

I: 1-phenyl-4-amino-5-chloropyridazone-(6)
0.5, 1, 1.5, 1.86, 2, 2.5, 3, 4 and 5 kg/ha, III: O-(methylaminosulfonyl)-glycolic acid-N-isopropylanilide
0.5, 0.75, 1, 1.25, 1.33, 1.5, 1.66, 2, 3, 4 and 5 kg/ha, XXIV: O-(methylaminosulfonyl)-glycolic acid hexamethylene amide,
0.25, 0.375, 0.5, 0.67, 0.725, 0.75, 0.834, 1, 1.5, 2, 2.5 3, 3.5 4 and 5 kg/ha, I+XXIV+III: 1+0.5+0.5, 1.5+0.75+0.75, 2+1+1, 2+0.5+1.5, 1.86+0.375+0.75, 2.5+0.5+1, 3+0.725+1.25, 3+0.5+1.5, 2+0.67+1.33, 2.5+0.834+1.66, and 2+1+2 kg/ha.

After 2 to 3 weeks it was ascertained that the composition had a better herbicidal action than its components, combined with superior crop plant compatibility.

The results are given below:

| Active ingredient | I | | | | | | | | |
|---|---|---|---|---|---|---|---|---|---|
| kg/ha | 0.5 | 1 | 1.5 | 1.86 | 2 | 2.5 | 3 | 4 | 5 |
| Crop plants: | | | | | | | | | |
| *Beta vulgaris* | 0 | 0 | 0 | 0 | 0 | 0 | 0 | 10 | 20 |
| Unwanted plants: | | | | | | | | | |
| *Avena fatua* | 5 | 13 | 15 | 22 | 25 | 35 | 40 | 65 | 90 |
| *Echinochloa crus-galli* | 15 | 25 | 40 | 49 | 53 | 70 | 80 | 90 | 100 |
| *Stellaria media* | 20 | 40 | 60 | 73 | 80 | 90 | 95 | 100 | 100 |
| *Galium aparine* | 20 | 40 | 50 | 65 | 70 | 75 | 80 | 90 | 100 |
| *Chenopodium album* | 30 | 45 | 50 | 61 | 65 | 80 | 90 | 100 | 100 |
| *Alopecurus myosuroides* | 5 | 35 | 85 | 88 | 90 | 95 | 100 | 100 | 100 |
| *Lamium amplexicaule* | 10 | 20 | 25 | 35 | 40 | 50 | 60 | 85 | 100 |

| Active ingredient | III | | | | | | | | | | |
|---|---|---|---|---|---|---|---|---|---|---|---|
| kg/ha | 0.5 | 0.75 | 1 | 1.25 | 1.33 | 1.5 | 1.66 | 2 | 3 | 4 | 5 |
| *Beta vulgaris* | 0 | 0 | 0 | 0 | 0 | 0 | 0 | 0 | 0 | 10 | 14 |
| *Avena fatua* | 25 | 45 | 50 | 55 | 57 | 60 | 62 | 65 | 70 | 72 | 80 |
| *Echinochloa crus-galli* | 45 | 65 | 70 | 72 | 73 | 75 | 76 | 80 | 90 | 100 | 100 |
| *Stellaria media* | 5 | 8 | 15 | 20 | 23 | 25 | 25 | 30 | 40 | 50 | 60 |
| *Galium aparine* | 10 | 13 | 15 | 17 | 18 | 20 | 20 | 25 | 41 | 45 | 50 |
| *Chenopodium album* | 10 | 20 | 30 | 32 | 34 | 35 | 37 | 40 | 45 | 55 | 65 |
| *Alopecurus myosuroides* | 50 | 60 | 90 | 95 | 98 | 100 | 100 | 100 | 100 | 100 | 100 |
| *Lamium amplexicaule* | 5 | 10 | 15 | 18 | 19 | 20 | 22 | 25 | 35 | 40 | 55 |

| Active ingredient | XXIV | | | |
|---|---|---|---|---|
| kg/ha | 0.25 | 0.375 | 0.5 | 0.67 |
| Crop plants: | | | | |
| *Beta vulgaris* | 0 | 0 | 0 | 0 |
| Unwanted plants: | | | | |
| *Avena fatua* | 18 | 25 | 30 | 32 |
| *Echinochloa crus-galli* | 30 | 35 | 40 | 41 |
| *Stellaria media* | 10 | 16 | 20 | 23 |
| *Galium aparine* | 10 | 15 | 20 | 22 |
| *Chenopodium album* | 7 | 10 | 15 | 17 |
| *Alopecurus myosuroides* | 35 | 44 | 50 | 57 |
| *Lamium amplexicaule* | 0 | 2 | 5 | 10 |

-continued

| Active Ingredient | I + XXIV + III | | | | | | | | | | |
|---|---|---|---|---|---|---|---|---|---|---|---|
| kg/ha | 1+ 0.5+ 0.5 | 1.5 0.75+ 0.75 | 2+ 1+ 1 | 2+ 0.5+ 1.5 | 1.36+ 0.375+ 0.75 | 2.5+ 0.5+ 1 | 3+ 0.725+ 1.25 | 3+ 0.5+ 1.5 | 2+ 0.67+ 1.33 | 2.5+ 0.834+ 1.66 | 2+ 1+ 2 |
| *Beta vulgaris* | 0 | 0 | 0 | 0 | 0 | 0 | 0 | 0 | 0 | 0 | 0 |
| *Avena fatua* | 100 | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 |
| *Stellaria media* | 100 | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 | 100 |
| *Chenopodium album* | 100 | 100 | 100 | 100 | 100 | 100 | 100 | 100 | 100 | 100 | 100 |
| *Alopecurus myosuroides* | 100 | 100 | 100 | 100 | 100 | 100 | 100 | 100 | 100 | 100 | 100 |
| *Lamium amplexicaule* | 70 | 90 | 100 | 100 | 88 | 100 | 100 | 100 | 100 | 100 | 100 |

0 = no damage
100 = complete destruction

EXAMPLE 17

In the greenhouse, various plants were treated at a growth height of from 4 to 18 cm with the following amounts of the following individual active ingredients and compositions thereof as dispersions or emulsions:

I: 1-phenyl-4-amino-5-chloropyridazone-(6)
0.5, 1, 1.5, 2, 2.5, 3, 4, 5 and 6 kg/ha, II: O-(isopropylaminosulfonyl)-glycolic acid-N-butyn-1-yl-3-anilide
0.5, 1, 1.5, 2, 4 and 6 kg/ha, III: O-(methylaminosulfonyl)-glycolic acid-N-isopropylanilide
0.25, 0.5, 0.75, 1, 1.5, 2, 2.5, 3, 4, 5, and 6 kg/ha, XIII: 3-(N-m-trifluoromethylphenylcarbamoyloxy)-(p-methylphenyl)-methylcarbamate
0.5, 1, 1.5, 2, 4 and 6 kg/ha;

XXXXVI: 2,3-dihydro-3,3-dimethyl-2-ethoxybenzofuran-5-yl-N-methyl-N-acetylamino sulfonate
0.25, 0.5, 0.75, 1, 1.5, 2, 3, 4 and 6 kg/ha, I+III+XXXXVI: 1.5+0.75+0.75, 2+1+1, 0.5+0.25+0.25, 1+0.5+0.5, 2+1.5+0.5, 2+0.5+1.5, 3+1.5+1.5, 3+1+2 and 3+2+1 kg/ha, I+III+II: 2+1+1, 2+1.5+0.5, 2+0.5+1.5 and 3+1+2 kg/ha;

I+III+XIII: 2+1+1, and 3+2+1 kg/ha.

After 2 to 3 weeks it was ascertained that the compositions had a better herbicidal action than their components, combined with superior crop plant compatibility.

The results are given below:

| Active ingredient | I | | | | | | | | |
|---|---|---|---|---|---|---|---|---|---|
| kg/ha | 0.5 | 1 | 1.5 | 2 | 2.5 | 3 | 4 | 5 | 6 |
| Crop plants: | | | | | | | | | |
| *Beta vulgaris* | 0 | 0 | 0 | 0 | 0 | 0 | 10 | 15 | 20 |
| Unwanted plants: | | | | | | | | | |
| *Avena fatua* | 5 | 13 | 15 | 25 | 35 | 40 | 65 | 90 | 100 |
| *Echinochloa crus-galli* | 15 | 25 | 40 | 53 | 70 | 80 | 90 | 100 | 100 |
| *Stellaria media* | 20 | 40 | 60 | 80 | 90 | 95 | 100 | 100 | 100 |
| *Galium aparine* | 20 | 40 | 50 | 70 | 75 | 80 | 90 | 100 | 100 |
| *Chenopodium album* | 30 | 45 | 50 | 65 | 80 | 90 | 100 | 100 | 100 |
| *Alopecurus myosuroides* | 5 | 35 | 85 | 90 | 95 | 100 | 100 | 100 | 100 |
| *Lamium amplexicaule* | 10 | 20 | 25 | 40 | 50 | 60 | 85 | 95 | 100 |

| Active ingredient | II | | | | | |
|---|---|---|---|---|---|---|
| kg/ha | 0.5 | 1 | 1.5 | 2 | 4 | 6 |
| *Beta vulgaris* | 0 | 0 | 0 | 0 | 10 | 20 |
| *Avena fatua* | 30 | 50 | 55 | 60 | 70 | 95 |
| *Echinochloa crus-galli* | 45 | 70 | 78 | 80 | 100 | 100 |
| *Stellaria media* | 10 | 15 | 25 | 30 | 40 | 55 |
| *Galium aparine* | 10 | 20 | 24 | 28 | 46 | 60 |
| *Chenopodium album* | 15 | 40 | 50 | 55 | 70 | 85 |
| *Alopecurus myosuroides* | 45 | 90 | 95 | 100 | 100 | 100 |
| *Lamium amplexicaule* | 7 | 15 | 30 | 40 | 60 | 75 |

| Active ingredient | III | | | | | | | | | | |
|---|---|---|---|---|---|---|---|---|---|---|---|
| kg/ha | 0.25 | 0.5 | 0.75 | 1 | 1.5 | 2 | 2.5 | 3 | 4 | 5 | 6 |
| *Beta vulgaris* | 0 | 0 | 0 | 0 | 0 | 0 | 0 | 0 | 10 | 14 | 20 |
| *Avena fatua* | 15 | 25 | 45 | 50 | 60 | 65 | 68 | 70 | 72 | 80 | 90 |
| *Echinochloa crus-galli* | 30 | 45 | 65 | 70 | 75 | 80 | 85 | 90 | 100 | 100 | 100 |
| *Stellaria media* | 0 | 5 | 8 | 15 | 25 | 30 | 35 | 40 | 50 | 60 | 80 |
| *Galium aparine* | 5 | 10 | 13 | 15 | 20 | 25 | 35 | 41 | 45 | 50 | 75 |
| *Chenopodium album* | 4 | 10 | 20 | 30 | 35 | 40 | 43 | 45 | 55 | 65 | 80 |
| *Alopecurus myosuroides* | 30 | 50 | 60 | 90 | 100 | 100 | 100 | 100 | 100 | 100 | 100 |
| *Lamium amplexcaule* | 0 | 5 | 10 | 15 | 20 | 25 | 30 | 35 | 40 | 55 | 65 |

| Active ingredient | XIII | | | | | |
|---|---|---|---|---|---|---|
| kg/ha | 0.5 | 1 | 1.5 | 2 | 4 | 6 |
| *Beta vulgaris* | 0 | 0 | 0 | 0 | 25 | 30 |
| *Avena fatua* | 10 | 15 | 30 | 40 | 60 | 80 |
| *Echinochloa crus-galli* | 16 | 35 | 65 | 80 | 98 | 100 |
| *Stellaria media* | 70 | 95 | 100 | 100 | 100 | 100 |
| *Galium aparine* | 28 | 55 | 60 | 70 | 100 | 100 |
| *Chenopodium album* | 60 | 100 | 100 | 100 | 100 | 100 |
| *Alopecurus myosuroides* | 5 | 50 | 55 | 60 | 80 | 95 |
| *Lamium amplexicaule* | 60 | 90 | 95 | 100 | 100 | 100 |

-continued

| Active ingredient | XXXXVI | | | | | | | | |
|---|---|---|---|---|---|---|---|---|---|
| kg/ha | 0.25 | 0.5 | 0.75 | 1 | 1.5 | 2 | 3 | 4 | 6 |
| *Beta vulgaris* | 0 | 0 | 0 | 0 | 0 | 0 | 10 | 15 | 25 |
| *Avena fatua* | 15 | 25 | 40 | 55 | 70 | 80 | 90 | 100 | 100 |
| *Echinochloa crus-galli* | 25 | 35 | 50 | 60 | 70 | 85 | 95 | 100 | 100 |
| *Stellaria media* | 20 | 30 | 50 | 65 | 90 | 96 | 100 | 100 | 100 |
| *Galium aparine* | 10 | 20 | 30 | 45 | 70 | 75 | 85 | 97 | 100 |
| *Chenopodium album* | 20 | 25 | 40 | 60 | 70 | 90 | 98 | 100 | 100 |
| *Alopecurus myosuroides* | 30 | 35 | 50 | 70 | 95 | 100 | 100 | 100 | 100 |
| *Lamium amplexicaule* | 20 | 30 | 40 | 50 | 75 | 85 | 95 | 100 | 100 |

| Active ingredient | I + III + XXXXVI | | | | | | | | |
|---|---|---|---|---|---|---|---|---|---|
| kg/ha | 1.5+ 0.75+ 0.75 | 2+1+1 | 0.5+ 0.25+ 0.25 | 1+ 0.5+ 0.5 | 2+ 1.5+ 0.5 | 2+ 0.5+ 1.5 | 3+ 1.5+ 1.5 | 3+1+2 | 3+2+1 |
| *Beta vulgaris* | 0 | 0 | 0 | 0 | 0 | 0 | 0 | 0 | 0 |
| *Avena fatua* | 100 | 100 | 75 | 100 | 100 | 100 | 100 | 100 | 100 |
| *Echinochloa crus-galli* | 100 | 100 | 100 | 100 | 100 | 100 | 100 | 100 | 100 |
| *Stellaria media* | 100 | 100 | 80 | 100 | 100 | 100 | 100 | 100 | 100 |
| *Galium aparine* | 100 | 100 | 80 | 100 | 100 | 100 | 100 | 100 | 100 |
| *Chenopodium album* | 100 | 100 | 95 | 100 | 100 | 100 | 100 | 100 | 100 |
| *Alopecurus myosuroides* | 100 | 100 | 100 | 100 | 100 | 100 | 100 | 100 | 100 |
| *Lamium amplexicaule* | 100 | 100 | 70 | 95 | 100 | 100 | 100 | 100 | 100 |

| Active ingredient | I + III + II | | | | I + III + XIII | |
|---|---|---|---|---|---|---|
| kg/ha | 2+1+1 | 2+1.5 +0.5 | 2+0.5 +1.5 | 3+1+2 | 2+1+1 | 3+2+1 |
| Crop plants: | | | | | | |
| *Beta vulgaris* | 0 | 0 | 0 | 0 | 0 | 0 |
| Unwanted plants: | | | | | | |
| *Avena fatua* | 100 | 100 | 100 | 100 | 100 | 100 |
| *Echinochloa crus-galli* | 100 | 100 | 100 | 100 | 100 | 100 |
| *Stellaria media* | 100 | 100 | 100 | 100 | 100 | 100 |
| *Galium aparine* | 100 | 100 | 100 | 100 | 100 | 100 |
| *Chenopodium album* | 100 | 100 | 100 | 100 | 100 | 100 |
| *Alopecurus myosuroides* | 100 | 100 | 100 | 100 | 100 | 100 |
| *Lamium amplexicaule* | 100 | 100 | 100 | 100 | 100 | 100 |

0 = no damage
100 = complete destruction

EXAMPLE 18

In the greenhouse, various plants were treated at a growth height of from 2 to 17 cm with the following amounts of the following individual active ingredients and compositions thereof as suspensions or pastes:

I: 1-phenyl-4-amino-5-chloropyridazone-(6)
0.5, 1, 1.25, 1.5, 2, 2.5, 3, 3.5, 4, 5 and 6 kg/ha, II: O-(isopropylaminosulfonyl)-glycolic acid-N-butyn-1-yl-3-anilide
1.5, 2, 3, 4 and 6 kg/ha, III: O-(methylaminosulfonyl)-glycolic acid-N-isopropylanilide
0.75, 1, 1.5, 2, 3, 4, 5 and 6 kg/ha, XXIV: O-(methylaminosulfonyl)-glycolic acid hexamethylene amide
0.5, 0.75, 1, 1.5, 2, 3, 3.5 and 4 kg/ha, XXV: O-(ethylaminosulfonyl)-glycolic acid hexamethylene amide
0.5, 1, 1.5, 2, 3 and 4 kg/ha, LIV: N-methylacetanilido-α-isopropylsulfite
1, 1.5, 2, 3 and 4 kg/ha, LXI 3-(isopropylaminosulfonyloxyacetyl)-3-azabicyclo-(3,2,2)-nonane,
1.5 and 4 kg/ha, I+II 2.5+1.5, 2+2 and 3+3 kg/ha, I+III 1.25+0.75, 1+1, 2+1, 2+2, 1.5+1.5, 2.5+1.5, 3+3, 3+1, 3+2, 4+1 and 4+2 kg/ha, I+XXIV: 0.5+0.5, 1+1, 1.25+0.75, 1.5+1.5, 2+1, 2+2, 2.5+0.5, 2.5+1.5, 3+1, 3.5+0.5 and 3+0.5 kg/ha, I+XXV: 2+1, 2+2, 2.5+0.5, 2.5+1.5, 3+1, and 3.5+0.5 kg/ha, I+LIV: 2+1, 2+2, 2.5+1.5 and 3+1 kg/ha, I+LXI: 2.5+1.5 kg/ha.

After 2 to 3 weeks it was ascertained that the compositions had a better herbicidal action than their components, combined with superior crop plant compatibility. The results are given below:

| Active ingredient | I | | | | | | | | | | |
|---|---|---|---|---|---|---|---|---|---|---|---|
| kg/ha | 0.5 | 1 | 1.25 | 1.5 | 2 | 2.5 | 3 | 3.5 | 4 | 5 | 6 |
| Crop plants: | | | | | | | | | | | |
| *Beta vulgaris* | 0 | 0 | 0 | 0 | 0 | 0 | 0 | 5 | 10 | 15 | 20 |
| Unwanted plants: | | | | | | | | | | | |
| *Avena fatua* | 5 | 13 | 15 | 15 | 25 | 35 | 40 | 55 | 65 | 90 | 100 |
| *Echinochloa crus-galli* | 15 | 25 | 35 | 40 | 53 | 70 | 80 | 85 | 90 | 100 | 100 |
| *Stellaria media* | 20 | 40 | 50 | 60 | 80 | 90 | 95 | 100 | 100 | 100 | 100 |
| *Galium aparine* | 20 | 40 | 45 | 50 | 70 | 75 | 80 | 87 | 90 | 100 | 100 |
| *Chenopodium album* | 30 | 45 | 48 | 50 | 65 | 80 | 90 | 97 | 100 | 100 | 100 |
| *Alopecurus myosuroides* | 5 | 35 | 60 | 85 | 90 | 95 | 100 | 100 | 100 | 100 | 100 |
| *Lamium amplexicaule* | 10 | 20 | 23 | 25 | 40 | 50 | 60 | 70 | 85 | 95 | 100 |

| Active ingredient | II | | | | | III | | | | | | | |
|---|---|---|---|---|---|---|---|---|---|---|---|---|---|
| kg/ha | 1.5 | 2 | 3 | 4 | 6 | 0.75 | 1 | 1.5 | 2 | 3 | 4 | 5 | 6 |
| *Beta vulgaris* | 0 | 0 | 0 | 10 | 20 | 0 | 0 | 0 | 0 | 0 | 10 | 14 | 20 |
| *Avena fatua* | 55 | 60 | 65 | 70 | 95 | 45 | 50 | 60 | 65 | 70 | 72 | 80 | 90 |

-continued

| | | | | | | | | | | | | | |
|---|---|---|---|---|---|---|---|---|---|---|---|---|---|
| *Echinochloa crus-galli* | 78 | 80 | 95 | 100 | 100 | 65 | 70 | 75 | 80 | 90 | 100 | 100 | 100 |
| *Stellaria media* | 25 | 30 | 35 | 40 | 55 | 8 | 15 | 25 | 30 | 40 | 50 | 60 | 80 |
| *Galium aparine* | 24 | 28 | 40 | 46 | 60 | 13 | 15 | 20 | 25 | 41 | 45 | 50 | 75 |
| *Chenopodium album* | 50 | 55 | 60 | 70 | 85 | 20 | 30 | 35 | 40 | 45 | 55 | 65 | 80 |
| *Alopecurus myosuroides* | 95 | 100 | 100 | 100 | 100 | 60 | 90 | 100 | 100 | 100 | 100 | 100 | 100 |
| *Lamium amplexicaule* | 30 | 40 | 50 | 60 | 75 | 10 | 15 | 20 | 25 | 35 | 40 | 55 | 65 |

| Active ingredient | XXIV | | | | | | | | LXI | |
|---|---|---|---|---|---|---|---|---|---|---|
| kg/ha | 0.5 | 0.75 | 1 | 1.5 | 2 | 3 | 3.5 | 4 | 1.5 | 4 |
| *Beta vulgaris* | 0 | 0 | 0 | 0 | 5 | 10 | 13 | 15 | 0 | 5 |
| *Avena fatua* | 30 | 35 | 45 | 60 | 70 | 80 | 90 | 95 | 55 | 85 |
| *Echinochloa crus-galli* | 40 | 50 | 70 | 80 | 90 | 98 | 100 | 100 | 80 | 100 |
| *Stellaria media* | 20 | 30 | 40 | 45 | 60 | 70 | 80 | 85 | 20 | 60 |
| *Galium aparine* | 20 | 25 | 35 | 40 | 50 | 65 | 70 | 75 | 10 | 50 |
| *Chenopodium album* | 15 | 20 | 25 | 35 | 45 | 60 | 73 | 80 | 15 | 50 |
| *Alopecurus myosuroides* | 50 | 65 | 75 | 90 | 95 | 100 | 100 | 100 | 90 | 100 |
| *Lamium amplexicaule* | 5 | 15 | 20 | 35 | 45 | 55 | 58 | 60 | 15 | 50 |

| Active ingredient | XXV | | | | | | LIV | | | | |
|---|---|---|---|---|---|---|---|---|---|---|---|
| kg/ha | 0.5 | 1 | 1.5 | 2 | 3 | 4 | 1 | 1.5 | 2 | 3 | 4 |
| *Beta vulgaris* | 0 | 0 | 0 | 5 | 10 | 15 | 0 | 0 | 0 | 5 | 15 |
| *Avena fatua* | 20 | 40 | 60 | 70 | 80 | 95 | 35 | 40 | 50 | 65 | 75 |
| *Echinochloa crus-galli* | 35 | 60 | 85 | 95 | 100 | 100 | 50 | 60 | 80 | 90 | 100 |
| *Stellaria media* | 15 | 25 | 35 | 50 | 65 | 80 | 25 | 28 | 30 | 50 | 60 |
| *Galium aparine* | 10 | 20 | 35 | 45 | 65 | 80 | 0 | 10 | 20 | 30 | 40 |
| *Chenopodium album* | 10 | 20 | 30 | 40 | 50 | 70 | 5 | 20 | 30 | 35 | 55 |
| *Alopecurus myosuroides* | 40 | 65 | 80 | 90 | 100 | 100 | 50 | 70 | 85 | 95 | 100 |
| *Lamium amplexicaule* | 5 | 7 | 10 | 25 | 35 | 50 | 15 | 20 | 25 | 45 | 60 |

| | I + III | | | | | | | | | | |
|---|---|---|---|---|---|---|---|---|---|---|---|
| Active Ingredient kg/ha | 1.25+ 0.75 | 1+1 | 2+1 | 2+2 | 1.5+ 1.5 | 2.5+ 1.5 | 3+3 | 3+1 | 3+2 | 4+1 | 4+2 |
| *Beta vulgaris* | 0 | 0 | 0 | 0 | 0 | 0 | 0 | 0 | 0 | 10 | 10 |
| *Avena fatua* | 100 | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 |
| *Stellaria media* | 98 | 95 | 100 | 100 | 100 | 100 | 100 | 100 | 100 | 100 | 100 |
| *Galium aparine* | 100 | 100 | 100 | 100 | 100 | 100 | 100 | 100 | 100 | 100 | 100 |
| *Chenopodium album* | 100 | 100 | 100 | 100 | 100 | 100 | 100 | 100 | 100 | 100 | 100 |
| *Alopecurus myosuroides* | 100 | 100 | 100 | 100 | 100 | 100 | 100 | 100 | 100 | 100 | 100 |
| *Lamium amplexicaule* | 75 | 75 | 95 | 100 | 85 | 100 | 100 | 100 | 100 | 100 | 100 |

| | I + II | | | I + XXIV | | | | | | |
|---|---|---|---|---|---|---|---|---|---|---|
| Active ingredient kg/ha | 2.5+ 1.5 | 2+2 | 3+3 | 0.5+ 0.5 | 1+1 | 1.25+ 0.75 | 1.5+ 1.5 | 2+1 | 2+2 | 2.5+ 0.5 |
| *Beta vulgaris* | 0 | 0 | 0 | 0 | 0 | 0 | 0 | 0 | 5 | 0 |
| *Avena fatua* | 100 | 100 | 100 | 75 | 100 | 90 | 100 | 100 | 100 | 100 |
| *Echinochloa crus-galli* | 100 | 100 | 100 | 95 | 100 | 100 | 100 | 100 | 100 | 100 |
| *Stellaria media* | 100 | 100 | 100 | 80 | 100 | 100 | 100 | 100 | 100 | 100 |
| *Galium aparine* | 100 | 100 | 100 | 80 | 100 | 100 | 100 | 100 | 100 | 100 |
| *Chenopodium album* | 100 | 100 | 100 | 85 | 100 | 100 | 100 | 100 | 100 | 100 |
| *Alopecurus myosuroides* | 100 | 100 | 100 | 95 | 100 | 100 | 100 | 100 | 100 | 100 |
| *Lamium amplexicaule* | 100 | 100 | 100 | 60 | 80 | 80 | 100 | 100 | 100 | 95 |

| | I + XXIV | | | | I + XXV | | | | | |
|---|---|---|---|---|---|---|---|---|---|---|
| Active ingredient kg/ha | 2.5+ 1.5 | 3+1 | 3.5+ 0.5 | 3+ 0.5 | 2+1 | 2+2 | 2.5+ 0.5 | 2.5+ 1.5 | 3+1 | 3.5+ 0.5 |
| *Beta vulgaris* | 0 | 0 | 5 | 0 | 0 | 5 | 0 | 0 | 0 | 5 |
| *Avena fatua* | 100 | 100 | 100 | 100 | 100 | 100 | 95 | 100 | 100 | 100 |
| *Echinochloa crus-galli* | 100 | 100 | 100 | 100 | 100 | 100 | 100 | 100 | 100 | 100 |
| *Stellaria media* | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 |
| *Chenopodium album* | 100 | 100 | 100 | 100 | 100 | 100 | 100 | 100 | 100 | 100 |
| *Alopecurus myosuroides* | 100 | 100 | 100 | 100 | 100 | 100 | 100 | 100 | 100 | 100 |
| *Lamium amplexicaule* | 100 | 100 | 100 | 100 | 90 | 100 | 95 | 100 | 100 | 100 |

| | I + LIV | | | | I + LXI |
|---|---|---|---|---|---|
| Acive Ingredient kg/ha | 2+1 | 2+2 | 2.5+ 1.5 | 3+1 | 2.5+1.5 |
| *Beta vulgaris* | 0 | 0 | 0 | 0 | 0 |
| *Avena fatua* | 100 | 100 | 100 | 100 | 100 |
| *Echinochloa crus-galli* | 100 | 100 | 100 | 100 | 100 |
| *Stellaria media* | 100 | 100 | 100 | 100 | 100 |
| *Galium aparine* | 100 | 100 | 100 | 100 | 100 |
| *Chenopodium album* | 100 | 100 | 100 | 100 | 100 |
| *Alopecurus myosuroides* | 100 | 100 | 100 | 100 | 100 |
| *Lamium amplexicaule* | 95 | 100 | 100 | 100 | 100 |

0 = no damage
100 = complete destruction

EXAMPLE 19

In the greenhouse, loamy sandy soil was filled into pots and sown with various seeds. The soil prepared in this manner was then treated with the following amounts of the following individual active ingredients and compositions thereof as emulsions or dispersions:

I: 1-phenyl-4-amino-5-chloropyridazone-(6)
0.5, 1, 1.5, 1.86, 2.5, 3, 4 and 5 kg/ha, III: O-(methylaminosulfonyl)-glycolic acid-N-isopropylanilide,
0.5, 0.75, 1, 1.25, 1.33, 1.5, 1.66, 2, 3, 4 and 5 kg/ha, IV: 2,3-dichloroallyl N,N-diisopropylthiolcarbamate
0.25, 0.5, 0.75, 1, 1.5, 2 and 4 kg/ha, XXIV: O-(methylaminosulfonyl)-glycolic acid hexamethylene amide, 0.25, 0.375, 0.5, 0.67, 0.725, 0.75, 0.834, 1, 1.5, 2, 2.5, 3, 3.5, 4 and 5 kg/ha, I+XXIV+III: 1+0.5+0.5, 1.5+0.75+0.75, 2+1+1, 2+0.5+1.5, 1.86+0.375+0.75, 2.5+0.5+1, 3+0.725+1.25, 3+0.5+1.5, 2+0.67+1.33, 2.5+0.834+1.66 and 2+1+2 kg/ha, I+XXIV+IV: 2+1+1, 2+1.5+0.5, 2+0.5+1.5, 1+0.5+0.5, 1+0.75+0.25, and 1+0.25+0.75 kg/ha.

After 4 to 5 weeks it was ascertained that the compositions had a better herbicidal action than their components, combined with superior crop plant compabitility. The results are given below:

| Active ingredient | I | | | | | | | | |
|---|---|---|---|---|---|---|---|---|---|
| kg/ha | 0.5 | 1 | 1.5 | 1.86 | 2 | 2.5 | 3 | 4 | 5 |
| Crop plants: | | | | | | | | | |
| *Beta vulgaris* | 0 | 0 | 0 | 0 | 0 | 0 | 0 | 10 | 15 |
| Unwanted plants: | | | | | | | | | |
| *Avena fatua* | 5 | 12 | 15 | 18 | 20 | 25 | 40 | 75 | 90 |
| *Echinochloa crus-galli* | 6 | 13 | 20 | 27 | 32 | 50 | 65 | 75 | 90 |
| *Stellaria media* | 20 | 45 | 60 | 70 | 80 | 90 | 95 | 100 | 100 |
| *Galium aparine* | 15 | 40 | 50 | 68 | 75 | 80 | 85 | 90 | 95 |
| *Chenopodium album* | 25 | 40 | 60 | 73 | 80 | 90 | 95 | 100 | 100 |
| *Alopecurus myosuroides* | 6 | 11 | 19 | 20 | 22 | 25 | 30 | 45 | 60 |
| *Lamium amplexicaule* | 10 | 20 | 25 | 33 | 40 | 60 | 70 | 90 | 100 |

| Active ingredient | III | | | | | | | | | | |
|---|---|---|---|---|---|---|---|---|---|---|---|
| kg/ha | 0.5 | 0.75 | 1 | 1.25 | 1.33 | 1.5 | 1.66 | 2 | 3 | 4 | 5 |
| *Beta vulgaris* | 0 | 0 | 0 | 0 | 0 | 0 | 0 | 0 | 0 | 10 | 20 |
| *Avena fatua* | 15 | 30 | 40 | 43 | 45 | 45 | 47 | 54 | 75 | 80 | 90 |
| *Echinochloa crus-galli* | 25 | 45 | 70 | 80 | 86 | 90 | 93 | 100 | 100 | 100 | 100 |
| *Stellaria media* | 10 | 20 | 25 | 30 | 38 | 45 | 48 | 55 | 65 | 70 | 85 |
| *Galium aparine* | 10 | 12 | 15 | 18 | 22 | 25 | 26 | 30 | 40 | 43 | 45 |
| *Chenopodium album* | 15 | 17 | 20 | 25 | 30 | 35 | 38 | 45 | 50 | 57 | 65 |
| *Alopecurus myosuroides* | 20 | 40 | 50 | 60 | 75 | 90 | 94 | 100 | 100 | 100 | 100 |
| *Lamium amplexicaule* | 10 | 15 | 20 | 25 | 27 | 35 | 40 | 55 | 60 | 70 | 75 |

| Active ingredient | IV | | | | | | |
|---|---|---|---|---|---|---|---|
| kg/ha | 0.25 | 0.5 | 0.75 | 1 | 1.5 | 2 | 4 |
| *Beta vulgaris* | 0 | 0 | 0 | 0 | 0 | 10 | 25 |
| *Avena fatua* | 10 | 20 | 30 | 50 | 83 | 95 | 100 |
| *Echinochloa crus-galli* | 0 | 10 | 15 | 20 | 40 | 50 | 90 |
| *Stellaria media* | 6 | 7 | 10 | 13 | 15 | 18 | 25 |
| *Galium aparine* | 0 | 0 | 0 | 0 | 5 | 8 | 15 |
| *Chenopodium album* | 0 | 5 | 7 | 10 | 15 | 20 | 33 |
| *Alopecurus myosuroides* | 11 | 26 | 35 | 58 | 85 | 95 | 100 |
| *Lamium amplexicaule* | 0 | 5 | 9 | 12 | 15 | 20 | 25 |

| Active ingredient | XXIV | | | | | | | | | | |
|---|---|---|---|---|---|---|---|---|---|---|---|
| kg/ha | 0.25 | 0.375 | 0.5 | 0.67 | 0.725 | 0.75 | 0.834 | 1 | 1.5 | 2 | 2.5 |
| *Beta vulgaris* | 0 | 0 | 0 | 0 | 0 | 0 | 0 | 0 | 0 | 0 | 0 |
| *Avena fatua* | 15 | 20 | 25 | 27 | 30 | 35 | 45 | 60 | 75 | 80 | 85 |
| *Echinochloa crus-galli* | 20 | 31 | 35 | 39 | 42 | 45 | 55 | 60 | 90 | 100 | 100 |
| *Stellaria media* | 20 | 23 | 25 | 27 | 28 | 30 | 40 | 50 | 75 | 85 | 90 |
| *Galium aparine* | 15 | 18 | 25 | 25 | 28 | 30 | 33 | 40 | 50 | 65 | 70 |
| *Chenopodium album* | 15 | 20 | 30 | 31 | 33 | 35 | 37 | 40 | 45 | 60 | 65 |
| *Alopecurus myosuroides* | 25 | 30 | 40 | 45 | 49 | 60 | 65 | 75 | 90 | 95 | 100 |
| *Lamium amplexicaule* | 20 | 23 | 25 | 27 | 30 | 30 | 40 | 50 | 70 | 80 | 90 |

| Active ingredient | XXIV | | | |
|---|---|---|---|---|
| kg/ha | 3 | 3.5 | 4 | 5 |
| *Beta vulgaris* | 5 | 7 | 10 | 18 |
| *Avena fatua* | 90 | 96 | 100 | 100 |
| *Echinochloa crus-galli* | 100 | 100 | 100 | 100 |
| *Stellaria media* | 95 | 100 | 100 | 100 |
| *Galium aparine* | 75 | 80 | 85 | 95 |
| *Chenopodium album* | 70 | 80 | 90 | 100 |
| *Alopecurus myosuroides* | 100 | 100 | 100 | 100 |
| *Lamium amplexicaule* | 95 | 100 | 100 | 100 |

| | I + XXIV + III | | | | | | | |
|---|---|---|---|---|---|---|---|---|
| Active ingredient kg/ha | 1+ 0.5+ 0.5 | 1.5+ 0.75+ 0.75 | 2+ 1+ 1 | 2+ 0.5+ 1.5 | 1.86+ 0.375 +0.75 | 2.5+ 0.5+ 1 | 3+ 0.725+ 1.25 | 3+ 0.5+ 1.5 |
| *Beta vulgaris* | 0 | 0 | 0 | 0 | 0 | 0 | 0 | 0 |
| *Avena fatua* | 92 | 100 | 100 | 100 | 100 | 100 | 100 | 100 |
| *Echinochloa crus-galli* | 100 | 100 | 100 | 100 | 100 | 100 | 100 | 100 |
| *Stellaria media* | 100 | 100 | 100 | 100 | 100 | 100 | 100 | 100 |
| *Galium aparine* | 100 | 100 | 100 | 100 | 100 | 100 | 100 | 100 |
| *Chenopodium album* | 100 | 100 | 100 | 100 | 100 | 100 | 100 | 100 |
| *Alopecurus myosuroides* | 100 | 100 | 100 | 100 | 100 | 100 | 100 | 100 |
| *Lamium amplexicaule* | 95 | 100 | 100 | 100 | 100 | 100 | 100 | 100 |

| | I + XXIV + III | | | I + XXIV + IV | | | | | |
|---|---|---|---|---|---|---|---|---|---|
| | 2+ 0.67+ 1.33 | 2.5+ 0.834+ 1.66 | 2+1+2 | 2+1+1 | 2+ 1.5+ 0.5 | 2+ 0.5+ 1.5 | 1+ 0.5+ 0.5 | 1+ 0.75+ 0.25 | 1+ 0.25+ 0.75 |
| *Beta vulgaris* | 0 | 0 | 0 | 0 | 0 | 0 | 0 | 0 | 0 |
| *Avena fatua* | 100 | 100 | 100 | 100 | 100 | 100 | 97 | 100 | 100 |
| *Echinochloa crus-galli* | 100 | 100 | 100 | 100 | 100 | 100 | 100 | 100 | 100 |
| *Stellaria media* | 100 | 100 | 100 | 100 | 100 | 100 | 100 | 100 | 100 |
| *Galium aparine* | 100 | 100 | 100 | 100 | 100 | 100 | 100 | 100 | 95 |
| *Chenopodium album* | 100 | 100 | 100 | 100 | 100 | 100 | 100 | 100 | 90 |
| *Alopecurus myosuroides* | 100 | 100 | 100 | 100 | 100 | 100 | 100 | 100 | 100 |

-continued

| | | | | | | | | | |
|---|---|---|---|---|---|---|---|---|---|
| *Lamium amplexicaule* | 100 | 100 | 100 | 100 | 100 | 100 | 95 | 90 | 75 |

EXAMPLE 20

In the greenhouse, loamy sandy soil was filled into pots and sown with various seeds. The soil prepared in this manner was then treated with the following amounts of the following individual active ingredients and compositions thereof as dispersions or emulsions:

I: 1-phenyl-4-amino-5-chloropyridazone-(6)
0.5, 1, 1.5, 2, 2.5, 3, 4, 5 and 6 kg/ha, III: O-(methylaminosulfonyl)-glycolic acid-N-isopropylanilide
0.25, 0.5, 0.75, 1, 1.5, 2, 2.5, 3, 4, 5 and 6 kg/ha, IV: 2,3-dichloroallyl N,N-diisopropylthiolcarbamate
0.25, 0.5, 0.75, 1, 1.5, 2 and 4 kg/ha, XXXXVI: 2,3-dihydro-3,3-dimethyl-2-ethoxybenzofuran-5-yl-N-methyl-N-acetylaminosulfonate
0.25, 0.5, 0.75, 1, 1.5, 2, 3, 4 and 6 kg/ha, I+III+IV: 2+1+1, 2+1.5+0.5, 2+0.5+1.5, 1+0.5+0.5, 1+0.75+0.25, and 1+0.25+0.75 kg/ha, I+III+XXXXVI: 1.5+0.75+0.75, 2+1+1, 0.5+0.25+0.25, 1+0.5+0.5, 2+1.5+0.5, 2+0.5+1.5, 3+1.5+1.5, 3+1+2 and 3+2+1 kg/ha.

After 4 to 5 weeks it was ascertained that the compositions had a better herbicidal action than their components, combined with superior crop plant compatibility.

The results are given below:

| Active ingredient | I | | | | | | | | | |
|---|---|---|---|---|---|---|---|---|---|---|
| kg/ha | 0.5 | 1 | 1.5 | 2 | 2.5 | 3 | 4 | 5 | 6 | |
| Crop plants: | | | | | | | | | | |
| *Beta vulgaris* | 0 | 0 | 0 | 0 | 0 | 0 | 10 | 15 | 20 | |
| Unwanted plants: | | | | | | | | | | |
| *Avena fatua* | 5 | 12 | 15 | 20 | 25 | 40 | 75 | 90 | 100 | |
| *Echinochloa crus-galli* | 6 | 13 | 20 | 32 | 50 | 65 | 75 | 90 | 100 | |
| *Stellaria media* | 20 | 45 | 60 | 80 | 90 | 95 | 100 | 100 | 100 | |
| *Galium aparine* | 15 | 40 | 50 | 75 | 80 | 85 | 90 | 95 | 100 | |
| *Chenopodium album* | 25 | 40 | 60 | 80 | 90 | 95 | 100 | 100 | 100 | |
| *Alopecurus myosuroides* | 6 | 11 | 19 | 22 | 25 | 30 | 45 | 0.25 | 0.5 | |
| *0.75* | am-plexicaule | 10 | 1.5 | 25 | 40 | 60 | 70 | 90 | 100 | 100 |

| Active ingredient | III | | | | | | | | | | |
|---|---|---|---|---|---|---|---|---|---|---|---|
| kg/ha | 0.25 | 0.5 | 0.75 | 1 | 1.5 | 2 | 2.5 | 3 | 4 | 5 | 6 |
| *Beta vulgaris* | 0 | 0 | 0 | 0 | 0 | 0 | 0 | 0 | 10 | 20 | 30 |
| *Avena fatua* | 10 | 15 | 30 | 40 | 45 | 54 | 70 | 75 | 80 | 90 | 85 |
| *Echinochloa crus-galli* | 20 | 25 | 45 | 70 | 90 | 100 | 100 | 100 | 100 | 100 | 100 |
| *Stellaria media* | 5 | 10 | 20 | 25 | 45 | 55 | 60 | 65 | 70 | 85 | 100 |
| *Galium aparine* | 5 | 10 | 12 | 15 | 25 | 30 | 35 | 40 | 43 | 45 | 60 |
| *Chenopodium album* | 10 | 15 | 17 | 20 | 35 | 45 | 60 | 50 | 57 | 65 | 75 |
| *Alopecurus myosuroides* | 10 | 20 | 40 | 50 | 90 | 100 | 100 | 100 | 100 | 100 | 100 |
| *Lamium amplexicaule* | 7 | 10 | 15 | 20 | 35 | 55 | 70 | 60 | 70 | 75 | 90 |

| Active ingredient | IV | | | | | | |
|---|---|---|---|---|---|---|---|
| kg/ha | 0,25 | 0,5 | 0,75 | 1 | 1,5 | 2 | 4 |
| *Beta vulgaris* | 0 | 0 | 0 | 0 | 0 | 10 | 25 |
| *Avena fatua* | 10 | 20 | 30 | 50 | 85 | 95 | 100 |
| *Echinochloa crus-galli* | 0 | 10 | 15 | 20 | 40 | 50 | 90 |
| *Stellaria media* | 6 | 7 | 10 | 13 | 15 | 18 | 25 |
| *Galium aparine* | 0 | 0 | 0 | 0 | 5 | 8 | 15 |
| *Chenopodium album* | 0 | 5 | 7 | 10 | 15 | 20 | 35 |
| *Alopecurus myosuroides* | 11 | 26 | 35 | 58 | 85 | 95 | 100 |
| *Lamium amplexicaule* | 0 | 5 | 9 | 12 | 15 | 20 | 25 |

| Active ingredient | VIII | | | | | | | |
|---|---|---|---|---|---|---|---|---|
| kg/ha | 0.25 | 0.5 | 0.75 | 1 | 1.5 | 2 | 3 | 4 |
| *Beta vulgaris* | 0 | 0 | 0 | 0 | 0 | 0 | 5 | 10 |
| *Avena fatua* | 30 | 45 | 65 | 80 | 100 | 100 | 100 | 100 |
| *Echinochloa crus-galli* | 50 | 70 | 80 | 90 | 100 | 100 | 100 | 100 |
| *Stellaria media* | 50 | 60 | 65 | 75 | 95 | 100 | 100 | 100 |
| *Galium aparine* | 10 | 20 | 30 | 40 | 52 | 70 | 80 | 95 |
| *Chenopodium album* | 20 | 30 | 37 | 45 | 65 | 75 | 85 | 95 |
| *Alopecurus myosuroides* | 35 | 50 | 65 | 75 | 96 | 100 | 100 | 100 |
| *Lamium amplexicaule* | 15 | 25 | 50 | 70 | 80 | 90 | 100 | 100 |

| | I + III + IV | | | | | |
|---|---|---|---|---|---|---|
| Active ingredient kg/ha | 2+1 +1 | 2+ 1.5+ 0.5 | 2+ 0.5+ 1.5 | 1+ 0.5+ 0.5 | 1+ 0.75+ 0.25 | 1+ 0.25+ 0.75 |
| Crop plants: | | | | | | |
| *Beta vulgaris* | 0 | 0 | 0 | 0 | 0 | 0 |
| Unwanted plants: | | | | | | |
| *Avena fatua* | 100 | 100 | 100 | 90 | 85 | 95 |
| *Echinochloa crus-galli* | 100 | 100 | 100 | 90 | 100 | 90 |
| *Stellaria media* | 100 | 100 | 100 | 100 | 100 | 100 |
| *Galium aparine* | 100 | 100 | 100 | 90 | 95 | 85 |
| *Chenopodium album* | 100 | 100 | 100 | 85 | 85 | 83 |
| *Alopecurus myosuroides* | 100 | 100 | 100 | 100 | 100 | 100 |
| *Lamium amplexicaule* | 100 | 100 | 100 | 75 | 75 | 78 |

| | I + III + XXXVI | | | | | | |
|---|---|---|---|---|---|---|---|
| Active ingredient | 1.5+ 0.75+ | | 0.5+ 0.25+ | 1+ 0.5+ | 2+ 1.5+ | 2+ 0.5+ | 3+ 1.5+ |

-continued

| kg/ha | 0.75 | 2+1+1 | 0.25 | 0.5 | 0.5 | 1.5 | 1.5 | 3+1+2 | 3+2+1 |
|---|---|---|---|---|---|---|---|---|---|
| *Beta vulgaris* | 0 | 0 | 0 | 0 | 0 | 0 | 0 | 0 | 0 |
| *Avena fatua* | 100 | 100 | 75 | 97 | 100 | 100 | 100 | 100 | 100 |
| *Echinochloa crus-galli* | 100 | 100 | 86 | 100 | 100 | 100 | 100 | 100 | 100 |
| *Stellaria media* | 100 | 100 | 80 | 100 | 100 | 100 | 100 | 100 | 100 |
| *Galium aparine* | 100 | 100 | 75 | 100 | 100 | 100 | 100 | 100 | 100 |
| *Chenopodium album* | 100 | 100 | 65 | 90 | 100 | 100 | 100 | 100 | 100 |
| *Alopecurus myosuroides* | 100 | 100 | 75 | 100 | 100 | 100 | 100 | 100 | 100 |
| *Lamium amplexicaule* | 100 | 100 | 75 | 100 | 100 | 100 | 100 | 100 | 100 |

0 = no damage
100 = complete destruction

EXAMPLE 21

In the greenhouse, various plants were treated at a growth height of from 3 to 15 cm with the following amounts of the following individual active ingredients and compositions thereof as emulsions or dispersions:

II: O-(isopropylaminosulfonyl)-glycolic acid-N-butyn-1-yl-3-anilide
1.5, 2, 2.5, 3, 3.5 and 4 kg/ha, III: O-(methylaminosulfonyl)-glycolic acid-N-isopropylanilide
1.5, 2 and 3 kg/ha, XXIV: O-(methylaminosulfonyl)-glycolic acid hexamethylene amide
0.5, 1, 1.5, 2, 3 and 4 kg/ha, XXV: O-(ethylaminosulfonyl)-glycolic acid hexamethylene amide
0.5, 1, 1.5, 2 and 4 kg/ha, XXXX: S-(p-chlorobenzyl)-(2,2,4-trimethylazatidine)-1-carbothioate,
0.5, 1 and 2 kg/ha, LIV: N-methylacetanilido-α-isopropylsulfite,
0.5, 1 and 2 kg/ha, LX 1,2-dimethyl-3,5-diphenyl-4-bromopyrazolium methylsulfate
0.5 and 2 kg/ha, LXII: 1,2-dimethyl-3,5-diphenyl-4-methylpyrazolium methylsulfate
0.5 and 2 kg/ha, LXIII: 1,2-dimethyl-3,5-diphenyl-4-methoxypyrazolium methylsulfate
0.5 and 2 kg/ha, II+XXIV: 3.5+0.5, 3+1, 2.5+1.5 and 2+2 kg/ha,
II+XXV: 3.5+0.5, 3+1, 2.5+1.5 and 2+2 kg/ha,
II+LX: 1.5+0.5 kg/ha,
II+LXII: 1.5+0.5 kg/ha,
II+LXIII: 1.5+0.5 kg/ha,
XXXX+IIV: 0.5+0.5 and 1+1 kg/ha,
XXIV+III: 0.5+1.5 and 1+2 kg/ha.

After 2 to 3 weeks it was ascertained that the compositions had a better herbicidal action than their components, combined with superior crop plant compatibility.

The results are given below:

| Active ingredient | II | | | | | | III | | |
|---|---|---|---|---|---|---|---|---|---|
| kg/ha | 1.5 | 2 | 2.5 | 3 | 3.5 | 4 | 1.5 | 2 | 3 |
| Crop plants: | | | | | | | | | |
| *Beta vulgaris* | 0 | 0 | 0 | 0 | 5 | 10 | 0 | 0 | 0 |
| Unwanted plants: | | | | | | | | | |
| *Avena fatua* | 55 | 60 | 63 | 65 | 68 | 70 | 60 | 65 | 70 |
| *Echinochloa crus-galli* | 78 | 80 | 90 | 95 | 100 | 100 | 75 | 80 | 90 |
| *Stellaria media* | 25 | 30 | 34 | 35 | 37 | 40 | 25 | 30 | 40 |
| *Galium aparine* | 24 | 28 | 35 | 40 | 44 | 46 | 20 | 25 | 41 |
| *Chenopodium album* | 50 | 55 | 58 | 60 | 65 | 70 | 35 | 40 | 45 |
| *Alopecurus myosuroides* | 95 | 100 | 100 | 100 | 100 | 100 | 100 | 100 | 100 |
| *Lamium amplexicaule* | 30 | 40 | 48 | 50 | 55 | 60 | 20 | 25 | 35 |

| Active ingredient | XXIV | | | | | | XXV | | | | |
|---|---|---|---|---|---|---|---|---|---|---|---|
| kg/ha | 0.5 | 1 | 1.5 | 2 | 3 | 4 | 0.5 | 1 | 1.5 | 2 | 4 |
| *Beta vulgaris* | 0 | 0 | 0 | 5 | 10 | 15 | 0 | 0 | 0 | 5 | 20 |
| *Avena fatua* | 30 | 45 | 60 | 70 | 80 | 95 | 25 | 40 | 60 | 75 | 90 |
| *Echinochloa crus-galli* | 40 | 70 | 80 | 90 | 98 | 100 | 40 | 60 | 80 | 90 | 100 |
| *Stellaria media* | 20 | 40 | 45 | 60 | 70 | 85 | 15 | 20 | 35 | 50 | 80 |
| *Galium aparine* | 20 | 35 | 40 | 50 | 65 | 75 | 10 | 20 | 25 | 35 | 65 |
| *Chenopodium album* | 15 | 25 | 35 | 45 | 60 | 80 | 10 | 20 | 30 | 45 | 85 |
| *Alopecurus myosuroides* | 50 | 75 | 90 | 95 | 100 | 100 | 45 | 60 | 80 | 90 | 100 |
| *Lamium amplexicaule* | 5 | 20 | 35 | 45 | 55 | 60 | 3 | 7 | 10 | 20 | 40 |

| Active ingredient | XXXX | | | LIV | | | LX | | LXII | | LXIII | |
|---|---|---|---|---|---|---|---|---|---|---|---|---|
| kg/ha | 0.5 | 1 | 2 | 0.5 | 1 | 2 | 0.5 | 2 | 0.5 | 2 | 0.5 | 2 |
| *Beta vulgaris* | 0 | 0 | 7 | 0 | 0 | 0 | 0 | 20 | 0 | 20 | 0 | 18 |
| *Avena fatua* | 40 | 75 | 95 | 10 | 35 | 50 | 50 | 100 | 50 | 100 | 40 | 90 |
| *Echinochloa crus-galli* | 35 | 75 | 90 | 20 | 50 | 80 | 0 | 15 | 3 | 15 | 0 | 10 |
| *Stellaria media* | 0 | 0 | 0 | 10 | 25 | 30 | 25 | 85 | 15 | 80 | 10 | 60 |
| *Galium aparine* | 0 | 5 | 10 | 0 | 0 | 20 | 5 | 20 | 0 | 15 | 5 | 20 |
| *Chenopodium album* | 0 | 7 | 10 | 0 | 5 | 30 | 20 | 60 | 15 | 40 | 10 | 65 |
| *Alopecurus myosuroides* | 35 | 70 | 95 | 20 | 50 | 85 | 5 | 30 | 10 | 35 | 10 | 30 |
| *Lamium amplexicaule* | 0 | 10 | 15 | 0 | 15 | 25 | 20 | 60 | 20 | 60 | 15 | 60 |

| Active ingredient | II + XXIV | | | | II + XXV | | II + XXV | |
|---|---|---|---|---|---|---|---|---|
| kg/ha | 3.5+ 0.5 | 3+1 | 2.5+ 1.5 | 2+2 | 3.5+ 0.5 | 3+1 | 2.5+ 1.5 | 2+2 |
| *Beta vulgaris* | 5 | 0 | 0 | 5 | 5 | 0 | 0 | 5 |
| *Avena fatua* | 100 | 100 | 100 | 100 | 100 | 100 | 100 | 100 |
| *Echinochloa crus-galli* | 100 | 100 | 100 | 100 | 100 | 100 | 100 | 100 |
| *Stellaria media* | 98 | 95 | 100 | 100 | 92 | 95 | 100 | 100 |
| *Galium aparine* | 100 | 100 | 100 | 100 | 94 | 100 | 100 | 100 |
| *Chenopodium album* | 100 | 100 | 100 | 100 | 100 | 100 | 100 | 100 |

-continued

| | | | | | | | | |
|---|---|---|---|---|---|---|---|---|
| *Alopecurus myosuroides* | 100 | 100 | 100 | 100 | 100 | 100 | 100 | 100 |
| *Lamium amplexicaule* | 100 | 95 | 100 | 100 | 100 | 97 | 100 | 100 |

| Active ingredient | II + LX | II + LXII | II + LXIII | XXXX + LIV | | XXIV + III | |
|---|---|---|---|---|---|---|---|
| kg/ha | 1.5+0.5 | 1.5+0.5 | 1.5+0.5 | 0.5+0.5 | 1+1 | 0.5+1.5 | 1+2 |
| *Beta vulgaris* | 0 | 0 | 0 | 0 | 0 | 0 | 0 |
| *Avena fatua* | 100 | 100 | 100 | 90 | 100 | 100 | 100 |
| *Echinochloa crus-galli* | 100 | 100 | 100 | 75 | 100 | 100 | 100 |
| *Stellaria media* | 90 | 80 | 80 | 50 | 65 | 85 | 100 |
| *Galium aparine* | 70 | 65 | 67 | 40 | 50 | 80 | 100 |
| *Chenopodium album* | 100 | 100 | 90 | 45 | 55 | 90 | 100 |
| *Alopecurus myosuroides* | 100 | 100 | 100 | 95 | 100 | 100 | 100 |
| *Lamium amplexicaule* | 90 | 90 | 70 | 48 | 65 | 65 | 100 |

0 = no damage
100 = complete destruction

EXAMPLE 22

In the greenhouse, various plants were treated at a growth height of from 2 to 17 cm with the following amounts of the following individual active ingredients and compositions thereof as emulsions or dispersions:

II: O-(isopropylaminosulfonyl)-glycolic acid-N-butyn-1-yl-3-anilide
1.5, 2, 2.25, 2.5, 3 and 4 kg/ha, III: O-(methylaminosulfonyl)-glycolic acid-N-isopropylanilide
1, 2, 2.5 and 3 kg/ha, XIII: 3-(N-m-trifluoromethylphenylcarbamoyloxy)-(p-methylphenyl)-methylcarbamate,
0.5, 0.75, 1, 1.5, 2, 2.5, 3 and 4 kg/ha, LIV: N-methylacetanilido-α-isopropylsulfite
1 and 2 kg/ha, LXIV: O-(dimethylaminosulfonyl)-glycolic acid-N-methylanilide
1 and 2 kg/ha, LXV: O-(dimethylaminosulfonyl)-glycolic acid-N-ethylanilide
1 and 2 kg/ha, XIII+II: 0.5+1.5, 0.5+2.5, 0.75+2.25, 1+1.5, 1+2 and 1.5+2.5 kg/ha, XIII+III: 0.5+2, 1+1 and 1+2 kg/ha, XIII+LIV: 1+1 kg/ha, XIII+LXIV: 1+1 kg/ha, XIII+LXV: 1+1 kg/ha.

After 2 to 3 weeks it was ascertained that the compositions had a better herbicidal action than their components, combined with superior crop plant compatibility. The results are given below:

| Active ingredient | II | | | | | | III | | | |
|---|---|---|---|---|---|---|---|---|---|---|
| kg/ha | 1.5 | 2 | 2.25 | 2.5 | 3 | 4 | 1 | 2 | 2.5 | 3 |
| Crop plants: | | | | | | | | | | |
| *Beta vulgaris* | 0 | 0 | 0 | 0 | 0 | 10 | 0 | 0 | 0 | 0 |
| Unwanted plants: | | | | | | | | | | |
| *Avena fatua* | 55 | 60 | 60 | 63 | 65 | 70 | 50 | 65 | 68 | 70 |
| *Echinochloa crus-galli* | 78 | 80 | 85 | 90 | 95 | 100 | 70 | 80 | 85 | 90 |
| *Stellaria media* | 25 | 30 | 33 | 34 | 35 | 40 | 15 | 30 | 35 | 40 |
| *Galium aparine* | 24 | 28 | 30 | 35 | 40 | 46 | 15 | 25 | 35 | 41 |
| *Chenopodium album* | 50 | 55 | 56 | 58 | 60 | 70 | 30 | 40 | 43 | 45 |
| *Alopecurus myosuroides* | 95 | 100 | 100 | 100 | 100 | 100 | 90 | 100 | 100 | 100 |
| *Lamium amplexicaule* | 30 | 40 | 45 | 48 | 50 | 60 | 15 | 25 | 30 | 35 |

| Active ingredient | XIII | | | | | | | | LIV | | LXIV | | LX | |
|---|---|---|---|---|---|---|---|---|---|---|---|---|---|---|
| kg/ha | 0.5 | 0.75 | 1 | 1.5 | 2 | 2.5 | 3 | 4 | 1 | 2 | 1 | 2 | 1 | 2 |
| *Beta vulgaris* | 0 | 0 | 0 | 0 | 0 | 15 | 20 | 25 | 0 | 0 | 0 | 0 | 0 | 0 |
| *Avena fatua* | 10 | 12 | 15 | 30 | 40 | 45 | 50 | 60 | 35 | 50 | 40 | 60 | 45 | 70 |
| *Echinochloa crus-galli* | 16 | 25 | 35 | 65 | 80 | 85 | 90 | 98 | 50 | 80 | 65 | 80 | 60 | 95 |
| *Stellaria media* | 70 | 86 | 95 | 100 | 100 | 100 | 100 | 100 | 25 | 30 | 10 | 20 | 20 | 30 |
| *Galium aparine* | 28 | 40 | 55 | 60 | 70 | 80 | 90 | 100 | 0 | 20 | 15 | 30 | 10 | 30 |
| *Chenopodium album* | 60 | 85 | 100 | 100 | 100 | 100 | 100 | 100 | 5 | 30 | 25 | 50 | 25 | 45 |
| *Alopecurus myosuroides* | 5 | 20 | 50 | 55 | 60 | 65 | 70 | 80 | 50 | 85 | 80 | 100 | 85 | 100 |
| *Lamium amplexicaule* | 60 | 80 | 90 | 95 | 100 | 100 | 100 | 100 | 15 | 25 | 20 | 40 | 25 | 35 |

| | XIII + II | | | | | | XIII + III | | |
|---|---|---|---|---|---|---|---|---|---|
| Active ingredient kg/ha | 0.5+ 1.5 | 0.5+ 2.5 | 0.75+ 2.25 | 1+1.5 | 1+2 | 1.5+ 2.5 | 0.5+2 | 1+1 | 1+2 |
| *Beta vulgaris* | 0 | 0 | 0 | 0 | 0 | 5 | 0 | 0 | 0 |
| *Avena fatua* | 100 | 100 | 100 | 100 | 100 | 100 | 100 | 100 | 100 |
| *Echinochloa crus-galli* | 100 | 100 | 100 | 100 | 100 | 100 | 100 | 100 | 100 |
| *Stellaria media* | 100 | 100 | 100 | 100 | 100 | 100 | 100 | 100 | 100 |
| *Galium aparine* | 100 | 100 | 100 | 100 | 100 | 100 | 93 | 100 | 100 |
| *Chenopodium album* | 100 | 100 | 100 | 100 | 100 | 100 | 100 | 100 | 100 |
| *Alopecurus myosuroides* | 100 | 100 | 100 | 100 | 100 | 100 | 100 | 100 | 100 |
| *Lamium amplexicaule* | 100 | 100 | 100 | 100 | 100 | 100 | 100 | 100 | 100 |

| Active ingredient | XIII + LIV | XIII + LXIV | XIII + LXV |
|---|---|---|---|
| kg/ha | 1+1 | 1+1 | 1+1 |
| *Beta vulgaris* | 0 | 0 | 0 |
| *Avena fatua* | 100 | 95 | 100 |
| *Echinochloa crus-galli* | 100 | 100 | 100 |
| *Stellaria media* | 100 | 100 | 100 |
| *Galium aparine* | 95 | 100 | 100 |
| *Chenopodium album* | 100 | 100 | 100 |
| *Alopecurus myosuroides* | 100 | 100 | 100 |

-continued

| | | | |
|---|---|---|---|
| *Lamium amplexicaule* | 100 | 100 | 100 |

0 = no damage
100 = complete destruction

EXAMPLE 23

In the greenhouse, loamy sandy soil was filled into pots and sown with various seeds. The soil prepared in this manner was then treated with the following amounts of the following individual active ingredients and compositions thereof as emulsions or dispersions:

I: 1-phenyl-4-amino-5-chloropyridazone-(6)
0.5, 1, 1.5, 2, 2.5, 3 and 4 kg/ha,

XXIV: O-(methylaminosulfonyl)-glycolic acid hexamethylene amide,
0.25, 0.375, 0.75, 1, 1.5, 2, 3 and 4 kg/ha, XXXXVI: 2,3-dihydro-3,3-dimethyl-2-ethoxybenzofuran-5-yl-N-methyl-N-acetylaminosulfonate
0.25, 0.5, 0.75, 1, 1.25, 1.5, 2, 3 and 4 kg/ha, I+XXIV+XXXXVI: 2+1+1, 2+0.5+1.5, 2.5+0.5+1, 1+0.25+0.75, 1.5+0.375+1.125, 1.5+0.75+0.75, 0.5+0.25+0.25 and 1+0.5+0.5 kg/ha.

After 4 to 5 weeks it was ascertained that the compositions had a better herbicidal action than its components, combined with superior crop plant compatibility.

The results are given below:

| Active ingredient | I | | | | | | |
|---|---|---|---|---|---|---|---|
| kg/ha | 0.5 | 1 | 1.5 | 2 | 2.5 | 3 | 4 |
| Crop plants: | | | | | | | |
| *Beta vulgaris* | 0 | 0 | 0 | 0 | 0 | 0 | 10 |
| Unwanted plants: | | | | | | | |
| *Avena fatua* | 5 | 12 | 15 | 20 | 25 | 40 | 75 |
| *Echinochloa crus-galli* | 6 | 13 | 20 | 32 | 50 | 65 | 75 |
| *Stellaria media* | 20 | 24 | 60 | 80 | 90 | 95 | 100 |
| *Galium aparine* | 15 | 40 | 50 | 75 | 80 | 85 | 90 |
| *Chenopodium album* | 25 | 40 | 60 | 80 | 90 | 95 | 100 |
| *Alopecurus myosuroides* | 6 | 11 | 19 | 22 | 25 | 30 | 45 |
| *Lamium amplexicaule* | 10 | 20 | 25 | 40 | 60 | 70 | 90 |

| Active ingredient | XXIV | | | | | | | | |
|---|---|---|---|---|---|---|---|---|---|
| kg/ha | 0.25 | 0.375 | 0.5 | 0.75 | 1 | 1.5 | 2 | 3 | 4 |
| *Beta vulgaris* | 0 | 0 | 0 | 0 | 0 | 0 | 0 | 0 | 0 |
| *Avena fatua* | 15 | 20 | 25 | 35 | 60 | 75 | 80 | 90 | 100 |
| *Echinochloa crus-galli* | 20 | 31 | 35 | 45 | 60 | 90 | 100 | 100 | 100 |
| *Stellaria media* | 20 | 23 | 25 | 30 | 50 | 75 | 85 | 95 | 100 |
| *Galium aparine* | 15 | 18 | 25 | 30 | 40 | 50 | 65 | 75 | 85 |
| *Chenopodium album* | 15 | 20 | 30 | 35 | 40 | 45 | 60 | 70 | 90 |
| *Alopecurus myosuroides* | 25 | 30 | 40 | 60 | 75 | 90 | 95 | 100 | 100 |
| *Lamium amplexicaule* | 20 | 23 | 25 | 30 | 50 | 70 | 80 | 95 | 100 |

| Active ingredient | XXIV | | | | | | | | |
|---|---|---|---|---|---|---|---|---|---|
| kg/ha | 0.25 | 0.375 | 0.5 | 0.75 | 1 | 1.5 | 2 | 3 | 4 |
| *Beta vulgaris* | 0 | 0 | 0 | 0 | 0 | 0 | 0 | 5 | 10 |
| *Avena fatua* | 15 | 20 | 25 | 35 | 60 | 75 | 80 | 90 | 100 |
| *Echinochloa crus-galli* | 20 | 31 | 35 | 45 | 60 | 90 | 100 | 100 | 100 |
| *Stellaria media* | 20 | 23 | 25 | 30 | 50 | 75 | 85 | 95 | 100 |
| *Galium aparine* | 15 | 18 | 25 | 30 | 40 | 50 | 65 | 75 | 85 |
| *Chenopodium album* | 15 | 20 | 30 | 35 | 40 | 45 | 60 | 70 | 90 |
| *Alopecurus myosuroides* | 25 | 30 | 40 | 60 | 75 | 90 | 95 | 100 | 100 |
| *Lamium amplexicaule* | 20 | 23 | 25 | 30 | 50 | 70 | 80 | 95 | 100 |

| Active ingredient | XXXXVI | | | | | | | | |
|---|---|---|---|---|---|---|---|---|---|
| kg/ha | 0.25 | 0.5 | 0.75 | 1 | 1.125 | 1.5 | 2 | 3 | 4 |
| *Beta vulgaris* | 0 | 0 | 0 | 0 | 0 | 0 | 0 | 10 | 20 |
| *Avena fatua* | 20 | 30 | 45 | 60 | 70 | 80 | 100 | 100 | 100 |
| *Echinochloa crus-galli* | 20 | 40 | 60 | 70 | 80 | 90 | 100 | 100 | 100 |
| *Stellaria media* | 15 | 20 | 35 | 55 | 70 | 85 | 95 | 100 | 100 |
| *Galium aparine* | 15 | 20 | 25 | 40 | 55 | 70 | 80 | 95 | 100 |
| *Chenopodium album* | 5 | 10 | 15 | 25 | 40 | 60 | 70 | 85 | 95 |
| *Alopecurus myosuroides* | 20 | 35 | 50 | 65 | 68 | 95 | 100 | 100 | 100 |
| *Lamium amplexicaule* | 18 | 23 | 35 | 50 | 60 | 75 | 85 | 95 | 100 |

| | I + XXIV + XXXXVI | | | | | | | |
|---|---|---|---|---|---|---|---|---|
| Active ingredient kg/ha | 2+1+1 | 2+ 0.5+ 1.5 | 2.5+ 0.5+ 1 | 1+ 0.25+ 0.75 | 1.5+ 0.375+ 1.125 | 1.5+ 0.75+ 0.75 | 0.5+ 0.25+ 0.25 | 1+ 0.5+ 0.5 |
| *Beta vulgaris* | 0 | 0 | 0 | 0 | 0 | 0 | 0 | 0 |
| *Avena fatua* | 100 | 100 | 100 | 100 | 100 | 100 | 80 | 100 |
| *Echinochloa crus-galli* | 100 | 100 | 100 | 100 | 100 | 100 | 85 | 100 |
| *Stellaria media* | 100 | 100 | 100 | 100 | 100 | 100 | 95 | 100 |
| *Galium aparine* | 100 | 100 | 100 | 100 | 100 | 100 | 85 | 100 |
| *Chenopodium album* | 100 | 100 | 95 | 100 | 100 | 100 | 70 | 100 |
| *Alopecurus myosuroides* | 100 | 100 | 100 | 100 | 100 | 100 | 90 | 100 |
| *Lamium amplexicaule* | 100 | 100 | 100 | 100 | 100 | 100 | 90 | 100 |

0 = no damage
100 = complete destruction

EXAMPLE 24

In the greenhouse, various plants were treated at a growth height of from 3 to 16 cm with the following amounts of the following individual active ingredients and compositions thereof as dispersions or emulsions:

II: O-(isopropylaminosulfonyl)-glycolic acid-N-butyn-1-yl-3-anilide
1, 1.5, 2, 2.5, 3, 3.5 and 4 kg/ha,
III: O-(methylaminosulfonyl)-glycolic acid-N-isopropylanilide
1, 2, 2.5, 3 and 4 kg/ha,
XIV: 3-(N-m-methylphenylcarbamoyloxy)-acetoacetic acid anilide
0.25, 0.5, 1, 2, 2.5, 3 and 4 kg/ha,
XXIV: O-(methylaminosulfonyl)-glycolic acid hexamethylene amide,
0.25, 0.5, 1 and 2 kg/ha,
LIV: N-methylacetanilido- -isopropylsulfite
1 and 2 kg/ha,
LXIV: O-(dimethylaminosulfonyl)-glycolic acid-N-methylanilide
1, 2, 3 and 4 kg/ha,
LXVI: O-(diethylaminosulfonyl)-glycolic acid-N-isopropylanilide
1, 2, 3 and 4 kg/ha,
LXV: O-(dimethylaminosulfonyl)-glycolic acid-N-ethylanilide
1 and 2 kg/ha,
XIV+II: 0.5+1.5, 0.5+2.5, 0.5+3.5, 1+1, 1+1.5, 1+2 and 1+3 kg/ha,
XIV+III: 0.5+2, 1+1, 1+2, 2+1 and 2+2 kg/ha,
XIV+XXIV: 0.25+0.25, 0.5+0.5 and 1+1 kg/ha,
XIV+LIV: 1+1 kg/ha,
XIV+LXIV: 1+1, 2+1 and 2+2 kg/ha,
XIV+LXVI: 1+1 kg/ha,
XIV+LXV+1+1 kg/ha.

After 2 to 3 weeks it was ascertained that the compositions had a better herbicidal action than their components, combined with superior crop plant compatibility. The results are given below:

| Active ingredient kg/ha | II 1 | 1.5 | 2 | 2.5 | 3 | 3.5 | 4 | III 1 | 2 | 2.5 | 3 | 4 |
|---|---|---|---|---|---|---|---|---|---|---|---|---|
| Crop plants: | | | | | | | | | | | | |
| *Beta vulgaris* | 0 | 0 | 0 | 0 | 0 | 5 | 10 | 0 | 0 | 0 | 0 | 8 |
| Unwanted plants: | | | | | | | | | | | | |
| *Avena fatua* | 50 | 55 | 60 | 63 | 65 | 68 | 70 | 50 | 65 | 68 | 70 | 72 |
| *Echinochloa crus-galli* | 70 | 78 | 80 | 90 | 95 | 100 | 100 | 70 | 80 | 85 | 90 | 100 |
| *Stellaria media* | 15 | 25 | 30 | 34 | 35 | 37 | 40 | 15 | 30 | 35 | 40 | 50 |
| *Galium aparine* | 20 | 24 | 28 | 35 | 40 | 44 | 46 | 15 | 25 | 35 | 41 | 45 |
| *Chenopodium album* | 40 | 50 | 55 | 58 | 60 | 65 | 70 | 30 | 40 | 43 | 45 | 55 |
| *Alopecurus myosuroides* | 90 | 95 | 100 | 100 | 100 | 100 | 100 | 90 | 100 | 100 | 100 | 100 |
| *Lamium amplexicaule* | 15 | 30 | 40 | 48 | 50 | 55 | 60 | 15 | 25 | 30 | 35 | 40 |

| Active ingredient kg/ha | XIV 0.25 | 0.5 | 1 | 2 | 2.5 | 3 | 4 | XXIV 0.25 | 0.5 | 1 | 2 |
|---|---|---|---|---|---|---|---|---|---|---|---|
| *Beta vulgaris* | 0 | 0 | 0 | 0 | 0 | 15 | 20 | 0 | 0 | 0 | 5 |
| *Avena fatua* | 3 | 5 | 10 | 20 | 25 | 30 | 40 | 18 | 30 | 45 | 70 |
| *Echinochloa crus-galli* | 5 | 10 | 30 | 65 | 75 | 80 | 95 | 30 | 40 | 70 | 90 |
| *Stellaria media* | 30 | 50 | 90 | 98 | 100 | 100 | 100 | 10 | 20 | 40 | 60 |
| *Galium aparine* | 20 | 30 | 55 | 75 | 85 | 95 | 100 | 10 | 20 | 35 | 50 |
| *Chenopodium album* | 25 | 50 | 85 | 100 | 100 | 100 | 100 | 7 | 15 | 25 | 45 |
| *Alopecurus myosuroides* | 0 | 5 | 25 | 40 | 50 | 55 | 70 | 35 | 50 | 75 | 95 |
| *Lamium amplexicaule* | 20 | 45 | 80 | 85 | 95 | 100 | 100 | 0 | 5 | 20 | 45 |

| Active ingredient kg/ha | LIV 1 | 2 | LXIV 1 | 2 | 3 | 4 | LXVI 1 | 2 | LXV 1 | 2 |
|---|---|---|---|---|---|---|---|---|---|---|
| *Beta vulgaris* | 0 | 0 | 0 | 0 | 0 | 15 | 0 | 0 | 0 | 0 |
| *Avena fatua* | 35 | 50 | 40 | 60 | 70 | 80 | 45 | 60 | 45 | 70 |
| *Echinochloa crus-galli* | 50 | 80 | 65 | 80 | 95 | 100 | 60 | 80 | 60 | 95 |
| *Stellaria media* | 25 | 30 | 10 | 20 | 30 | 45 | 10 | 25 | 20 | 30 |
| *Galium aparine* | 0 | 20 | 15 | 30 | 40 | 50 | 20 | 40 | 10 | 30 |
| *Chenopodium album* | 5 | 30 | 25 | 50 | 70 | 85 | 40 | 55 | 25 | 45 |
| *Alopecurus myosuroides* | 50 | 85 | 80 | 100 | 100 | 100 | 85 | 100 | 85 | 100 |
| *Lamium amplexicaule* | 15 | 25 | 20 | 40 | 50 | 65 | 20 | 40 | 25 | 35 |

| Active ingredient kg/ha | XIV +II 0.5+ 1.5 | 0.5+ 2.5 | 0.5+ 3.5 | 1+1 | 1+ 1.5 | 1+2 | 1+3 | XIV +III 0.5+ 2 | 1+1 | 1+2 | 2+1 | 2+2 |
|---|---|---|---|---|---|---|---|---|---|---|---|---|
| *Beta vulgaris* | 0 | 0 | 5 | 0 | 0 | 0 | 15 | 0 | 0 | 0 | 0 | 0 |
| *Avena fatua* | 100 | 100 | 100 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 | 100 |
| *Stellaria media* | 100 | 100 | 100 | 100 | 100 | 100 | 100 | 100 | 100 | 100 | 100 | 100 |
| *Galium aparine* | 100 | 100 | 100 | 100 | 100 | 100 | 100 | 100 | 100 | 100 | 100 | 100 |
| *Chenopodium album* | 100 | 100 | 100 | 100 | 100 | 100 | 100 | 100 | 100 | 100 | 100 | 100 |
| *Alopecurus myosuroides* | 100 | 100 | 100 | 100 | 100 | 100 | 100 | 100 | 100 | 100 | 100 | 100 |
| *Lamium amplexicaule* | 100 | 100 | 100 | 100 | 100 | 100 | 100 | 100 | 100 | 100 | 100 | 100 |

| Active ingredient kg/ha | XIV+ XXIV 0.25+ 0.25 | 0.5+ 0.5 | 1+1 | XIV + LIV 1+1 | XIV+ LXIV 1+1 | 2+1 | 2+2 | XIV+ LXVI 1+1 | XIV+ LXV 1+1 |
|---|---|---|---|---|---|---|---|---|---|
| *Beta vulgaris* | 0 | 0 | 0 | 0 | 0 | 0 | 0 | 0 | 0 |
| *Avena fatua* | 65 | 75 | 95 | 85 | 90 | 100 | 100 | 95 | 95 |
| *Echinochloa crus-galli* | 75 | 90 | 100 | 100 | 100 | 100 | 100 | 100 | 100 |
| *Stellaria media* | 80 | 100 | 100 | 100 | 100 | 100 | 100 | 100 | 100 |
| *Galium aparine* | 70 | 90 | 100 | 95 | 100 | 100 | 100 | 100 | 100 |
| *Chenopodium album* | 75 | 100 | 100 | 100 | 100 | 100 | 100 | 100 | 100 |
| *Alopecurus myosuroides* | 75 | 95 | 100 | 100 | 100 | 100 | 100 | 100 | 100 |
| *Lamium amplexicaule* | 60 | 50 | 100 | 100 | 100 | 100 | 100 | 100 | 100 |

0 = no damage
100 = complete destruction

EXAMPLE 25

In the greenhouse, loamy sandy soil was filled into pots and sown with various seeds. The soil prepared in this manner was then treated with the following amounts of the following individual active ingredients and compositions thereof as high-percentage aqueous suspensions:

I: 1-phenyl-4-amino-5-chloropyridazone-(6)
0.5, 1, 1.25, 1.5, 2, 2.5, 3, 3.5, 4, 5 and 6 kg/ha, II: O-(isopropylaminosulfonyl)-glycolic acid-N-butyn-1-yl-3-anilide
1.5, 2, 3, 4, 5 and 6 kg/ha, III: O-(methylaminosulfonyl)-glycolic acid-N-isopropylanilide
0.76, 1, 1.5, 2, 2.5, 3, 4, 5 and 6 kg/ha, XXIV: O-(methylaminosulfonyl)-glycolic acid hexamethylene amide
0.5, 0.75, 1, 1.5, 2, 3, 3.5 and 4 kg/ha, XXV: O-(ethylaminosulfonyl)-glycolic acid hexamethylene amide
0.5, 1, 1.5, 2, 3 and 4 kg/ha, LIV: N-methylacetanilido- -isopropylsulfite
1, 1.5, 2, 3, 4 and 5.5 kg/ha, LXI: 3-(N-isopropylaminosulfonyloxyacetyl)-3-azabicyclo-(3,2,2)-nonane,
1.5 and 4 kg/ha, I+II: 2.5+1.5, 2+2 and 3+3 kg/ha, I+III: 1.25+0.75, 1+1, 2+1, 2+2, 1.5+1.5, 2.5+1.5, 3+3, 3+1, 3+2, 4+1 and 4+2 kg/ha, I+XXIV: 0.5+0.5, 1+1, 1.25+0.75, 1.5+1.5, 2+1, 2+2, 2.5+0.5, 2.5+1.5, 3+1, 3.5+0.5 and 3+0.5 kg/ha, I+XXV: 2+1, 2+2, 2.5+0.5, 2.5+1.5, 3+1 and 3.5+0.5 kg/ha, I+LIV: 2+1, 2+2, 2.5+1.5, 3+1 and 2.5+3 kg/ha, I+LXI: 2.5+1.5 kg/ha.

After 4 to 5 weeks it was ascertained that the compositions had a better herbicidal action than their components, combined with superior crop plant compatibility. The results are given below:

| Active ingredient | I | | | | | | | | | | |
|---|---|---|---|---|---|---|---|---|---|---|---|
| kg/ha | 0.5 | 1 | 1.25 | 1.5 | 2 | 2.5 | 3 | 3.5 | 4 | 5 | 6 |
| Crop plants: | | | | | | | | | | | |
| *Beta vulgaris* | 0 | 0 | 0 | 0 | 0 | 0 | 0 | 0 | 10 | 15 | 20 |
| Unwanted plants: | | | | | | | | | | | |
| *Avena fatua* | 5 | 12 | 13 | 15 | 20 | 25 | 40 | 60 | 75 | 90 | 100 |
| *Echinochloa crus-galli* | 6 | 13 | 15 | 20 | 32 | 50 | 65 | 70 | 75 | 90 | 100 |
| *Stellaria media* | 20 | 45 | 55 | 60 | 80 | 90 | 95 | 100 | 100 | 100 | 100 |
| *Galium aparine* | 15 | 40 | 45 | 50 | 75 | 80 | 85 | 88 | 90 | 95 | 100 |
| *Chenopodium album* | 25 | 40 | 50 | 60 | 80 | 90 | 95 | 100 | 100 | 100 | 100 |
| *Alopecurus myosuroides* | 6 | 11 | 15 | 19 | 22 | 25 | 30 | 40 | 45 | 60 | 95 |
| *Lamium amplexicaule* | 10 | 20 | 23 | 25 | 40 | 60 | 70 | 80 | 90 | 100 | 100 |

| Wirkstoff | II | | | | | |
|---|---|---|---|---|---|---|
| kg/ha | 1.5 | 2 | 3 | 4 | 5 | 6 |
| *Beta vulgaris* | 0 | 0 | 5 | 10 | 25 | 25 |
| *Avena fatua* | 65 | 75 | 85 | 90 | 95 | 95 |
| *Echinochloa crus-galli* | 95 | 100 | 100 | 100 | 100 | 100 |
| *Stellaria media* | 50 | 60 | 70 | 85 | 95 | 100 |
| *Galium aparine* | 35 | 50 | 60 | 65 | 75 | 95 |
| *Chenopodium album* | 40 | 55 | 65 | 70 | 80 | 95 |
| *Alopecurus myosuroides* | 95 | 100 | 100 | 100 | 100 | 100 |
| *Lamium amplexicaule* | 60 | 70 | 80 | 85 | 95 | 100 |

| Active ingredient | III | | | | | | | | |
|---|---|---|---|---|---|---|---|---|---|
| kg/ha | 0.75 | 1 | 1.5 | 2 | 2.5 | 3 | 4 | 5 | 6 |
| *Beta vulgaris* | 0 | 0 | 0 | 0 | 0 | 0 | 10 | 20 | 30 |
| *Avena fatua* | 30 | 40 | 45 | 54 | 70 | 75 | 80 | 90 | 85 |
| *Echinochloa crus-galli* | 45 | 70 | 90 | 100 | 100 | 100 | 100 | 100 | 100 |
| *Stellaria media* | 20 | 25 | 45 | 55 | 60 | 65 | 70 | 85 | 100 |
| *Galium aparine* | 12 | 15 | 25 | 30 | 35 | 40 | 43 | 45 | 60 |
| *Chenopodium album* | 17 | 20 | 35 | 45 | 48 | 50 | 57 | 65 | 75 |
| *Alopecurus myosuroides* | 40 | 50 | 90 | 100 | 100 | 100 | 100 | 100 | 100 |
| *Lamium amplexicaule* | 15 | 20 | 35 | 55 | 58 | 60 | 70 | 75 | 90 |

| Active ingredient | XXIV | | | | | | | |
|---|---|---|---|---|---|---|---|---|
| kg/ha | 0.5 | 0.75 | 1 | 1.5 | 2 | 3 | 3.5 | 4 |
| *Beta vulgaris* | 0 | 0 | 0 | 0 | 0 | 5 | 7 | 10 |
| *Avena fatua* | 25 | 35 | 60 | 75 | 80 | 90 | 96 | 100 |
| *Echinochloa crus-galli* | 35 | 45 | 60 | 90 | 100 | 100 | 100 | 100 |
| *Stellaria media* | 25 | 30 | 50 | 75 | 85 | 95 | 100 | 100 |
| *Galium aparine* | 25 | 30 | 40 | 50 | 65 | 75 | 80 | 85 |
| *Chenopodium album* | 30 | 35 | 40 | 45 | 60 | 70 | 80 | 90 |
| *Alopecurus myosuroides* | 40 | 60 | 75 | 90 | 95 | 100 | 100 | 100 |
| *Lamium amplexicaule* | 25 | 30 | 50 | 70 | 80 | 95 | 100 | 100 |

| Active ingredient | XXV | | | | | | LIV | | | | | |
|---|---|---|---|---|---|---|---|---|---|---|---|---|
| kg/ha | 0.5 | 1 | 1.5 | 2 | 3 | 4 | 1 | 1.5 | 2 | 3 | 4 | 5.5 |
| *Beta vulgaris* | 0 | 0 | 0 | 0 | 7 | 10 | 0 | 0 | 0 | 0 | 5 | 20 |
| *Avena fatua* | 35 | 70 | 85 | 95 | 100 | 100 | 40 | 55 | 65 | 80 | 95 | 100 |
| *Echinochloa crus-galli* | 45 | 75 | 90 | 95 | 100 | 100 | 70 | 80 | 90 | 100 | 100 | 100 |
| *Stellaria media* | 25 | 40 | 65 | 75 | 90 | 100 | 30 | 43 | 60 | 75 | 90 | 100 |
| *Galium aparine* | 15 | 20 | 35 | 45 | 60 | 80 | 20 | 30 | 35 | 45 | 60 | 80 |
| *Chenopodium album* | 20 | 40 | 55 | 70 | 85 | 95 | 40 | 56 | 65 | 70 | 90 | 100 |
| *Alopecurus myosuroides* | 45 | 70 | 90 | 95 | 100 | 100 | 60 | 80 | 85 | 95 | 100 | 100 |
| *Lamium amplexicaule* | 15 | 20 | 40 | 60 | 70 | 90 | 30 | 40 | 50 | 65 | 85 | 95 |

| Active ingredient | LXI | | I + II | | |
|---|---|---|---|---|---|
| kg/ha | 1.5 | 4 | 2.5+1.5 | 2+2 | 3+3 |
| *Beta vulgaris* | 0 | 12 | 0 | 0 | 5 |
| *Avena fatua* | 60 | 90 | 100 | 100 | 100 |
| *Echinochloa crus-galli* | 90 | 100 | 100 | 100 | 100 |
| *Stellaria media* | 40 | 80 | 100 | 100 | 100 |
| *Galium aparine* | 15 | 65 | 100 | 100 | 100 |
| *Chenopodium album* | 25 | 70 | 100 | 100 | 100 |
| *Alopecurus myosuroides* | 85 | 100 | 100 | 100 | 100 |

-continued

| | | | | | | |
|---|---|---|---|---|---|---|
| *Lamium amplexicaule* | 20 | 70 | | 100 | 100 | 100 |

| Active ingredient kg/ha | I + III 1.25+ 0.75 | 1+1 | 2+1 | 2+2 | 1.5+ 1.5 | 2.5+ 1.5 | 3+3 | 3+1 | 3+2 | 4+1 | 4+2 |
|---|---|---|---|---|---|---|---|---|---|---|---|
| *Beta vulgaris* | 0 | 0 | 0 | 0 | 0 | 0 | 0 | 0 | 0 | 10 | 10 |
| *Avena fatua* | 85 | 93 | 100 | 100 | 100 | 100 | 100 | 100 | 100 | 100 | 100 |
| *Echinochloa crus-galli* | 100 | 100 | 100 | 100 | 100 | 100 | 100 | 100 | 100 | 100 | 100 |
| *Stellaria media* | 100 | 100 | 100 | 100 | 100 | 100 | 100 | 100 | 100 | 100 | 100 |
| *Galium aparine* | 96 | 95 | 100 | 100 | 100 | 100 | 100 | 100 | 100 | 100 | 100 |
| *Chenopodium album* | 100 | 100 | 100 | 100 | 100 | 100 | 100 | 100 | 100 | 100 | 100 |
| *Alopecurus myosuroides* | 95 | 100 | 100 | 100 | 100 | 100 | 100 | 100 | 100 | 100 | 100 |
| *Lamium amplexicaule* | 78 | 80 | 100 | 100 | 100 | 100 | 100 | 100 | 100 | 100 | 100 |

| Active ingredient kg/ha | I + XXIV 0.5+ 0.5 | 1+1 | 1.25+ 0.75 | 1.5+ 1.5 | 2+1 | 2+2 | 2.5+ 0.5 | 2.5+ 1.5 | 3+1 | 3.5+ 0.5 | 3+0.5 |
|---|---|---|---|---|---|---|---|---|---|---|---|
| *Beta vulgaris* | 0 | 0 | 0 | 0 | 0 | 0 | 0 | 0 | 0 | 0 | 0 |
| *Avena fatua* | 70 | 100 | 90 | 100 | 100 | 100 | 95 | 100 | 100 | 100 | 100 |
| *Echinochloa crus-galli* | 83 | 100 | 100 | 100 | 100 | 100 | 100 | 100 | 100 | 100 | 100 |
| *Stellaria media* | 85 | 100 | 100 | 100 | 100 | 100 | 100 | 100 | 100 | 100 | 100 |
| *Galium aparine* | 80 | 100 | 100 | 100 | 100 | 100 | 100 | 100 | 100 | 100 | 100 |
| *Chenopodium album* | 95 | 100 | 100 | 100 | 100 | 100 | 100 | 100 | 100 | 100 | 100 |
| *Alopecurus myosuroides* | 87 | 100 | 100 | 100 | 100 | 100 | 100 | 100 | 100 | 100 | 100 |
| *Lamium amplexicaule* | 75 | 100 | 90 | 100 | 100 | 100 | 100 | 100 | 100 | 100 | 100 |

| Active ingredient kg/ha | I + XXV 1+2 | 2+2 | 2.5+ 0.5 | 2.5+ 1.5 | 3+1 | 3.5+ 0.5 |
|---|---|---|---|---|---|---|
| *Beta vulgaris* | 0 | 0 | 0 | 0 | 0 | 0 |
| *Avena fatua* | 100 | 100 | 100 | 100 | 100 | 100 |
| *Echinochloa crus-galli* | 100 | 100 | 100 | 100 | 100 | 100 |
| *Stellaria media* | 100 | 100 | 100 | 100 | 100 | 100 |
| *Galium aparine* | 100 | 100 | 100 | 100 | 100 | 100 |
| *Chenopodium album* | 100 | 100 | 100 | 100 | 100 | 100 |
| *Alopecurus myosuroides* | 100 | 100 | 100 | 100 | 100 | 100 |
| *Lamium amplexicaule* | 100 | 100 | 100 | 100 | 100 | 100 |

| Active ingredient kg/ha | I + LIV 2+1 | 2+2 | 2.5+ 1.5 | 3+1 | 2.5+ 3 | I + LXI 2.5+1.5 |
|---|---|---|---|---|---|---|
| *Beta vulgaris* | 0 | 0 | 0 | 0 | 0 | 0 |
| *Avena fatua* | 100 | 100 | 100 | 100 | 100 | 100 |
| *Echinochloa crus-galli* | 100 | 100 | 100 | 100 | 100 | 100 |
| *Stellaria media* | 100 | 100 | 100 | 100 | 100 | 100 |
| *Galium aparine* | 100 | 100 | 100 | 100 | 100 | 100 |
| *Chenopodium album* | 100 | 100 | 100 | 100 | 100 | 100 |
| *Alopecurus myosuroides* | 100 | 100 | 100 | 100 | 100 | 100 |
| *Lamium amplexicaule* | 100 | 100 | 100 | 100 | 100 | 100 |

0 = no damage
100 + complete destruction

EXAMPLE 26

In the greenhouse, various plants were treated at a growth height of from 3 to 17 cm with the following amounts of the following individual active ingredients and compositions thereof as dispersions:

I: 1-phenyl-4-amino-5-chloropyridazone(6),

III: O-(methylaminosulfonyl)-glycolic acid-N-isopropylanilide

LXI: 3-[N-isopropylaminosulfonyloxyacetyl]-3-azabicyclo-[3,2,2]-nonane, each at rates of 0.5, 1, 1.5, 2, 2.5, 4 and 4.5 kg/ha, I+III+LXI: 0.5+0.5+0.5, 1+0.5+0.5, 0.5+1+0.5, 0.5+0.5+1, 2+1+1, 1+2+1, 1+1+2, 2.5+1.5+0.5, 0.5+2.5+1.5 and 1.5+0.5+2.5 kg/ha.

After 2 to 3 weeks it was ascertained that, at the lower application rates, the compositions had a better herbicidal action than their components, combined with the same crop plant compatibility. At the high application rates, the compositions had a good herbicidal action and good crop tolerance.

The results are given below:

| Active ingredient kg/ha | I 0.5 | 1 | 1.5 | 2 | 2.5 | 4 | 4.5 |
|---|---|---|---|---|---|---|---|
| Crop plants: | | | | | | | |
| *Beta vulgaris* | 0 | 0 | 0 | 0 | 0 | 10 | 10 |
| Unwanted plants: | | | | | | | |
| *Avena fatua* | 5 | 13 | 15 | 25 | 35 | 65 | 75 |
| *Echinochloa crus-galli* | 15 | 25 | 40 | 53 | 70 | 90 | 95 |
| *Stellaria media* | 20 | 40 | 60 | 80 | 90 | 100 | 100 |
| *Galium aparine* | 20 | 40 | 50 | 70 | 75 | 90 | 95 |
| *Chenopodium album* | 30 | 45 | 50 | 65 | 80 | 100 | 100 |
| *Alopecurus myosuroides* | 5 | 35 | 85 | 90 | 95 | 100 | 100 |
| *Lamium amplexicaule* | 10 | 20 | 25 | 40 | 50 | 85 | 90 |

| Active ingredient kg/ha | III 0.5 | 1 | 1.5 | 2 | 2.5 | 4 | 4.5 | LXI 0.5 | 1 | 1.5 | 2 | 2.5 | 4 | 4.5 |
|---|---|---|---|---|---|---|---|---|---|---|---|---|---|---|
| *Beta vulgaris* | 0 | 0 | 0 | 0 | 0 | 10 | 12 | 0 | 0 | 0 | 0 | 0 | 5 | 10 |
| *Avena fatua* | 25 | 50 | 60 | 65 | 68 | 72 | 75 | 20 | 40 | 55 | 65 | 70 | 85 | 90 |
| *Echinochloa crus-galli* | 45 | 70 | 75 | 80 | 85 | 100 | 100 | 25 | 60 | 80 | 90 | 95 | 100 | 100 |
| *Stellaria media* | 5 | 15 | 25 | 30 | 35 | 50 | 55 | 0 | 10 | 20 | 30 | 35 | 60 | 75 |
| *Galium aparine* | 10 | 15 | 20 | 25 | 35 | 45 | 48 | 0 | 5 | 10 | 15 | 20 | 50 | 55 |
| *Chenopodium album* | 10 | 30 | 35 | 40 | 43 | 55 | 60 | 5 | 10 | 15 | 25 | 30 | 50 | 60 |
| *Alopecurus myosuroides* | 50 | 90 | 100 | 100 | 100 | 100 | 100 | 50 | 80 | 90 | 95 | 100 | 100 | 100 |

-continued

| | | | | | | | | | | | | | | |
|---|---|---|---|---|---|---|---|---|---|---|---|---|---|---|
| *Lamium amplexicaule* | 5 | 15 | 20 | 25 | 30 | 40 | 50 | 0 | 5 | 15 | 20 | 25 | 50 | 65 |

| Active Ingredient kg/ha | I + III + LXI 0.5+ 0.5+ 0.5 | 1+ 0.5+ 0.5 | 0.5+ 1+ 0.5 | 0.5+ 0.5+ 1 | 2+1+1 2+1+1 | 1+2+1 1+2+1 | 1+1+2 1+1+2 | 2.5+ 1.5+ 0.5 | 0.5+ 2.5+ 1.5 | 1.5+ 0.5+ 2.5 |
|---|---|---|---|---|---|---|---|---|---|---|
| *Beta vulgaris* | 0 | 0 | 0 | 0 | 0 | 0 | 0 | 0 | 0 | 0 |
| *Avena fatua* | 90 | 98 | 100 | 100 | 100 | 100 | 100 | 100 | 100 | 100 |
| *Echinochloa crus-galli* | 100 | 100 | 100 | 100 | 100 | 100 | 100 | 100 | 100 | 100 |
| *Stellaria media* | 65 | 85 | 80 | 80 | 100 | 100 | 100 | 100 | 100 | 100 |
| *Galium aparine* | 70 | 90 | 75 | 75 | 100 | 100 | 100 | 100 | 100 | 97 |
| *Chenopodium album* | 85 | 100 | 100 | 90 | 100 | 100 | 100 | 100 | 100 | 100 |
| *Alopecurus myosuroides* | 100 | 100 | 100 | 100 | 100 | 100 | 100 | 100 | 100 | 100 |
| *Lamium amplexicaule* | 55 | 65 | 68 | 60 | 100 | 90 | 95 | 100 | 95 | 90 |

0 = no damage
100 = complete destruction

EXAMPLE 27

In the greenhouse, loamy sandy soil was filled into pots and sown with various seeds. The soil prepared in this manner was then treated with the following amounts of the following individual active ingredients and compositions thereof as dispersions:

I: 1-phenyl-4-amino-5-chloropyridazone-(6)

III: O-(methylaminosulfonyl)-glycolic acid-N-isopropylanilide

LXI: 3-(N-isopropylaminosulfonyloxyacetyl)-3-azabicyclo-(3,2,2)-nonane each at rates of 0.5, 1, 1.5, 2, 2.5, 4 and 4.5 kg/ha, I+III+LXI: 0.5+0.5+0.5, 1+0.5+0.5, 0.5+1+0.5, 0.5+0.5+1, 2+1+1, 1+2+1, 1+1+2, 2.5+1.5+0.5, 0.5+2.5+1.5 and 1.5+0.5+2.5 kg/ha.

After 4 to 5 weeks it was ascertained that, at the lower application rates, the compositions had a better herbicidal action than their components, combined with the same crop plant compatibility. At the higher application rates the compositions provided good weed control and had good crop tolerance.

The results are given below:

| Active ingredient kg/ha | I 0.5 | 1 | 1.5 | 2 | 2.5 | 4 | 4.5 | III 0.5 | 1 | 1.5 | 2 | 2.5 | 4 | 4.5 |
|---|---|---|---|---|---|---|---|---|---|---|---|---|---|---|
| Crop plants: | | | | | | | | | | | | | | |
| *Beta vulgaris* | 0 | 0 | 0 | 0 | 0 | 10 | 12 | 0 | 0 | 0 | 0 | 0 | 10 | 15 |
| Unwanted plants: | | | | | | | | | | | | | | |
| *Avena fatua* | 5 | 12 | 15 | 20 | 25 | 75 | 85 | 15 | 40 | 45 | 54 | 70 | 80 | 85 |
| *Echinochloa crus-galli* | 6 | 13 | 20 | 32 | 50 | 75 | 88 | 25 | 70 | 90 | 100 | 100 | 100 | 100 |
| *Stellaria media* | 20 | 45 | 60 | 80 | 90 | 100 | 100 | 10 | 25 | 45 | 55 | 60 | 70 | 80 |
| *Galium aparine* | 15 | 40 | 50 | 75 | 80 | 90 | 93 | 10 | 15 | 25 | 30 | 35 | 43 | 45 |
| *Chenopodium album* | 25 | 40 | 60 | 80 | 90 | 100 | 100 | 15 | 20 | 35 | 45 | 48 | 57 | 60 |
| *Alopecurus myosuroides* | 6 | 11 | 19 | 22 | 25 | 45 | 55 | 20 | 50 | 90 | 100 | 100 | 100 | 100 |
| *Lamium amplexicaule* | 10 | 20 | 25 | 40 | 60 | 90 | 95 | 10 | 20 | 35 | 55 | 58 | 70 | 73 |

| Active ingredient kg/ha | LXI 0.5 | 1 | 1.5 | 2 | 2.5 | 4 | 4.5 |
|---|---|---|---|---|---|---|---|
| *Beta vulgaris* | 0 | 0 | 0 | 0 | 5 | 12 | 15 |
| *Avena fatua* | 25 | 40 | 60 | 65 | 70 | 90 | 95 |
| *Echinochloa crus-galli* | 50 | 70 | 90 | 95 | 100 | 100 | 100 |
| *Stallaria media* | 10 | 20 | 40 | 50 | 60 | 80 | 95 |
| *Gallium aparine* | 5 | 10 | 15 | 30 | 40 | 65 | 80 |
| *Chenopodium album* | 10 | 20 | 25 | 35 | 50 | 70 | 85 |
| *Alopecurus myosuroides* | 40 | 60 | 85 | 95 | 100 | 100 | 100 |
| *Lamium amplexicaule* | 10 | 15 | 20 | 40 | 50 | 70 | 80 |

| Active ingredient kg/ha | I + III + LXI 0.5+ 0.5+ 0.5 | 1+ 0.5+ 0.5 | 0.5+ 1+ 0.5 | 0.5+ 0.5+ 1 | 2+1+1 | 1+2+1 | 1+1+2 | 2.5+ 1.5+ 0.5 | 0.5+ 2.5+ 1.5 | 1.5+ 0.5+ 2.5 |
|---|---|---|---|---|---|---|---|---|---|---|
| *Beta vulgaris* | 0 | 0 | 0 | 0 | 0 | 0 | 0 | 0 | 0 | 5 |
| *Avena fatua* | 85 | 92 | 100 | 100 | 100 | 100 | 100 | 100 | 100 | 100 |
| *Echinochloa crus-galli* | 100 | 100 | 100 | 100 | 100 | 100 | 100 | 100 | 100 | 100 |
| *Stellaria media* | 80 | 100 | 95 | 90 | 100 | 100 | 100 | 100 | 100 | 100 |
| *Galium aparine* | 70 | 95 | 78 | 77 | 100 | 100 | 100 | 100 | 100 | 100 |
| *Chenopodium album* | 90 | 100 | 95 | 100 | 100 | 100 | 100 | 100 | 100 | 100 |
| *Alopecurus myosuroides* | 100 | 100 | 100 | 100 | 100 | 100 | 100 | 100 | 100 | 100 |
| *Lamium amplexicaule* | 70 | 80 | 80 | 75 | 100 | 100 | 100 | 100 | 100 | 100 |

0 = no damage
100 = complete destruction

EXAMPLE 28

In the greenhouse, various plants were treated at a growth height of from 2 to 12 cm with the following amounts of the following individual active ingredients and compositions thereof as emulsions or dispersions:

XII: 3-methoxycarbonylaminophenyl-N-(3'-methylphenyl)carbamate

XIII: 3-(N-m-trifluoromethylphenylcarbamoyloxy)-(p-methylphenyl)-methylcarbamate LXI: 3-(N-isopropylaminosulfonyloxyacetyl)-3-azabicyclo-(3,2,2)-nonane each at rates of 0.5, 1, 1.5, 2 and 3 kg/ha, XII+LXI and XIII+LXI, each at rates of 2+1, 1+2, 1.5+0.5 0.5+1.5 kg/ha.

After 2 to 3 weeks it was ascertained that, at the lower application rates, the compositions had a better herbicidal action than their components, combined with the same crop plant compatibility. At the higher application rates, the compositions provided good weed control and had good crop tolerance.

The results are given below:

LXI: 3-(N-isopropylaminosulfonyloxyacetyl)-3-azabicyclo-(3,2,2)-nonane

LXIX: 3-methyl-4-amino-5H-6-phenyl-1,2,4-triazin-5-one

| | XII | | | | | XIII | | | | |
|---|---|---|---|---|---|---|---|---|---|---|
| | 0.5 | 1 | 1.5 | 2 | 3 | 0.5 | 1 | 1.5 | 2 | 3 |
| Crop plants: | | | | | | | | | | |
| *Beta vulgaris* | 0 | 0 | 5 | 15 | 30 | 0 | 0 | 0 | 0 | 20 |
| Unwanted plants: | | | | | | | | | | |
| *Avena fatua* | 3 | 20 | 25 | 30 | 40 | 10 | 15 | 30 | 40 | 50 |
| *Echinochloa crus-galli* | 10 | 15 | 20 | 30 | 40 | 16 | 35 | 65 | 80 | 90 |
| *Stellaria media* | 45 | 60 | 80 | 95 | 100 | 70 | 95 | 100 | 100 | 100 |
| *Galium aparine* | 15 | 30 | 50 | 70 | 80 | 28 | 55 | 60 | 70 | 90 |
| *Chenopodium album* | 30 | 60 | 80 | 100 | 100 | 60 | 100 | 100 | 100 | 100 |
| *Alopecurus myosuroides* | 5 | 10 | 15 | 20 | 25 | 5 | 50 | 55 | 60 | 70 |

| Active ingredients kg/ha | LXI 0.5 | 1 | 1.5 | 2 | 3 | XII + LXI 2+1 | 1+2 | 1.5+ 0.5 | 0.5+ 1.5 | XIII + LXI 2+1 | 1+2 | 1.5+ 0.5 | 0.5+ 1.5 |
|---|---|---|---|---|---|---|---|---|---|---|---|---|---|
| *Beta vulgaris* | 0 | 0 | 0 | 0 | 0 | 15 | 0 | 5 | 0 | 0 | 0 | 0 | 0 |
| *Avena fatua* | 20 | 40 | 55 | 65 | 78 | 100 | 100 | 85 | 98 | 100 | 100 | 90 | 100 |
| *Echinochloa crus-galli* | 25 | 60 | 80 | 90 | 100 | 100 | 100 | 90 | 100 | 100 | 100 | 100 | 100 |
| *Stellaria media* | 0 | 10 | 20 | 30 | 50 | 100 | 100 | 100 | 100 | 100 | 100 | 100 | 100 |
| *Galium aparine* | 0 | 5 | 10 | 15 | 40 | 100 | 85 | 90 | 70 | 100 | 100 | 100 | 78 |
| *Chenopodium album* | 5 | 10 | 15 | 25 | 40 | 100 | 100 | 100 | 100 | 100 | 100 | 100 | 100 |
| *Alopecurus myosuroides* | 50 | 80 | 90 | 95 | 100 | 100 | 100 | 100 | 100 | 100 | 100 | 100 | 100 |

0 = no damage
100 = complete destruction

EXAMPLE 29

In the greenhouse, loamy sandy soil was filled into pots and sown with various seeds. The soil prepared in this manner was then created with the following amounts of the following individual ingredients and compositions thereof as dispersions or emulsions:

III: O-(methylaminosulfonyl)-glycolic acid-N-isopropylanilide

XXIV: O-(methylaminosulfonyl)-glycolic acid hexamethylene amide each at rates of 0.5, 1, 1.5, 2, 3 and 4 kg/ha, III+LXIX, XXIV+LXIX and LXI+LXIX each at rates of 1+1, 1.5+0.5, 0.5+1.5, 1.5+1.5, 2+1 and 1+2 kg/ha.

After 4 to 5 weeks it was ascertained that, at the lower application rates, the compositions had a better herbicidal action than their components, combined with the same crop plant compatibility. At the higher rates, the compositions had a strong herbicidal action.

The results are given below:

| Active ingredient | I | | | | | | III | | | | | |
|---|---|---|---|---|---|---|---|---|---|---|---|---|
| kg/ha | 0.5 | 1 | 1.5 | 2 | 3 | 4 | 0.5 | 1 | 1.5 | 2 | 3 | 4 |
| Crop plants: | | | | | | | | | | | | |
| *Beta vulgaris* | 0 | 0 | 0 | 0 | 0 | 10 | 0 | 0 | 0 | 0 | 0 | 10 |
| Unwanted plants: | | | | | | | | | | | | |
| *Avena fatua* | 5 | 12 | 15 | 20 | 40 | 75 | 15 | 40 | 45 | 54 | 75 | 80 |
| *Echinochloa crus-galli* | 6 | 13 | 20 | 32 | 65 | 75 | 25 | 70 | 90 | 100 | 100 | 100 |
| *Stellaria media* | 20 | 45 | 60 | 80 | 95 | 100 | 10 | 25 | 45 | 55 | 65 | 70 |
| *Galium aparine* | 15 | 40 | 50 | 75 | 85 | 90 | 10 | 15 | 25 | 30 | 40 | 43 |
| *Chenopodium album* | 25 | 40 | 60 | 80 | 95 | 100 | 15 | 20 | 35 | 45 | 50 | 57 |
| *Alopecurus myosuroides* | 6 | 11 | 19 | 22 | 30 | 45 | 20 | 50 | 90 | 100 | 100 | 100 |
| *Lamium amplexicaule* | 10 | 20 | 25 | 40 | 70 | 90 | 10 | 20 | 35 | 55 | 60 | 70 |
| Active ingredient | XXIV | | | | | | LXI | | | | | |
| *Beta vulgaris* | 0 | 0 | 0 | 0 | 5 | 10 | 0 | 0 | 0 | 0 | 5 | 12 |
| *Avena fatua* | 25 | 60 | 75 | 80 | 90 | 100 | 25 | 40 | 60 | 65 | 80 | 90 |
| *Echinochloa crus-galli* | 35 | 60 | 90 | 100 | 100 | 100 | 50 | 70 | 90 | 95 | 100 | 100 |
| *Stellaria media* | 25 | 50 | 75 | 85 | 95 | 100 | 10 | 20 | 40 | 50 | 70 | 80 |
| *Galium aparine* | 25 | 40 | 50 | 65 | 75 | 85 | 5 | 10 | 15 | 30 | 50 | 65 |
| *Chenopodium album* | 30 | 40 | 45 | 60 | 70 | 90 | 10 | 20 | 25 | 35 | 50 | 70 |
| *Alopecurus myosuroides* | 40 | 75 | 90 | 95 | 100 | 100 | 40 | 60 | 85 | 95 | 100 | 100 |
| *Alopecurus myosuroides* | 40 | 75 | 90 | 95 | 100 | 100 | 40 | 60 | 85 | 95 | 100 | 100 |
| *Lamium amplexicaule* | 25 | 50 | 70 | 80 | 95 | 100 | 10 | 15 | 20 | 40 | 60 | 70 |

| Active Ingredient | LXIX | | | | | |
|---|---|---|---|---|---|---|
| kg/ha | 0.5 | 1 | 1.5 | 2 | 3 | 4 |
| *Beta vulgaris* | 0 | 0 | 0 | 0 | 0 | 0 |
| *Avena fatua* | 10 | 15 | 25 | 40 | 50 | 65 |
| *Echinochloa crus-galli* | 15 | 25 | 35 | 50 | 70 | 80 |
| *Stellaria media* | 10 | 20 | 30 | 40 | 50 | 75 |
| *Galium aparine* | 10 | 20 | 24 | 30 | 45 | 60 |
| *Chenopodium album* | 15 | 30 | 40 | 55 | 70 | 85 |
| *Alopecurus myosuroides* | 20 | 30 | 40 | 50 | 65 | 80 |
| *Lamium amplexicaule* | 20 | 30 | 35 | 60 | 75 | 90 |

| Active ingredient kg/ha | III + LXIX 1+1 | 1.5+ 0.5 | 0.5+ 1.5 | 1.5+ 1.5 | 2+1 | 1+2 | XXIV + LXIX 1+1 | 1.5+ 0.5 | 0.5+ 1.5 | 1.5+ 1.5 | 2+1 | 1+1 |
|---|---|---|---|---|---|---|---|---|---|---|---|---|

-continued

| | | | | | | | | | | | | |
|---|---|---|---|---|---|---|---|---|---|---|---|---|
| *Beta vulgaris* | 0 | 0 | 0 | 0 | 0 | 0 | 0 | 0 | 0 | 0 | 0 | 0 |
| *Avena fatua* | 95 | 95 | 80 | 100 | 100 | 92 | 100 | 100 | 90 | 100 | 100 | 100 |
| *Echinochloa crus-galli* | 100 | 100 | 100 | 100 | 100 | 100 | 100 | 100 | 100 | 100 | 100 | 100 |
| *Stellaria media* | 85 | 95 | 80 | 100 | 100 | 100 | 100 | 100 | 95 | 100 | 100 | 100 |
| *Galium aparine* | 75 | 75 | 75 | 90 | 90 | 100 | 100 | 100 | 90 | 100 | 100 | 100 |
| *Chenopodium album* | 90 | 90 | 95 | 100 | 100 | 100 | 100 | 100 | 100 | 100 | 100 | 100 |
| *Alopecurus myosuroides* | 100 | 100 | 100 | 100 | 100 | 100 | 100 | 100 | 100 | 100 | 100 | 100 |
| *Lamium amplexicaule* | 90 | 95 | 85 | 100 | 100 | 100 | 100 | 100 | 100 | 100 | 100 | 100 |

| Active ingredient | LXI + LXIX | | | | | |
|---|---|---|---|---|---|---|
| kg/ha | 1+1 | 1.5+ 0.5 | 0.5+ 1.5 | 1.5+ 1.5 | 2+1 | 1+2 |
| *Beta vulgaris* | 0 | 0 | 0 | 0 | 0 | 0 |
| *Avena fatua* | 95 | 100 | 90 | 100 | 100 | 100 |
| *Echinochloa crus-galli* | 100 | 100 | 100 | 100 | 100 | 100 |
| *Stellaria media* | 80 | 90 | 80 | 100 | 100 | 100 |
| *Galium aparine* | 70 | 68 | 70 | 80 | 90 | 80 |
| *Chenopodium album* | 90 | 80 | 90 | 100 | 100 | 100 |
| *Alopecurus myosuroides* | 100 | 100 | 100 | 100 | 100 | 100 |
| *Lamium amplexicaule* | 85 | 80 | 85 | 95 | 100 | 100 |

| Active ingredient | I + III + LXIX | | | | | | |
|---|---|---|---|---|---|---|---|
| kg/ha | 1+ 0.5+ 0.5 | 0.5+ 1+ 0.5 | 0.5+ 0.5+ 1 | 1+1+1 | 2+1+1 | 1+2+1 | 1+1+2 |
| *Beta vulgaris* | 0 | 0 | 0 | 0 | 0 | 0 | 0 |
| *Avena fatua* | 79 | 95 | 75 | 100 | 100 | 100 | 100 |
| *Echinochola crus-galli* | 95 | 100 | 96 | 100 | 100 | 100 | 100 |
| *Stellaria media* | 100 | 95 | 90 | 100 | 100 | 100 | 100 |
| *Galium aparine* | 100 | 80 | 85 | 100 | 100 | 100 | 100 |
| *Chenopodium album* | 100 | 100 | 100 | 100 | 100 | 100 | 100 |
| *Alopecurus myosuroides* | 93 | 100 | 98 | 100 | 100 | 100 | 100 |
| *Lamium amplexicaule* | 90 | 90 | 90 | 100 | 100 | 100 | 100 |

| Active ingredient | I + XXIV + LXIX | | | | | | |
|---|---|---|---|---|---|---|---|
| kg/ha | 1+ 0.5+ 0.5 | 0.5+ 1+ 0.5 | 0.5+ 0.5+ 1 | 1+1+1 | 2+1+1 | 1+2+1 | 1+1+2 |
| *Beta vulgaris* | 0 | 0 | 0 | 0 | 0 | 0 | 0 |
| *Avena fatua* | 87 | 100 | 85 | 100 | 100 | 100 | 100 |
| *Echinochola crus-galli* | 100 | 100 | 100 | 100 | 100 | 100 | 100 |
| *Stellaria media* | 100 | 100 | 100 | 100 | 100 | 100 | 100 |
| *Galium aparine* | 100 | 100 | 100 | 100 | 100 | 100 | 100 |
| *Chenopodium album* | 100 | 100 | 100 | 100 | 100 | 100 | 100 |
| *Alopecurus myosuroides* | 100 | 100 | 100 | 100 | 100 | 100 | 100 |
| *Lamium amplexicaule* | 100 | 100 | 100 | 100 | 100 | 100 | 100 |

| Active ingredient | I + LXI + LXIX | | | | | | |
|---|---|---|---|---|---|---|---|
| *Beta vulgaris* | 0 | 0 | 0 | 0 | 0 | 0 | 0 |
| *Avena fatua* | 87 | 95 | 85 | 100 | 100 | 100 | 100 |
| *Echinochola crus-galli* | 100 | 100 | 100 | 100 | 100 | 100 | 100 |
| *Stellaria media* | 100 | 90 | 90 | 100 | 100 | 100 | 100 |
| *Galium aparine* | 95 | 75 | 80 | 100 | 100 | 100 | 100 |
| *Chenopodium album* | 100 | 100 | 100 | 100 | 100 | 100 | 100 |
| *Alopecurus myosuroides* | 100 | 100 | 100 | 100 | 100 | 100 | 100 |
| *Lamium amplexicaule* | 90 | 85 | 90 | 100 | 100 | 100 | 100 |

0 = no damage
100 = complete destruction

EXAMPLE 30

In the greenhouse, various plants were treated at a growth height of from 2 to 15 cm with the following amounts of the following individual active ingredients and compositions therof as dispersions, emulsions or suspensions:

I: 1-phenyl-4-amino-5-chloropyridazone-(6)

III: O-(methylaminosulfonyl)-glycolic acid-N-isopropylanilide

XXIV: O-(methylaminosulfonyl)-glycolic acid hexamethylene amide

LXI: 3-(N-isopropylaminosulfonyloxyacetyl)-3-azabicyclo-(3,2,2)-nonane

LXIX: 3-methyl-4-amino-5H-6-phenyl-1,2,4-triazin-5-one, each at rates of 0.5, 1, 1.5, 2, 3 and 4 kg/ha, III+LXIX, XXIV+LXIX and LXI+LXIX each at rates of 1+1, 1.5+0.5, 0.5+1.5, 1.5+1.5, 2+1 and 1+2 kg/ha.

After 2 to 3 weeks it was ascertained that, at the lower application rates, the compositions had a better herbicidal action than their components, combined with the same crop plant compatibility. At the higher rates, the compositions had a strong herbicidal action and good crop tolerance.

The results are given below:

| Active ingredient | I | | | | | | III | | | | | |
|---|---|---|---|---|---|---|---|---|---|---|---|---|
| kg/ha | 0.5 | 1 | 1.5 | 2 | 3 | 4 | 0.5 | 1 | 1.5 | 2 | 3 | 4 |
| Crop plants: | | | | | | | | | | | | |
| *Beta vulgaris* | 0 | 0 | 0 | 0 | 0 | 10 | 0 | 0 | 0 | 0 | 0 | 10 |
| Unwanted plants: | | | | | | | | | | | | |
| *Avena fatua* | 5 | 13 | 15 | 25 | 40 | 65 | 25 | 50 | 60 | 65 | 70 | 72 |
| *Echinochloa crus-galli* | 15 | 25 | 40 | 53 | 80 | 90 | 45 | 70 | 75 | 80 | 90 | 100 |

-continued

| | | | | | | | | | | | | |
|---|---|---|---|---|---|---|---|---|---|---|---|---|
| *Stellaria media* | 20 | 40 | 60 | 80 | 95 | 100 | 5 | 15 | 25 | 30 | 40 | 50 |
| *Galium aparine* | 20 | 40 | 50 | 70 | 80 | 90 | 10 | 15 | 20 | 25 | 41 | 45 |
| *Chenopodium album* | 30 | 45 | 50 | 65 | 90 | 100 | 10 | 30 | 35 | 40 | 45 | 55 |
| *Alopecurus myosuroides* | 5 | 35 | 85 | 90 | 100 | 100 | 50 | 90 | 100 | 100 | 100 | 100 |
| *Lamium amplexicaule* | 10 | 20 | 25 | 40 | 60 | 85 | 5 | 15 | 20 | 25 | 35 | 40 |

| Active ingredient | | | XXIV | | | | | | LXI | | | |
|---|---|---|---|---|---|---|---|---|---|---|---|---|
| *Beta vulgaris* | 0 | 0 | 0 | 5 | 10 | 15 | 0 | 0 | 0 | 0 | 0 | 5 |
| *Avena fatua* | 30 | 45 | 60 | 70 | 80 | 95 | 20 | 40 | 55 | 65 | 78 | 85 |
| *Echinochloa crus-galli* | 40 | 70 | 80 | 90 | 98 | 100 | 25 | 60 | 80 | 90 | 100 | 100 |
| *Stellaria media* | 20 | 40 | 45 | 60 | 70 | 85 | 0 | 10 | 20 | 30 | 50 | 60 |
| *Galium aparine* | 20 | 35 | 40 | 50 | 65 | 75 | 0 | 5 | 10 | 15 | 40 | 50 |
| *Chenopodium album* | 15 | 25 | 35 | 45 | 60 | 80 | 5 | 10 | 15 | 25 | 40 | 50 |
| *Alopecurus myosuroides* | 50 | 75 | 90 | 100 | 100 | 50 | 80 | 90 | 95 | 100 | 100 | |
| *Lamium amplexicaule* | 5 | 20 | 35 | 45 | 55 | 60 | 0 | 5 | 15 | 20 | 30 | 50 |

| Active ingredient | LXIX | | | | | |
|---|---|---|---|---|---|---|
| kg/ha | 0.5 | 1 | 1.5 | 2 | 3 | 4 |
| *Beta vulgaris* | 0 | 0 | 0 | 0 | 0 | 0 |
| *Avena fatua* | 20 | 40 | 60 | 80 | 90 | 95 |
| *Echinochloa crus-galli* | 30 | 60 | 70 | 85 | 100 | 100 |
| *Stellaria media* | 0 | 10 | 20 | 30 | 50 | 60 |
| *Galium aparine* | 15 | 30 | 40 | 55 | 70 | 90 |
| *Chenopodium album* | 20 | 35 | 50 | 70 | 85 | 95 |
| *Alopecurus myosuroides* | 30 | 50 | 65 | 80 | 100 | 100 |

| Active ingredient | III + LXIX | | | | | | XXIV + LXIX | | | | | |
|---|---|---|---|---|---|---|---|---|---|---|---|---|
| kg/ha | 1+1 | 1.5+ 0.5 | 0.5+ 1.5 | 1.5+ 1.5 | 2+1 | 1+2 | 1+1 | 1.5+ 0.5 | 0.5+ 1.5 | 1.5+ 1.5 | 2+1 | 1+2 |
| *Beta vulgaris* | 0 | 0 | 0 | 0 | 0 | 0 | 0 | 0 | 0 | 0 | 5 | 0 |
| *Avena fatua* | 100 | 100 | 100 | 100 | 100 | 100 | 100 | 100 | 100 | 100 | 100 | 100 |
| *Echinochola crus-galli* | 100 | 100 | 100 | 100 | 100 | 100 | 100 | 100 | 100 | 100 | 100 | 100 |
| *Stellaria media* | 100 | 100 | 100 | 100 | 100 | 100 | 100 | 100 | 100 | 100 | 100 | 100 |
| *Galium aparine* | 85 | 76 | 90 | 100 | 95 | 100 | 100 | 95 | 100 | 100 | 100 | 100 |
| *Chenopodium album* | 100 | 95 | 100 | 100 | 100 | 100 | 100 | 95 | 100 | 100 | 100 | 100 |
| *Alopecurus myosuroides* | 100 | 100 | 100 | 100 | 100 | 100 | 100 | 100 | 100 | 100 | 100 | 100 |
| *Lamium amplexicaule* | 100 | 85 | 100 | 100 | 100 | 100 | 100 | 100 | 100 | 100 | 100 | 100 |

| Active ingredient | LXI + LXIX | | | | | |
|---|---|---|---|---|---|---|
| kg/ha | 1+1 | 1.5+ 0.5 | 0.5+ 1.5 | 1.5+ 1.5 | 2+1 | 1+2 |
| *Beta vulgaris* | 0 | 0 | 0 | 0 | 0 | 0 |
| *Avena fatua* | 100 | 100 | 100 | 100 | 100 | 100 |
| *Echinochloa crus-galli* | 100 | 100 | 100 | 100 | 100 | 100 |
| *Stellaria media* | 100 | 100 | 100 | 100 | 100 | 100 |
| *Galium aparine* | 75 | 67 | 80 | 90 | 85 | 100 |
| *Chenopodium album* | 85 | 75 | 95 | 100 | 100 | 100 |
| *Alopecurus myosuroides* | 100 | 100 | 100 | 100 | 100 | 100 |
| *Lamium amplexicaule* | 95 | 85 | 100 | 100 | 100 | 100 |

0 = no damage
100 = complete destruction

I claim:

1. A herbicide composition consisting essentially of a herbicidally inert carrier having dispersed therein a herbicidally effective amount of a mixture of a. a member selected from the group consisting of O-(methylaminosulfonyl)-glycolic acid hexamethylene amide and O-(methylaminosulfonyl)-glycolic acid heptamehylene amide, and b. propionic acid-3,4-dichloroanilide in a weight ratio of (a) to (b) in the range of 4:1 to 1:4.

* * * * *